US006800442B2

(12) United States Patent
Zauderer

(10) Patent No.: US 6,800,442 B2
(45) Date of Patent: Oct. 5, 2004

(54) METHODS OF SELECTING POLYNUCLEOTIDES ENCODING ANTIGENS

(75) Inventor: Maurice Zauderer, Pittsford, NY (US)

(73) Assignee: University of Rochester, Rochester, NY (US)

( * ) Notice: Subject to any disclaimer, the term of this patent is extended or adjusted under 35 U.S.C. 154(b) by 40 days.

(21) Appl. No.: 10/034,350

(22) Filed: Jan. 3, 2002

(65) Prior Publication Data

US 2004/0151730 A1 Aug. 5, 2004

Related U.S. Application Data

(62) Division of application No. 08/935,377, filed on Sep. 22, 1997.

(51) Int. Cl.[7] .......................... C12Q 1/68; C12N 15/09; C12N 5/00; C12P 21/00; C07H 21/04

(52) U.S. Cl. ............................. 435/6; 435/5; 435/7.2; 435/7.24; 435/69.3; 435/70.1; 435/325; 435/320.1; 435/456; 435/457; 435/378; 536/23.1; 536/23.5; 536/23.7

(58) Field of Search ............................ 435/5, 6, 7.24, 435/7.2, 69.3, 456, 457, 325, 378, 70.1, 320.1; 536/23.1, 23.5, 23.7

(56) References Cited

U.S. PATENT DOCUMENTS

| | | |
|---|---|---|
| 4,690,915 A | 9/1987 | Rosenberg |
| 5,166,057 A | 11/1992 | Palese et al. |
| 5,494,807 A | 2/1996 | Paoletti et al. |
| 5,530,096 A | 6/1996 | Wölfel et al. |
| 5,578,473 A | 11/1996 | Palese et al. |
| 5,804,382 A | 9/1998 | Sytkowski et al. |
| 5,843,648 A | 12/1998 | Robbins et al. |
| 5,866,383 A | 2/1999 | Moss et al. |
| 5,874,560 A | 2/1999 | Kawakami et al. |
| 2002/0018785 A1 | 2/2002 | Zauderer |
| 2003/0022157 A1 | 1/2003 | Zauderer et al. |

FOREIGN PATENT DOCUMENTS

| | | |
|---|---|---|
| WO | WO 95/33835 A1 | 12/1995 |
| WO | WO 97/24438 A1 | 7/1997 |
| WO | WO 97/26328 A1 | 7/1997 |
| WO | WO 97/34143 A1 | 9/1997 |

OTHER PUBLICATIONS

Aota, S–i., et al., "Nucleotide sequence and molecular evolution of mouse retrovirus–like IAP elements," Gene 56:1–12, Elsevier Science Publishers B.V. (1987).
Bennink, J.R., and Yewdell, J.W., "Recombinant Vaccinia Viruses as Vectors for Studying T Lymphocyte Specificity and Function," Curr. Top. Microbiol. Immunol. 163:153–184, Springer–Verlag (1990).
Böel, P., et al., "BAGE: a New Gene Encoding an Antigen Recognized on Human Melanomas by Cytolytic T Lymphocytes," Immunity 2:167–175, Cell Press (1995).
Panicali, D., and paoletti, E., "Construction of poxviruses as cloning vectors: Insertion of the thymidine kinase gene from herpes simplex virus into the DNA of infectious vaccinia virus," Proc. Natl. Acad. Sci. USA 79:4927–4931, National Academy of Sciences (1982).
Merchlinsky, M., and Moss, B., "Introduction of Foreign DNA into the Vaccinia Virus Genome by in Vitro Ligation: Recombination–Independent Selectable Cloning Vectors," Virology 190:522–526, Academic Press, Inc. (1992).
Merchlinsky, M., et al., "Construction and Characterization of Vaccinia Direct Ligation Vectors," Virology 238:444–451, Academic Press, Inc. (Nov. 1997).
Meyer H., et al., "Mapping of deletions in the genome of the highly attenuated vaccinia virus MVA and their influence on virulence," J. Gen. Virol. 72:1031–1038, Society for General Microbiology (1991).
Pfleiderer, M., et al., "A novel vaccina virus expression system allowing construction of recombinants without the need for selection markers, plasmides and bacterial hosts," J. Gen. Virol. 76:2957–2962, Society for General Microbiology (1995).
Quill, H., "Anergy as a Mechanism of Peripheral T Cell Tolerance," J. Immunol. 156:1325–1327, American Association of Immunologists (Feb. 1996).
Ralph, D., et al., "RNA fingerprinting using arbitrarily primed PCR identifies differently regulated RNAs in milk lung (MylLu) cells growth arrested by transforming growth factor $\beta 1$," Proc. Natl. Acad. Sci. USA 90:10710–10714, National Academy of Sciences (1993).
Sahasrabudhe, D.M., et al., "Shared T Cell–Defined Antigens on Independently Derived Tumors," J. Immunol. 151:6302–6310, American Association of Immunologists (1993).

(List continued on next page.)

Primary Examiner—Christina Chan
Assistant Examiner—Michail Belyavskyi
(74) Attorney, Agent, or Firm—Sterne, Kessler, Goldstein & Fox P.L.L.C.

(57) ABSTRACT

The present invention relates to novel methods for the identification of antigens recognized by cytotoxic T cells (CTLs) and specific for human tumors, cancers, and infected cells, and the use of such antigens in immunogenic compositions or vaccines to induce regression of tumors, cancers, or infections in mammals, including humans. The invention encompasses methods for induction and isolation of cytotoxic T cells specific for human tumors, cancers and infected cells, and for improved selection of genes that encode the target antigens recognized by these specific T cells. The invention also relates to differential display methods that improve resolution of, and that reduce the frequency of false positives of DNA fragments that are differentially expressed in tumorous, cancerous, or infected tissues versus normal tissues. The invention further relates to the engineering of recombinant viruses as expression vectors for tumor, cancer, or infected cell-specific antigens.

54 Claims, 18 Drawing Sheets

OTHER PUBLICATIONS

Sambrook, J., et al., "Identification of cDNA clones of interest," in *Molecular Cloning. A Laboratory Manual*, 2nd ed., Sambrook. J/., et al., eds., Cold Spring Harbor Laboratory Press, Plainview, NY, pp. 8.46–8.52 (1989).

Scheiflinger, F., et al., "Construction of chimeric vaccinia viruses by molecular cloning and packaging," *Proc. Natl. Acad. Sci. USA 89*:9977–9981, National Academy of Sciences (1992).

Shirai, M., et al., "CTL Responses of HLA–A2.1–Transgenic Mice Specific for Hepatitis C Viral Peptides Predict Epitopes for CTL of Humans Carrying HLA–A2.1," *J. Immunol. 154*:2733–2742, American Association of Immunologists (1995).

Sidney, J., et al., "Practical, biochemical and evolutionary implications of the discovery of HLA class I supermotifs," *Immunol. Today 17*:261–266, Elsevier Science, Ltd., (Jun. 1996).

Takahashi, H., et al., "Induction of CD8 cytotoxic T cells by immunization with purified HIV–1 envelope protein in ISCOMs," *Nature 344*:873–875, Macmillan Journals Ltd. (1990).

Torigoe, T., et al., "Tumor Rejection Antigens on BALB3T3 Cells Transformed by Activated Oncogenes," *J. Immunol. 147*:3251–3258, American Association of Immunologists (1991).

van der Bruggen, P., et al., "A Gene Encoding an Antigen Recognized by Cytolytic T Lymphocytes on a Human Melanoma," *Science 254*:1643–1647, American Association for the Advancement of Science (1991).

Van den Eynde, B., et al., "A New Family of Genes Coding for an Antigen Recognized by Autologous Cytolytic T Lymphocytes on a Human Melanoma," *J. Exp. Med. 182*:689–698, Rockefeller University Press (1995).

Vitiello, A., et al., "Analysis of the HLA–restricted Influenza–specific Cytotoxic T Lymphocyte Response in Transgenic Mice Carrying a Chimeric Human–Mouse Class I Major Histocompatibility Complex," *J. Exp. Med. 173*:1007–1015, Rockefelle University Press (1991).

Wang, R.–F., et al., "Development of a Retrovirus–based Complementary DNA Expression System for the Cloning of Tumor Antigens," *Cancer Res. 58*:3519–3525, American Association of Cancer Research (Aug. 1998).

Welsh, J., et al., "Arbitrarily primed PCR fingerprinting of RNA," *Nucleic Acids Res. 20*:4965–4970, Oxford University Press (1992).

Wentworth, P.A., et al., "Differences and similarities in the A2.1–restricted cytotoxic T cell repertoire in humans and human leukocyte antigen–transgenic mice," *Eur. J. Immunol. 26*:97–101, VCH Verlagsgellschaft mbH (Jan. 1996).

Wilson, S.H., and Kuff, E.L., "A Novel DNA Polymerase Activity Found in Association with Intracisternal A–Type Particles," *Proc. Natl. Acad. Sci. USA 69*:1531–1536, National Academy of Sciences (1972).

Wölfel, T., et al., "Immunogenic (tum) variants obtained by mutagenesis of mouse mastocytoma P815," *Immunogenetics 26*:178–187, Springer–Verlag (1987).

Clontech Catalog 1998/1999, "CLONTECH PCR–Select Subtraction," p. 24 (Clontech Laboratories, Inc., Palo Alto, CA) (1998).

Smith, E.S., et al., "Lethality–based selection of recombinant genes in mammalian cells: Application to identifying tumor antigens," *Nat. Med. 7*:967–972, Nature America Inc. (Aug. 2001).

Traversari, C., et al., "Transfection and expression of a gene coding for a human melanoma antigen recognized by autologous cytloytic T lymphocytes," *Immunogenetics 35*:145–152, Springer–Verlag (1992).

Pending Non–Provisional U. S. patent application No. 08/935,377, Zauderer, M., filed Sep. 22, 1997 (Not Published).

Pending Non–Provisional U. S. patent application No. 10/277,161, Zauderer et al., filed Oct. 22, 2002 (No Published).

Brichard, V., et al., "The Tyrosinase Gene Codes for an Antigen Recognized by Autologous Cytolytic T Lymphocytes on HLA–A2 Melanomas," *J. Exp. Med. 178*:489–495, Rockefeller University Press (1993).

de Bergeyck, V., et al., "An intracisternal A–particle sequence codes for an antigen recognized by syngeneic cytolytic T lymphocytes on a mouse spontaneous leukemia," *Eur. J. Immunol. 24*:2203–2212, VCH Verlagsgesellschaft mbH (1994).

Huang, A.Y.C., et al., "Role of Bone Marrow–Derived Cells in Presenting MHC Class I–Restricted Tumor Antigens," *Science 264*:961–965, American Association for the Advancement of Science (1994).

Inaba, K., et al., "Dendritic Cell Progenitors Phagocytose Particulates, Including Bacillus Calmette–Guerin Organisms, and Sensitize MIce to Mycobacterial Antigens In Vivo," *J. Exp. Med. 178*:479–488, Rockefeller University Press (1993).

Inaba, K., et al., "Generation of Large Numbers of Dendritic Cells from Mouse Bone Marrow Cultures Supplemented with Granulocyte/Macrophage Colony–stimulating Factor," *J. Exp. Med. 176*:1693–1702, Rockefeller Univeristy Press (1992).

Janeway, Jr., C.A., and Travers, P., "The generation of T–cell ligands," and "The two classes of MHC molecule have distinct subunit structure but a similar three–dimensional structure," in *Immunobiology. The Immune System in Health and Disease*, Robertson, M. et al., eds., Current Biology, Ltd./Garland Publhsing, Inc. p. 4:2–4:5 (1994).

Kawakami, Y., et al., "Cloning of the gene coding for a shared human melanoma antigen recognized by autologous T cells infiltrating into tumor," *Proc. Natl. Acad. Sci. USA 91*:3515–3519, National Academy of Sciences (1994).

Kitts, P.A., et al., "Linearization of baculovirus DNA enhances the recovery of recombinant virus expression vectors," *Nucleic Acids Res. 18*:5667–5672, IRL Press (1990).

Kitts, P.A., and Possee, R.D., "A Method for Producing Recombinant Baculovirus Expression Vectors at High Frequency," *Biotechniques 14*:810–812, 814, and 816–817, Eaton Publishing Company (1993).

Kuff, E.L., and Lueders, K.K., "The Intracisternal A–Particle Gene Family: Structure and Functional Aspects," *Adv. Cancer. Res. 51*:183–276, Academic Press, Inc. (1988).

LaFace, D.M., et al., "Human CB8 Transgene Regulation of HLA Recognition by Murine T Cells," *J. Exp. Med. 182*:1315–1325, Rockefeller University Press (1995).

Liang, P., and Pardee, A.B., "Differential Display of Eukaryotic Messenger RNA by Means of the Polymerase Chain Reaction," *Science 257*:967–971, American Association for the Advancement of Science (1992).

Lisitsyn, N., et la., "Cloning the Differences Between Two Complex Genomes," *Science 259*:946–951, American Association for the Advancement of Science (1993).

Mackett, M., et al., "Vaccinia virus: A selectable eukaryotic cloning and expression vector," *Proc. Natl. Acad. Sci. USA* 79:7415–7419, National Academy of Sciences (1982).

Mackett M., et al., "General Method for Production and Selection of Infectious Vaccinia Virus Recombinants Expressing FOreign Genes," *J. Virol.* 49:857–864, American Society for Microbiology (1984).

Miyake, S., et al., "Efficient generation of recombinant adenoviruses using adenovirus DNA–terminal protein complex and a cosmid bearing the full–length virus genome," *Proc. Natl. Acad. Sci. USA* 93:1320–1324, National Academy of Sciences (Feb. 1996).

Moss, B., "Vaccinia Virus: A Tool for Research and Vaccine Development," *Science* 252:1662–1667, American Association for the Advancement of Science (1991).

Palese, P., et al., "Negative–strand RNA viruses: Genetic engineering and applications," *Proc. Natl. Acad. Sci. USA* 93:11354–11358, National Academy of Sciences (Oct. 1996).

Buller, R.M.L., et al., "Deletion of the Vaccinia Virus Growth Factor Gene Reduces Virus Virulence," *J. Virol.* 62:866–874, American Society for Microbiology (1988).

Moss, B., et al., "Deletion of a 9,000–Base–Pair Segment of the Vaccinia Virus Genome That Encodes Nonessential Polypeptides," *J. Virol.* 40:387–395, American Society for Microbiology (1981).

Panicali, D., et al., "Two Major DNA Variants Present in Serially Propagated Stocks of the WR Strain of Vaccinia Virus," *J. Virol.* 37:1000–1010, American Society for Microbiology (1981).

Pfleiderer, M., et al., "A novel vaccina virus expression system allowing construction of recombinants without the need for selection markers, plasmids and bacterial hosts, " *J. Gen. Virol.* 76:2957–2962, Society for General Microbiology (1995).

1. p7.5tk 7.5K PROMOTER       NOTI           APAI

5'- GGCCAAAAATTGAAAAACTAGATCTATTTATTGCACGCGGCCGCCATGGGCCCGGCC -3'

2. p7.5/ATG0/tk 7.5K PROMOTER       NOTI       BAMHI  SMAI   PSTI

5'- GGCCAAAAATTGAAAAACTAGATCTATTTATTGCACGCGGCCGCCGTGGATCCCCCGGGCTGCAGGAA

TRANSLATION    TRANSCRIPTION
              SALI                       STOP CODONS    STOP SIGNAL

TTCGATATCAAGCTTATCGATACCGTCGACCTCGAGGGGGGCCTAACTAACTAATTTGTTTTTGT

APAI

GGGCCCGGCC -3'

*FIG. 2A*

5. p7.5/ATG3/tk 7.5K PROMOTER     NOTI     START CODON     BAMHI   SMAI    PSTI

5'- GGCCAAAAATTGAAAAACTAGATCTATTTATTGCACGCGGCCGCCATGACGTGGATCCCCCGGGCTGCAGGAA

TRANSLATION     TRANSCRIPTION
       SALI                               STOP CODONS      STOP SIGNAL

TTCGATATCAAGCTTATCGATACCGTCGACCTCGAGGGGGGGCCTAACTAACTAATTTGTTTTTGT

APAI

GGGCCCGGCC -3'

FIG. 2D a. B/c.N
b. BCB 13
c. BCA 22
d. BCA 34
e. BCA 39

PCR amplification with primers MR_1 + MR_5.

Bands 1 to 4 are examples of differential display in tumors.

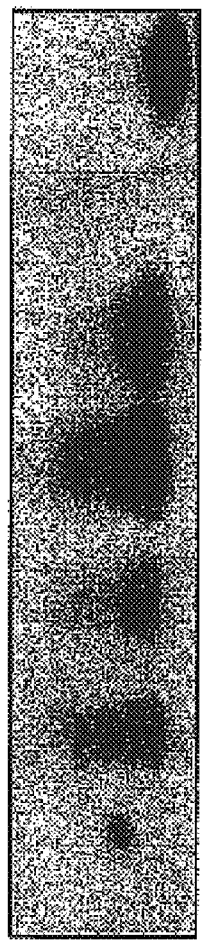 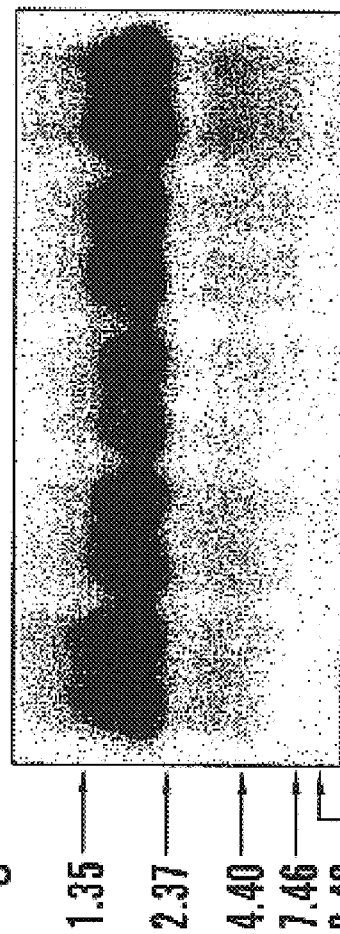
FIG. 8A
FIG. 8B

METHODS OF SELECTING POLYNUCLEOTIDES ENCODING ANTIGENS

CROSS REFERENCE TO RELATED APPLICATIONS

This Application is a Divisional of U.S. patent application Ser. No. 08/935,377, filed Sep. 22, 1997, which is incorporated herein by reference in its entirety.

STATEMENT REGARDING FEDERALLY SPONSORED RESEARCH OR DEVELOPMENT

The work reflected in this application was supported, in part, by a grant from the National Institutes of Health, and the Government may have certain rights in the invention.

FIELD OF THE INVENTION

The present invention relates to novel methods for the identification of antigens recognized by cytotoxic T cells (CTLs) and specific for human tumors, cancers, and infected cells, and the use of such antigens in immunogenic compositions or vaccines to induce regression of tumors, cancers, or infections in mammals, including humans. The invention encompasses methods for induction and isolation of cytotoxic T cells specific for human tumors, cancers or infected cells, and for improved selection of genes that encode the target antigens recognized by these specific T cells. The invention also relates to differential display methods that improve resolution of, and that reduce the frequency of false positives of DNA fragments that are differentially expressed in tumorous, cancerous, or infected tissues versus normal tissues. The invention further relates to the engineering of recombinant viruses as expression vectors for tumor, cancer, or infected cell-specific antigens.

BACKGROUND OF THE INVENTION

Current therapies for cancer include surgery, chemotherapy and radiation. The development and use of immunotherapeutic approaches, e.g., tumor targeting using antibody conjugates, "cancer vaccines", etc. is an attractive alternative, but has, to date, met with limited success for a number of reasons. The development of monoclonal antibodies specific for tumor antigens, for example, has proved difficult, in part, because antigens that are recognized by monoclonal antibodies and that are expressed by tumors and cancer cells are often also expressed by normal, non-cancerous cells. In addition, the expression of membrane antigens targeted by antibodies is frequently modulated to permit growth of tumor variants that do not express those antigens at the cell surface. A cell-mediated immune response may be more effective for eradication of tumors both because of the different array of effector functions that participate in such responses, and because T cell-mediated responses target not only membrane antigens but any tumor-specific intracellular protein that can be processed and presented in association with major histocompatibility molecules. It is, for this reason, much more difficult for a tumor to evade T cell-surveillance by modulating membrane expression.

Immunotherapeutic approaches based on cell-mediated immune responses are likely to be more effective, but antigens that are expressed by tumors and recognized in cell-mediated immune responses are difficult to identify and to produce. Development of an effective treatment for cancer through vaccination and subsequent stimulation of cell-mediated immunity, has remained elusive; the identification of effective antigens to stimulate cell-mediated responses has been successful only in special cases, such as melanoma. In melanoma, the cytotoxic T cells (CTLs) that mediate a cellular immune response against melanoma infiltrate the tumor itself, and such CTLs can be harvested from the tumor and used to screen for reactivity against other melanoma tumors. Isolation of tumor infiltrating lymphocytes has, however, not been a successful strategy to recover cytotoxic T cells specific for most other tumors, in particular the epithelial cell carcinomas that give rise to greater than 80% of human cancer.

To address the problem of identifying effective antigens for use in vaccination, most previous work has focused on screening expression libraries with tumor-specific CTLs to identify potential tumor antigens. There are significant limitations to the existing methods of identifying effective antigens, including the excessively laborious and inefficient screening process and the considerable difficulty in isolating tumor-specific CTLs for most types of tumors.

Cancer Vaccines

The possibility that altered features of a tumor cell are recognized by the immune system as non-self and may induce protective immunity is the basis for attempts to develop cancer vaccines. Whether or not this is a viable strategy depends on how the features of a transformed cell are altered. Appreciation of the central role of mutation in tumor transformation gave rise to the hypothesis that tumor antigens arise as a result of random mutation in genetically unstable cells. Although random mutations might prove immunogenic, it would be predicted that these would induce specific immunity unique for each tumor. This would be unfavorable for development of broadly effective tumor vaccines. An alternate hypothesis, however, is that a tumor antigen may arise as a result of systematic and reproducible tissue specific gene deregulation that is associated with the transformation process. This could give rise to qualitatively or quantitatively different expression of shared antigens in certain types of tumors that might be suitable targets for immunotherapy. Early results, demonstrating that the immunogenicity of some experimental tumors could be traced to random mutations (De Plaen, et al., *Proc. Natl. Acad. Sci. USA* 85:2274–2278 (1988); Srivastava, & Old, *Immunol. Today* 9:78 (1989)), clearly supported the first hypothesis. There is, however, no a priori reason why random mutation and systematic gene deregulation could not both give rise to new immunogenic expression in tumors. Indeed, more recent studies in both experimental tumors (Sahasrabudhe, et al.,*J. Immunology* 151:6202–6310 (1993); Torigoe, et al., *J. Immunol.* 147:3251 (1991)) and human melanoma (van Der Bruggen, e al., *Science* 254:1643–1647 (1991); Brichard, et al., J. Exp. Med. 178:489–495 (1993); Kawakami, et al., *Proc. Natl. Acad. Sci. USA* 91:3515–3519 (1994); Boel, et al., *Immunity* 2:167–175 (1995); Van den Eynde, et al.,*J. Exp. Med.* 182:689–698 (1995)) have clearly demonstrated expression of shared tumor antigens encoded by deregulated normal genes. The identification of MAGE-1 and other antigens common to different human melanoma holds great promise for the future development of multiple tumor vaccines.

In spite of the progress in melanoma, shared antigens recognized by cytotoxic T cells have not been described for other human tumors. The major challenge is technological. The most widespread and to date most successful approach to identify immunogenic molecules uniquely expressed in tumor cells is to screen a cDNA library with tumor-specific CTLs (cytotoxic T lymphocytes). Application of this strategy has led to identification of several gene families expressed predominantly in human melanoma. Two major limitations of this approach, however, are that (1) screening requires labor intensive transfection of numerous small pools of recombinant DNA into separate target populations in order to assay T cell stimulation by a minor component of some pool; and (2) with the possible exception of renal cell carcinoma, tumor-specific CTLs have been very difficult to isolate from either tumor infiltrating lymphocytes (TIL) or PBL of patients with other types of tumors, especially the epithelial cell carcinomas that comprise greater than 80% of human tumors. It appears that there may be tissue specific properties that result in tumor-specific CTLs being sequestered in melanoma.

Direct immunization with tumor-specific gene products may be essential to elicit an immune response against some shared tumor antigens. It has been argued that, if a tumor expressed strong antigens, it should have been eradicated prior to clinical manifestation. Perhaps then, tumors express only weak antigens. Immunologists have long been interested in the issue of what makes an antigen weak or strong. There have been two major hypotheses. Weak antigens may be poorly processed and fail to be presented effectively to T cells. Alternatively, the number of T cells in the organism with appropriate specificity might be inadequate for a vigorous response (a so-called "hole in the repertoire"). Elucidation of the complex cellular process whereby antigenic peptides associate with MHC molecules for transport to the cell surface and presentation to T cells has been one of the triumphs of modern immunology. These experiments have clearly established that failure of presentation due to processing defects or competition from other peptides could render a particular peptide less immunogenic. In contrast, it has, for technical reasons, been more difficult to establish that the frequency of clonal representation in the T cell repertoire is an important mechanism of low responsiveness. Recent studies demonstrating that the relationship between immunodominant and cryptic peptides of a protein antigen change in T cell receptor transgenic mice suggest, however, that the relative frequency of peptide-specific T cells can, indeed, be a determining factor in whether a particular peptide is cryptic or dominant in a T cell response. This has encouraging implications for development of vaccines. With present day methods, it would be a complex and difficult undertaking to modify the way in which antigenic peptides of a tumor are processed and presented to T cells. The relative frequency of a specific T cell population can, however, be directly and effectively increased by prior vaccination. This could, therefore, be the key manipulation required to render an otherwise cryptic response immunoprotective.

Another major concern for the development of broadly effective human vaccines is the extreme polymorphism of HLA class I molecules. Class I MHC:cellular peptide complexes are the target antigens for specific CD8+ CTLs. The cellular peptides, derived by degradation of endogenously synthesized proteins, are translocated into a pre-Golgi compartment where they bind to class I MHC molecules for transport to the cell surface. The CD8 molecule contributes to the avidity of the interaction between T cell and target by binding to the α3 domain of the class I heavy chain. Since all endogenous proteins turn over, peptides derived from any cytoplasmic or nuclear protein may bind to an MHC molecule and be transported for presentation at the cell surface. This allows T cells to survey a much larger representation of cellular proteins than antibodies which are restricted to recognize conformational determinants of only those proteins that are either secreted or integrated at the cell membrane.

The T cell receptor antigen binding site interacts with determinants of both the peptide and the surrounding MHC. T cell specificity must, therefore, be defined in terms of an MHC:peptide complex. The specificity of peptide binding to MHC molecules is very broad and of relatively low affinity in comparison to the antigen binding sites of specific antibodies. Class I-bound peptides are generally 8–10 residues in length and accommodate amino acid side chains of restricted diversity at certain key positions that match pockets in the MHC peptide binding site. These key features of peptides that bind to a particular MHC molecule constitute a peptide binding motif.

Hence, there exists a need for methods to facilitate the induction and isolation of T cells specific for human tumors, cancers and infected cells and for methods to efficiently select the genes that encode the major target antigens recognized by these T cells in the proper MHC-context.

Vaccinia Vectors

Poxvirus vectors are used extensively as expression vehicles for protein and antigen, e.g. vaccine antigen, expression in eukaryotic cells. Their ease of cloning and propagation in a variety of host cells has led, in particular, to the widespread use of poxvirus vectors for expression of foreign protein and as delivery vehicles for vaccine antigens (Moss, B.,*Science* 252:1662–1667 (1991)).

Customarily, the foreign DNA is introduced into the poxvirus genome by homologous recombination. The target protein coding sequence is cloned behind a vaccinia promoter flanked by sequences homologous to a non-essential region in the poxvirus and the plasmid intermediate is recombined into the viral genome by homologous recombination. This methodology works efficiently for relatively small inserts tolerated by prokaryotic hosts. The method becomes less viable in cases requiring large inserts as the frequency of homologous recombination is low and decreases with increasing insert size; in cases requiring construction of labor intensive plasmid intermediates such as in expression library production; and, in cases where the propagation of DNA is not tolerated in bacteria. Hence, there is a need for improved methods of introducing large inserts at high frequency, that do not require such labor intensive genetic engineering.

Alternative methods using direct ligation vectors have been developed to efficiently construct chimeric genomes in situations not readily amenable for homologous recombination (Merchlinsky, M. et al., *Virology* 190:522–526 (1992); Scheiflinger, F. et al., *Proc. Natl. Acad. Sci. USA*. 89:9977–9981 (1992)). These direct ligation protocols have obviated the need for homologous recombination to generate poxvirus chimeric genomes. In such protocols, the DNA from the genome was digested, ligated to insert DNA in vitro, and transfected into cells infected with a helper virus (Merchlinsky, M. et al., *Virology* 190:522–526 (1992); Scheiflinger, F. et al., *Proc. Natl. Acad. Sci. USA* 89:9977–9981 (1992)). In one protocol, the genome was digested at the unique NotI site and a DNA insert containing elements for selection or detection of the chimeric genomes was ligated to the genomic arms (Scheiflinger, F. et al.,*Proc. Natl. Acad. Sci. USA*. 89:9977–9981 (1992)). This direct ligation method was described for the insertion of foreign DNA into the vaccinia virus genome (Pfleiderer et al., *J. General Virology* 76:2957–2962 (1995)). Alternatively, the vaccinia WR genome was modified by removing the NotI site in the HindIII F fragment and reintroducing a NotI site proximal to the thymidine kinase gene such that insertion of a sequence at this locus disrupts the thymidine kinase gene, allowing isolation of chimeric genomes via use of drug selection (Merchlinsky, M. et al., *Virology* 190:522–526 (1992)).

The direct ligation vector, vNotI/tk allowed one to efficiently clone and propagate DNA inserts at least 26 kilobase pairs in length (Merchlinsky, M. et al., *Virology* 190:522–526 (1992)). Although, large DNA fragments were efficiently cloned into the genome, proteins encoded by the DNA insert will only be expressed at the low level corresponding to the thymidine kinase gene, a relatively weakly expressed early class gene in vaccinia. In addition, the DNA will be inserted in both orientations at the NotI site. Hence, there is a need for more efficient methods of cloning large DNA fragments into the viral genome with accompanying high levels of expression of the protein product encoded by the DNA insert. There also exists a need for improved direct ligation vectors. Such vectors will be more universally useful for the development of cancer vaccines.

SUMMARY OF THE INVENTION

The invention relates to methods for the identification of target antigens recognized by CTLs, and the formulation and use of such antigens in immunogenic compositions or vaccines to induce cell-mediated immunity against target cells, such as tumor cells, that express the target antigens.

Two basic approaches are described for the identification of target antigens. In one approach, CTLs generated against authentic target cells, such as tumor cells, in animals tolerized to non-target (e.g., non-tumorigenic) cellular counterparts are used to screen expression libraries made from target cell-derived (e.g., tumor-derived) DNA, RNA or cDNA to identify clones expressing target antigens. The CTLs generated by the methods described herein are not cross-reactive with normal cells, and thus are better tools for screening. Improved expression libraries are also described.

In a second approach for identifying target antigens, products of genes differentially expressed in target cells, such as tumor cells, are used to immunize animals to generate HLA-restricted CTLs which are evaluated for activity against authentic target cells. Like the first approach, this second strategy could also be particularly useful for identifying epitopes for many human tumor types where it has not been possible to generate tumor-specific CTLs directly from patients. In addition, it may identify cryptic antigens of the intact tumor cell—i.e., tumor cell products which can become immunogenic, if the representation of tumor-specific CTLs is first augmented by vaccination with that tumor cell product. Modified methods for differential display that improve resolution and reduce false positives are described.

In accordance with the present invention, the target cell is a cell to which it is desirable to induce a cell-mediated immune response. Examples of target cells in the body include, but are not limited to, tumor cells, malignant cells, transformed cells, cells infected with a virus, fungus, or mycobacteria, or cells subject to any other disease condition which leads to the production of target antigens.

The invention also encompasses the high yield expression of candidate target antigens, and production of recombinant viruses for vaccine formulation.

Abbreviations

CTLs—cytotoxic T lymphocytes (T cells)
PBL—peripheral blood lymphocytes
RDA—Representational Difference Analysis
TIL—tumor infiltrating lymphocytes

DESCRIPTION OF THE FIGURES

FIGS. 2A–2D Modifications in the nucleotide sequence of the p7.5/tk (SEQ ID NO:5) vaccinia transfer plasmid. Four new vectors, p7.5/ATG0/tk (SEQ ID NO:6), p7.5/ATG1/tk (SEQ ID NO:7), p7.5/ATG2/tk (SEQ ID NO:8) and p7.5/ATG3/tk (SEQ ID NO:9) have been derived as described in the text from the p7.5/tk vaccinia transfer plasmid. Each vector includes unique BamHI, SmaI, PstI, and SalI sites for cloning DNA inserts that employ either their own endogenous translation initiation site (in vector p7.5/ATG0/tk (SEQ ID NO:6)) or make use of a vector translation initiation site in any one of the three possible reading frames (p7.5/ATG1/tk (SEQ ID NO:7), p7.5/ATG2/tk (SEQ ID NO:8) and p7.5/ATG3/tk (SEQ ID NO:9)).

FIGS. 8A and 8B. Differential expression in tumor lines of differential display clone 90. RNase kinase protection assay: 300 picograms of clone 90 antisense probe was hybridized with 5 micrograms total RNA prior to RNase digestion and analysis of protected fragments on 5% denaturing PAGE.

DETAILED DESCRIPTION OF THE INVENTION

Figure 1:
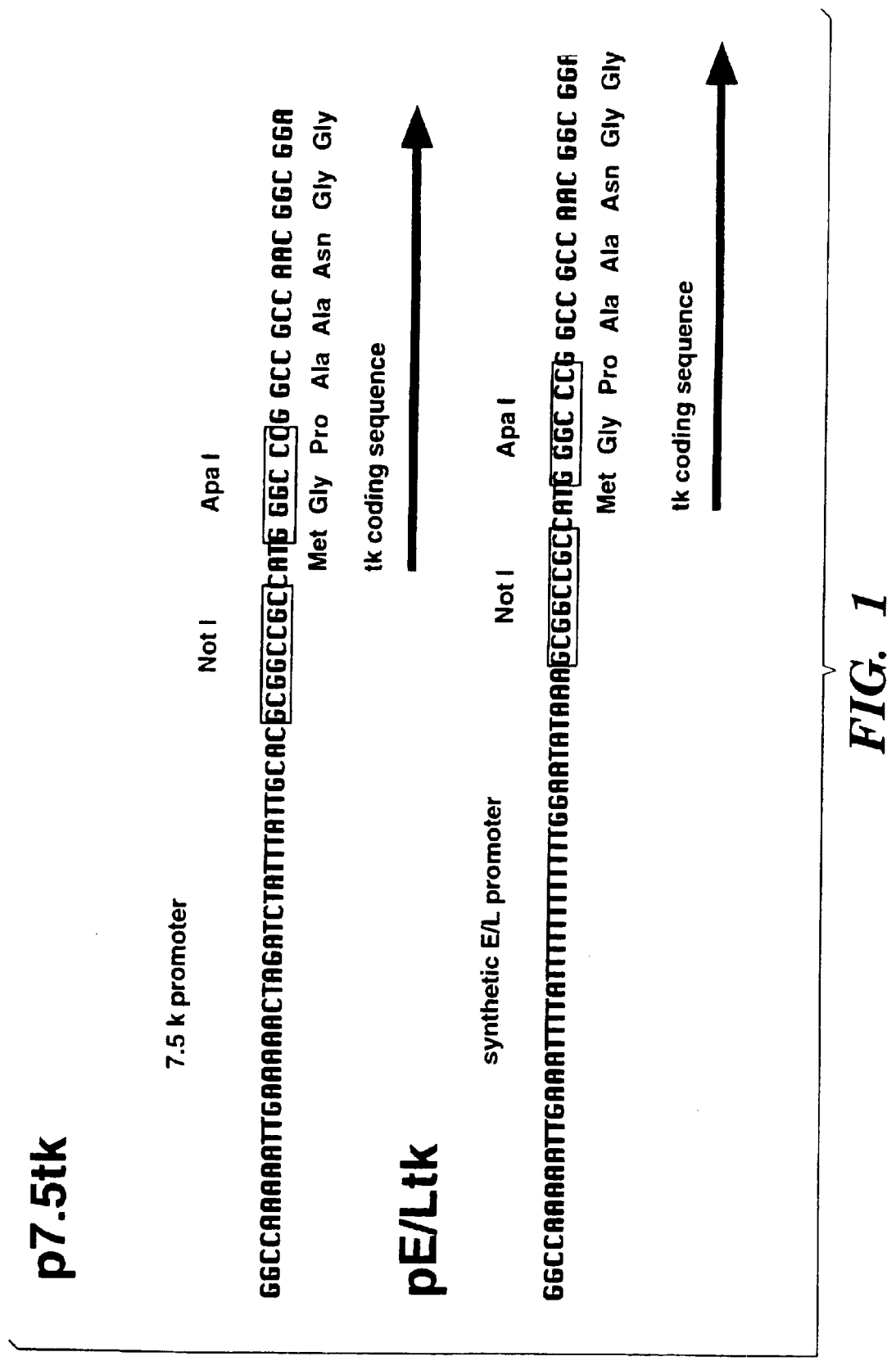
FIG. 1. Nucleotide Sequence of p7.5/tk (SEQ ID NO: 1) and pEL/tk (SEQ ID NO:3). The nucleotide sequence of the promoter and beginning of the thymidine kinase gene for v7.5/tk and vEL/tk.

The present invention relates to methods for the identification of target antigens recognized by CTLs, and the use of such antigens in immunogenic compositions or vaccines to induce a cell-mediated immune response against cells which express the target antigens.

In one embodiment of the invention, tumor-specific CTLs generated in animals are used to screen expression libraries generated from tumor cell DNA, RNA or cDNA to identify reactive target antigens. To this end, animals tolerized with a non-tumorigenic human cell line are immunized with tumor cells derived from the non-tumorigenic cell line. The resulting CTLs, which are tumor-specific and not cross-reactive with normal cells, can be used to screen expression libraries constructed from tumor-cell derived DNA, RNA or cDNA. Clones so identified in the library encode target antigens which are candidates for the immunogenic compositions and vaccines of the invention. Improved and modified vaccinia virus vectors for efficient construction of such DNA libraries using a "trimolecular recombination" approach are described to improve screening efficiency.

It is a preferred embodiment of the invention to tolerize animals, such as normal or transgenic mice, with normal human cells prior to immunizing with human tumor cells. Tolerance induction is preferred because the animal's immune response would otherwise be dominated by specificity for a large number of broadly expressed human proteins that are not specifically associated with tumor transformation. In a particularly preferred embodiment, and to enhance the efficiency of this approach, it is convenient to work with human tumors that are derived from an immortalized, non-tumorigenic human cell line by in vitro carcinogenesis or oncogene transformation. This provides a ready source of the normal control cells for an extended tolerization protocol in both neonatal and adult mice. For example, CTLs generated by this approach (see Example 2 below) can be employed in a selection procedure (such as that described in Example 3 below) to isolate recombinant clones that encode the target antigens from a tumor cDNA library, for example, such as that constructed in vaccinia virus by tri-molecular recombination (see Example 1 below).

In another embodiment of the invention, the products of genes that are differentially expressed in tumor cells are used to generate HLA-restricted CTLs which are evaluated for activity against authentic tumor cells. It is particularly preferred if methods such as Representational Difference Analysis (RDA) and differential display are employed to identify gene fragments that are differentially expressed in tumor versus normal cells. Conveniently, if it is determined that these gene products are broadly expressed in other related tumors (see, for example, Examples 5 and 6 below), they may be used to select longer clones from the library (see, for example, Example 4 below) which may be tested for the ability to induce a tumor-specific immune response in, for example, human CD8 and HLA transgenic mice (see, for example, Example 7). Gene products which generate tumor-specific cell mediated immunity are also candidates for the immunogenic compositions and vaccines of the invention. Improved methods for differential display are described that enhance screening efficiency by reducing false positives, and enhance the efficiency for isolating full length cDNAs.

The antigens identified using any of the foregoing strategies can be produced in quantity by recombinant DNA methods and formulated with an adjuvant that promotes a cell-mediated immune response. Preferably, the DNA encoding the target antigen is engineered into a recombinant virus that can be used to vaccinate animal hosts, including humans. In this regard, improved direct ligation vaccinia vectors are described that can be used to generate vaccines.

Another therapeutic strategy of the invention is to design vaccines that target a small set of HLA class I molecules which are expressed at elevated frequencies across ethnic populations. Extensive characterization of peptide binding motifs of different human class I MHC molecules has suggested that there are four major subtypes of HLA-A and HLA-B alleles (Sidney, J., et al., *Immunol. Today* 17:261–266 (1996)) such that many peptides will bind to multiple members of a single group. The present invention also provides methods to target vaccines for patients based on their membership in a class I MHC group. In specific embodiments, class I MHC subtypes A2, A3, B7 and B44 are targeted. Each group has an average representation across ethnic populations of between 40% and 50%. It is estimated that the combination of all four groups (which include 50% to 60% of all known HLA-A and HLA-B alleles) covers 95% of the human population. In a specific embodiment, HLA-A2.1, the most frequently expressed HLA allele in human populations (Caucasian 43%, Black 20%, Chinese 25%) and the dominant member of the A2 subtype, is targeted.

Although the methods of the invention described are used to identify reactive target antigens in tumor cells, the methods may also be used to identify target antigens in other target cells against which it is desirable to induce cell-mediated immunity. For example, the differential immunogenicity methods of the invention can be applied to identify immunogenic molecules of cells infected with virus, fungus or mycobacteria by tolerization of mice with uninfected cells followed by immunization with infected cells at different times after infection. The isolated CTLs can be employed to select recombinants that encode target antigens in a plasmid or viral expression library. An expression library can be constructed with cDNA isolated from the infected cell in a vaccinia virus vector using tri-molecular recombination.

A particular advantage of this approach is that it will identify potential antigens expressed not only by the pathogen but also by the host cell whose gene expression is altered as a result of infection. Since many pathogens elude immune surveillance by frequent reproduction and mutation, it may be of considerable value to develop a vaccine that targets host gene products that are not likely to be subject to mutation.

The differential gene expression strategies of the present invention may also be applied to identify immunogenic molecules of cells infected with virus, fungus or mycobacteria. More stable and/or previously unidentified antigens encoded by genes of either pathogen or host, including those which might remain cryptic without prior specific vaccination, may be identified.

Pathogens include, but are not limited to: viral pathogens, such as human immunodeficiency virus, Epstein Barr virus, hepatitis virus, herpes virus, human papillomavirus, cytomegalovirus, respiratory syncytial virus; fungal pathogens, such as *Candida albicans, pneumocystis carnii*; and mycobacterial pathogens, such as *M. tuberculosis, M. avium*.

The following details and examples mention primarily target antigens in tumor cells. As will be appreciated from the foregoing, the methods of the invention may be adapted to identify target antigens in other target cells, such as virally infected cells, and may be useful in developing vaccines.

Identifying Target Antigens for Use in Vaccines

The subsections below describe two strategies that can be used to identify target antigens or epitopes that are candidates for use in immunogenic formulations or vaccines. The two strategies described herein may be applied to identify target epitopes which include, but are not limited to, tumor specific, epitopes specific to a cell infected with a virus, fungus or mycobacteria, and/or epitopes specific to an autoimmune disease.

Induction of Cytotoxic T Lymphocytes Specific for Human Tumors and Their Use to Select DNA Recombinants that Encode Target Epitopes In this embodiment of the invention, cytotoxic T cells specific for human tumors are induced in animals which have been tolerized with a non-tumorigenic, immortalized normal human cell line that does not express costimulator activity. These animals are subsequently immunized with costimulator transfected (e.g., B7 transfected) tumor cells derived by in vitro mutagenesis or oncogene transformation from that same normal immortalized human cell line. An alternative source of matched normal and tumor cell pairs that could be employed in this same fashion is to derive normal and tumor cell lines from different tissue samples of the same patient. For purposes of immunization, costimulator activity could also be introduced in these tumor cells by transfection with murine B7. This immunization regimen gives rise to tumor-specific CTL that are not crossreactive on the homologous normal cells. The primary purpose of inducing tumor-specific CTL is that they can be employed, as described below, to select for clones of recombinant tumor DNA that encode the target antigen. Such antigens, because they are differentially immunogenic in tumor as compared to normal cells, are candidates for immunogenic formulations or vaccines. Mammals of different species, most commonly diverse strains of inbred mice, can be employed for this purpose. Whether a particular formulation or vaccine is immunogenic in any particular individual will depend on whether specific peptides derived from that antigen can be processed and presented in association with the particular MHC molecules expressed by that individual. To narrow the focus of this selection process to antigens from which peptides can be derived that associate with a particular human HLA molecule, it is possible, as described in Example 2, to derive directly HLA restricted CTL from HLA and human CD8 transgenic mice. Alternatively, differentially immunogenic molecules of the human tumor can be initially identified employing tumor-specific CTL restricted to any animal MHC. Antigens so identified can subsequently be characterized for the ability to be processed and presented in association with different human HLA types by primary in vitro stimulation of human peripheral blood lymphocytes (PBL), or, as described in Example 7, by immunization of HLA and human CD8 transgenic mice. The HLA transgene permits selection of a high affinity, HLA-restricted T cell repertoire in the mouse thymus. In addition, a human CD8 transgene is most preferable because murine CD8 does not interact efficiently with human class I MHC.

The method to determine differential immunogenicity can be carried out in normal mice if genes encoding mouse MHC molecules are introduced into the human cell lines by transfection (Kriegler, M., *Gene transfer and expression: A laboratory manual*, W. H. Freeman and Co., N.Y., (1991)). Alternatively, antigens of the human cell lines may be re-presented by murine professional antigen presenting cells in vivo (Huang, et al., *Science* 264:961–965 (1994)) and in vitro (Inaba, et al., *J. Exp. Med.* 176:1702 (1992); Inaba, et al., *J. Exp. Med.* 178:479488(1993)). To induce T cell tolerance during re-presentation of human antigens by murine dendritic cells it may be necessary to block costimulator activity with anti-B7.1 and anti-B7.2 antibodies. Specificity of the CTL generated in this way may be determined by comparing lysis of human tumor and normal target cells that have been transfected with HLA class I or that have been infected with HLA class I or that have been infected with HLA class I recombinant vaccinia virus.

Since immunogenicity of antigen in any individual depends on whether peptides derived from the antigen can be presented to T cells in association with MHC molecules of that particular individual, it may be separately determined by immunization of human volunteers or of human CD8 and HLA transgenic mice, which human HLA molecules are able to present peptides of any identified antigen. The two issues of immunogenicity and HLA associated presentation can be addressed simultaneously if HLA transgenic mice rather than normal mice are employed in the initial immunization.

The construction of transgenic mice is well known in the art and is described, for example, in Manipulating the Mouse Embryo: A laboratory Manual, Hogan, et al., Cold Spring Harbor Press, second edition, 1994. Human CD8 transgenic mice may be constructed by the method of LaFace, et al., *J. Exp. Med.* 182:1315–25 (1995). Construction of new lines of transgenic mice expressing the human CD8alpha and CD8beta subunits may be made by insertion of the corresponding human cDNA into a human CD2 minigene based vector for T cell-specific expression in transgenic mice (Zhumabekov, et al., *J. Immunol. Methods* 185:133–140 (1995)). HLA class I transgenic mice may be constructed by the methods of Chamberlain, et al., *Proc. Natl. Acad. Sci. USA* 85:7690–7694 (1988) or Bernhard, et al., *J. Exp. Med.* 168: 1157–62(1988) or Vitiello, et al., *J. Exp. Med.* 173: 1007–1015 (1991) or Barra, et al., *J. Immunol.* 150: 3681–9 (1993).

Construction of additional HLA class I transgenic mice may be achieved by construction of an H-2Kb cassette that includes 2 kb of upstream regulatory region together with the first two introns previously implicated in gene regulation (Kralova, et al., *EMBO J.* 11:4591–4600 (1992)). Endogenous translational start sites are eliminated from this region and restriction sites for insertion of HLA cDNA are introduced into the third exon followed by a polyA addition site. By including an additional 3kb of genomic H-2Kb sequence at the 3' end of this construct, the class I gene can be targeted for homologous recombination at the H-2Kb locus in embryonic stem cells. This has the advantage that the transgene is likely to be expressed at a defined locus known to be compatible with murine class I expression and that these mice are likely to be deficient for possible competition by H-2Kb expression at the cell membrane. It is believed that this will give relatively reproducible expression of diverse human HLA class I cDNA introduced in the same construct.

Most preferably, the tumor cell lines are a panel of tumor cell lines that are all derived from a single immortalized, non-tumorigenic cell line. Non-tumorigenic cells are most preferable for inducing tolerance to the large number of normal human proteins that are also expressed in tumor cells.

Preferably, screening is performed on such a panel of tumor cell lines, independently derived from the same normal cells by diverse carcinogens or oncogene transformation. Screening of such a panel of tumor cell lines makes it possible to filter out antigenic changes that are carcinogen specific or that may arise by random genetic drift during in vitro propagation of a tumor cell line.

The tumor-specific CTLs generated as described above can be used to screen expression libraries prepared from the target tumor cells in order to identify clones encoding the target epitope. DNA libraries constructed in a viral vector infectious for mammalian cells as described herein can be employed for the efficient selection of specific recombinants by CTLs. Major advantages of these infectious viral vectors are 1) the ease and efficiency with which recombinants can be introduced and expressed in mammalian cells, and 2) efficient processing and presentation of recombinant gene products in association with MHC molecules of the infected cell. At a low multiplicity of infection (m.o.i.), many target cells will express a single recombinant which is amplified within a few hours during the natural course of infection.

In one embodiment of the invention, a representative DNA library is constructed in vaccinia virus. Preferably, a tri-molecular recombination method employing modified vaccinia virus vectors and related transfer plasmids is used to construct the representative DNA library in vaccinia virus. This method generates close to 100% recombinant vaccinia virus (see Example 1).

In a preferred embodiment (see also Example 9), a vaccinia virus transfer plasmid pJ/K, a pUC 13 derived plasmid with a vaccinia virus thymidine kinase gene containing an in-frame Not I site, is further modified to incorporate one of two strong vaccinia virus promoters, e.g., either a 7.5K vaccinia virus promoter or a strong synthetic early/late (E/L) promoter, followed by Not I and Apa I restriction sites. The Apa I site is preferably preceded by a strong translational initiation sequence including the ATG codon. This modification is preferably introduced within the vaccinia virus thymidine kinase (tk) gene so that it is flanked by regulatory and coding sequences of the viral tk gene. Each of the two modifications within the tk gene of a plasmid vector may be transferred by homologous recombination in the flanking tk sequences into the genome of the Vaccinia Virus WR strain derived vNotI$^-$ vector to generate two new viral vectors. Importantly, following Not I and Apa I restriction endonuclease digestion of these two viral vectors, two large viral DNA fragments can be isolated each including a separate non-homologous segment of the vaccinia tk gene and together comprising all the genes required for assembly of infectious viral particles.

In one embodiment, such modifications are introduced in the Modified Virus Ankara (MVA) strain of vaccinia, which is replication deficient in mammalian cells (Meyer, et al., *J. Gen. Virol.* 72:1031–1038(1991)).

In a preferred embodiment, the following method is used to enrich for, and select for those cells infected with the recombinant viruses that express the target epitopes of specific cytotoxic T cells. An adherent monolayer of cells i s infected with a recombinant viral library, e.g. a vaccinia recombinant viral library, at m.o.i. less than or equal to 1. It is important that these cells do not themselves express the target epitopes recognized by specific CTLs but that these epitopes are represented in the viral library. In addition, for selection by CTLs, the infected cells must express an appropriate MHC molecule that can associate with and present the target peptide to T cells.

After 12 hours infection with recombinant virus, the monolayer is washed to remove any non-adherent cells. CTLs of defined specificity are added for 30 min. During this time, some of the adherent cells infected with a recombinant particle that leads to expression of the target epitope will interact with a specific CTL and undergo a lytic event. Cells that under go a lytic event are released from the monolayer and can be harvested in the floating cell population. The above-described protocol is repeated for preferably five or more cycles, to increase the level of enrichment obtained by this procedure.

Screening Cytotoxic Lymphocytes Generated Against Products of Genes Differentially Expressed in Tumor Cells for Activity Against Authentic Tumor Cells In this embodiment of the invention, the products of genes that are differentially expressed in a tumor are used to generate HLA-restricted CTLs (e.g., by immunization of transgenic animals or in vitro stimulation of human PBL with antigen presenting cells that express the appropriate MHC). The CTLs so generated are assayed for activity against authentic tumor cells in order to identify the differentially expressed gene which encodes the effective target epitope.

In essence, this approach to identify tumor-specific antigens is the reverse of the strategy described in the preceding section. Rather than isolating CTLs generated against authentic tumor cells to screen expression libraries of tumor-specific cDNA, the tumor-specific cDNA or gene products (i.e., the product of genes differentially expressed in tumors) are used to generate CTLs which are then screened using authentic tumor. This strategy is quite advantageously used to identify target epitopes for many human tumor types where it has not been possible to generate tumor-specific CTL directly from patients. This strategy provides an additional advantage in that cryptic tumor antigens can be identified. Rather than only assaying for what is immunogenic on a tumor cell, this embodiment of the invention allows for the evaluation and assessment of tumor cell products that can become immunogenic if the representation of tumor-specific T cells is first augmented by vaccination.

Differentially expressed genes derived from the tumor can be identified using standard techniques well known to those skilled in the art (e.g., see Liang & Pardee, *Science* 257:967–971 (1992)), which is incorporated by reference herein in its entirety). Preferably, the improved differential display methods described in Example 4, infra, may be used to reduce false positives and enhance the efficiency for isolating full length cDNAs corresponding to the identified DNA fragments. Each differentially expressed gene product is potentially immunogenic, and may be represented as a low-abundance or high abundance transcript.

In order to identify the differentially expressed gene products that might be candidates for tumor immunotherapy, it is necessary to have a means of delivering the product for immunization in an environment in which T cell responses to peptides associated with human HLA can be induced. To this end, the differentially expressed cDNA is incorporated into an expression vector, preferably a viral vector (such as the vaccinia vectors described herein) so that quantities of the gene product adequate for immunization are produced. Immunization can be accomplished using the recombinantly expressed gene product formulated in a subunit vaccine (e.g., mixed with a suitable adjuvant that can promote a cell mediated immune response). Preferably a recombinant viral expression vector, such as vaccinia, can be used to immunize (Bennock & Yewdell, *Current Topics In Microbiol. and Immunol.* 163:153–178 (1990)). Most preferably, transgenic mice are employed which express a human class I MHC molecule, so that HLA-restricted murine cytotoxic T cells specific for the gene product can be induced and isolated (Shirai, M., et al., J. Immunol. 154:273342 (1995); Wentworth et al., *Eur. J. of Immunol.* 26:97–101(1996)). Alternatively, human PBL are stimulated in vitro with antigen presenting cells that express homologous HLA.

The significance of HLA compatibility is that T cells recognize peptides that bind to, and are transported to the surface of antigen presenting cells in association with major histocompatibility molecules. T cells of HLA transgenic mice are, therefore, primed to recognize a specific peptide in association with the expressed human HLA and crossreactivity with human tumor cells depends on expression of that same tumor peptide in association with the same HLA molecule.

The CTLs induced by the immunization can be tested for cross reactivity on HLA compatible tumors that express the corresponding mRNA. The CTLs can be assayed for their ability to kill authentic tumor cells in vitro or in vivo. To this end, assays described in Example 2 can be used, or other similar assays for determining tumor cell specificity and killing which are well known to those skilled in the art.

Using this approach, target epitopes which are particularly good candidates for tumor immunotherapy in human patients are identified as those which meet the following criteria: (a) the gene is differentially expressed in multiple human tumors; (b) the gene products are immunogenic in association with HLA; and (c) the specific CTLs induced are cross reactive on human tumor cells.

Vaccine Formulations

The present invention encompasses the expression of the identified target epitope in either eucaryotic or procaryotic recombinant expression vectors; and the formulation of the identified epitope as immunogenic and/or antigenic compositions. In accordance with the present invention, the recombinantly expressed target epitope may be expressed, purified and formulated as a subunit vaccine. The identified target epitope may also be constructed into viral vectors for use in vaccines. In this regard, either a live recombinant viral vaccine, an inactivated recombinant viral vaccine, or a killed recombinant viral vaccine can be formulated.

Expression of the Target Epitope in Procaryotic and Eucaryotic Expression Systems The present invention encompasses expression systems, both eucaryotic and procaryotic expression vectors, which may be used to express the identified target epitopc. The identified epitope may be expressed in both truncated or full-length forms of the epitope, in particular for the formation of subunit vaccines.

The present invention encompasses the expression of nucleotide sequences encoding the identified epitopes and immunologically equivalent fragments. Such immunologically equivalent fragments may be identified by making analogs of the nucleotide sequence encoding the identified epitopes that are truncated at the 5' and/or 3' ends of the sequence and/or have one or more internal deletions, expressing the analog nucleotide sequences, and determining whether the resulting fragments immunologically are recognized by the epitope specific CTLs and induce a cell-mediated immune response.

The invention encompasses the DNA expression vectors that contain any of the foregoing coding sequences operatively associated with a regulatory element that directs expression of the coding sequences and genetically engineered host cells that contain any of the foregoing coding sequences operatively associated with a regulatory element that directs the expression of the coding sequences in the host cell. As used herein, regulatory elements include but are not limited to, inducible and non-inducible promoters, enhancers, operators and other elements known to those skilled in the art that drive and regulate expression.

The target epitope gene products or peptide fragments thereof, may be produced by recombinant DNA technology using techniques well known in the art. Thus, methods for preparing the epitope gene polypeptides and peptides of the invention by expressing nucleic acid containing epitope gene sequences are described herein. Methods which are well known to those skilled in the art can be used to construct expression vectors containing epitope gene product coding sequences and appropriate transcriptional and translational control signals. These methods include, for example, in vitro recombinant DNA techniques, synthetic techniques, and in vivo genetic recombination. See, for example, the techniques described in Sambrook et al., 1989, supra, and Ausubel et al., 1989, supra. Alternatively, RNA capable of encoding glycoprotein epitope gene product sequences may be chemically synthesized using, for example, synthesizers. See, for example, the techniques described in "Oligonucleotide Synthesis", 1984, Gait, M. J. ed., IRL Press, Oxford, which is incorporated by reference herein in its entirety.

The invention also encompasses nucleotide sequences that encode peptide fragments of the identified epitope gene products. For example, polypeptides or peptides corresponding to the extracellular domain of the selected epitope may be useful as "soluble" protein which would facilitate secretion, particularly useful in the production of subunit vaccines. The selected epitope gene product or peptide fragments thereof, can be linked to a heterologous epitope that is recognized by a commercially available antibody is also included in the invention. A durable fusion protein may also be engineered; i.e., a fusion protein which has a cleavage site located between the selected epitope sequence and the heterologous protein sequence, so that the selected epitope can be cleaved away from the heterologous moiety. For example, a collagenase cleavage recognition consensus sequence may be engineered between the selected epitope protein or peptide and the heterologous peptide or protein. The epitopic domain can be released from this fusion protein by treatment with collagenase. In a preferred embodiment of the invention, a fusion protein of glutathione-S-transferase and the selected epitope protein may be engineered.

The selected epitope proteins of the present invention for use in vaccine preparations, in particular subunit vaccine preparations, are substantially pure or homogeneous. The protein is considered substantially pure or homogeneous when at least 60 to 75% of the sample exhibits a single polypeptide sequence. A substantially pure protein will preferably comprise 60 to 90% of a protein sample, more preferably about 95% and most preferably 99%. Methods which are well known to those skilled in the art can be used to determine protein purity or homogeneity, such as polyacrylamide gel electrophoresis of a sample, followed by visualizing a single polypeptide band on a staining gel. Higher resolution may be determined using HPLC or other similar methods well known in the art.

The present invention encompasses polypeptides which are typically purified from host cells expressing recombinant nucleotide sequences encoding these proteins. Such protein purification can be accomplished by a variety of methods well known in the art. In a preferred embodiment, the epitope protein of the present invention is expressed as a fusion protein with glutathione-S-transferase. The resulting recombinant fusion proteins purified by affinity chromatography and the epitope protein domain is cleaved away from the heterologous moiety resulting in a substantially pure protein sample. Other methods known to those skilled in the art may be used; see for example, the techniques described in "Methods In Enzymology", 1990, Academic Press, Inc., San Diego, "Protein Purification: Principles and Practice", 1982, Springer-Verlag, New York, which are incorporated by reference herein in their entirety.

Eucaryotic and Procaryotic Expression Vectors

The present invention encompasses expression systems, both eucaryotic and procaryotic expression vectors, which may be used to express the selected epitope. A variety of host-expression vector systems may be utilized to express the selected target epitope gene of the invention. Such host-expression systems represent vehicles by which the coding sequences of interest may be produced and subsequently purified, but also represent cells which may, when transformed or transfected with the appropriate nucleotide coding sequences, exhibit the selected epitope gene product of the invention in situ. These include but are not limited to microorganisms such as bacteria (e.g., *E. coli, B. subtilis*) transformed with recombinant bacteriophage DNA, plasmid DNA or cosmid DNA expression vectors containing selected epitope gene product coding sequences; yeast (e.g., Saccharomyces, Pichia) transformed with recombinant yeast expression vectors containing the selected epitope gene product coding sequences; insect cell systems infected with recombinant virus expression vectors (e.g., baculovirus) containing the selected epitope gene product coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing selected epitope gene product coding sequences; or mammalian cell systems (e.g., COS, CHO, BHK, 293, 3T3) harboring recombinant expression constructs containing promoters derived from the genome of mammalian cells (e.g., metallothionein promoter) or from mammalian viruses (e.g., the adenovirus late promoter; the vaccinia virus 7.5K promoter).

Host Cells

The present invention encompasses the expression of the selected epitope in animal and insect cell lines. In a preferred embodiment of the present invention, the selected epitope is expressed in a baculovirus vector in an insect cell line to produce an unglycosylated antigen. In another preferred embodiment of the invention, the selected epitope is expressed in a stably transfected mammalian host cell, e.g., T lymphocyte cell line to produce a glycosylated antigen. The selected epitopes which are expressed recombinantly by these cell lines may be formulated as subunit vaccines.

A host cell strain may be chosen which modulates the expression of the inserted sequences, or modifies and processes the gene product in the specific fashion desired. Such modifications (e.g., glycosylation) and processing (e.g. cleavage) of protein products may be important for the function of the protein. Different host cells have characteristic and specific mechanisms for the post-translational processing and modification of proteins and gene products. Appropriate cell lines or host systems can be chosen to ensure the correct modification of the foreign protein expressed. To this end, eucaryotic host cells which possess the cellular machinery for proper processing of the primary transcript, glycosylation, and phosphorylation of the gene product may be used. Such mammalian host cells include but are not limited to CHO, VERO, BHK, HeLa, COS, MDCK, 293, 3T3 and WI38 cell lines.

For long term, high-yield production of recombinant proteins, stable expression is preferred. For example, cell lines which stably express the selected target epitope may be engineered. Rather than using expression vectors which contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells may be allowed to grow for 1–2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines. This method may advantageously be used to engineer cell lines which express the selected epitope gene products. Such cell lines would be particularly useful in screening and evaluation of compounds that affect the endogenous activity of the selected epitope gene product.

A number of selection systems may be used, including but not limited to the herpes simplex virus thymidine kinase (Wigler, et al., *Cell* 11:223 (1977)), hypoxanthine-guanine phosphoribosyltransferase (Szybalska & Szybalski, *Proc. Natl. Acad. Sci. USA* 48:2026 (1962)), and adenine phosphoribosyltransferase (Lowy, et al., *Cell* 22:817 (1980)) genes can be employed in tk$^-$, hgprt$^-$ or aprt$^-$ cells, respectively. Also, antimetabolite resistance can be used as the basis of selection for the following genes: dhfr, which confers resistance to methotrexate (Wigler, et al., *Natl. Acad. Sci. USA* 77:3567 (1980); O'Hare, et al., *Proc. Natl. Acad. Sci. USA* 78:1527 (1981)); gpt, which confers resistance to mycophenolic acid (Mulligan & Berg, *Proc. Natl. Acad. Sci. USA* 78:2072 (1981)); neo, which confers resistance to the aminoglycoside G-418 (Colberre-Garapin, et al., *J. Mol. Biol.* 150:1 (1981)); and hygro, which confers resistance to hygromycin (Santerre, et al., *Gene* 30:147 (1984)).

Alternatively, any fusion protein may be readily purified by utilizing an antibody specific for the fusion protein being expressed. For example, a system described by Janknecht et al. allows for the ready purification of non-denatured fusion proteins expressed in human cell lines (Janknecht, et al., *Proc. Natl. Acad. Sci. USA* 88: 8972–8976 (1991)). In this system, the gene of interest is subcloned into a vaccinia recombination plasmid such that the gene's open reading frame is translationally fused to an amino-terminal tag consisting of six histidine residues. Extracts from cells infected with recombinant vaccinia virus are loaded onto Ni$^{2+}$.nitriloacetic acid-agarose columns and histidine-tagged proteins are selectively eluted with imidazole-containing buffers.

Expression of Target Epitope in Recombinant Viral Vaccines

In another embodiment of the present invention, either a live recombinant viral vaccine or an inactivated recombinant viral vaccine expressing the selected target epitope can be engineered. A live vaccine may be preferred because multiplication in the host leads to a prolonged stimulus of similar kind and magnitude to that occurring in natural infections, and therefore, confers substantial, long-lasting immunity. Production of such live recombinant virus vaccine formulations may be accomplished using conventional methods involving propagation of the virus in cell culture or in the allantois of the chick embryo followed by purification.

In this regard, a variety of viruses may be genetically engineered to express the selected epitope. For vaccine purposes, it may be required that the recombinant viruses display attenuation characteristics. Current live virus vaccine candidates for use in humans are either cold adapted, temperature sensitive, or attenuated. The introduction of appropriate mutations (e.g., deletions) into the templates used for transfection may provide the novel viruses with attenuation characteristics. For example, specific multiple missense mutations that are associated with temperature sensitivity or cold adaptation can be made into deletion mutations and/or multiple mutations can be introduced into individual viral genes. These mutants should be more stable than the cold or temperature sensitive mutants containing single point mutations and reversion frequencies should be extremely low. Alternatively, recombinant viruses with "suicide" characteristics may be constructed. Such viruses go through only one or a few rounds of replication in the host.

For purposes of the invention, any virus may be used in accordance with the present invention which: (a) displays an attenuated phenotype or may be engineered to display attenuated characteristics; (b) displays a tropism for mammals, in particular humans, or may be engineered to display such a tropism; and (c) may be engineered to express the selected target epitope of the present invention.

Vaccinia viral vectors may be used in accordance with the present invention, as large fragments of DNA are easily cloned into its genome and recombinant attenuated vaccinia variants have been described (Meyer, et al., *J. Gen. Virol.* 72:1031–1038 (1991)). Orthomyxoviruses, including influenza; Paramyxoviruses, including respiratory syncytial virus and Sendai virus; and Rhabdoviruses may be engineered to express mutations which result in attenuated phenotypes (see U.S. Pat. No. 5,578,473, issued Nov. 26, 1996). These viral genomes may also be engineered to express foreign nucleotide sequences, such as the selected epitopes of the present invention (see U.S. Pat. No. 5,166,057, issued Nov. 24, 1992, incorporated herein by reference in its entirety). Reverse genetic techniques can be applied to manipulate negative and positive strand RNA viral genomes to introduce mutations which result in attenuated phenotypes, as demonstrated in influenza virus, Herpes Simplex virus, cytomegalovirus and Epstein-Barr virus, Sindbis virus and poliovirus (see Palese et al., *Proc. Natl. Acad. Sci. USA* 93:11354–11358 (1996)). These techniques may also be utilized to introduce foreign DNA, i.e., the selected target epitopes, to create recombinant viral vectors to be used as vaccines in accordance with the present invention. In addition, attenuated adenoviruses and retroviruses may be engineered to express the target epitope. Therefore, a wide variety of viruses may be engineered to design the vaccines of the present invention, however, by way of example, and not by limitation, recombinant attenuated vaccinia vectors expressing the selected target epitope for use as vaccines are described herein.

In one embodiment, a recombinant modified vaccinia variant, Modified Virus Ankara (MVA) is used in a vaccine formulation. This modified virus has been passaged for 500 cycles in avian cells and is unable to undergo a full infectious cycle in mammalian cells (Meyer, et al., *J. Gen. Virol.* 72:1031–1038 (1991)). When used as a vaccine, the recombinant virus goes through a single replication cycle and induces a sufficient level of immune response but does not go further in the human host and cause disease. Recombinant viruses lacking one or more of essential vaccinia virus genes are not able to undergo successive rounds of replication. Such defective viruses can be produced by co-transfecting vaccinia vectors lacking a specific gene(s) required for viral replication into cell lines which permanently express this gene(s). Viruses lacking an essential gene(s) will be replicated in these cell lines but when administered to the human host will not be able to complete a round of replication. Such preparations may transcribe and translate—in this abortive cycle—a sufficient number of genes to induce an immune response.

Alternatively, larger quantities of the strains can be administered, so that these preparations serve as inactivated (killed) virus, vaccines. For inactivated vaccines, it is preferred that the heterologous gene product be expressed as a viral component, so that the gene product is associated with the virion. The advantage of such preparations is that they contain native proteins and do not undergo inactivation by treatment with formalin or other agents used in the manufacturing of killed virus vaccines.

In another embodiment of the invention, inactivated vaccine formulations are prepared using conventional techniques to "kill" the recombinant viruses. Inactivated vaccines are "dead" in the sense that their infectivity has been destroyed. Ideally, the infectivity of the virus is destroyed without affecting immunogenicity. In order to prepare inactivated vaccines, the recombinant virus may be grown in cell culture or in the allantois of the chick embryo, purified by zonal ultracentrifugation, inactivated by formaldehyde or β-propiolactone, and pooled. The resulting vaccine is usually inoculated intramuscularly.

Inactivated viruses may be formulated with a suitable adjuvant in order to enhance the immunological response. Such adjuvants may include but are not limited to mineral gels, e.g., aluminum hydroxide; surface active substances such as lysolecithin, pluronic polyols, polyanions; peptides; oil emulsions; and potentially useful human adjuvants such as BCG and *Corynebacterium parvum*.

Methods of Treatment and/or Vaccination

Since the identified target epitopes of the present invention can be produced in large amounts, the antigen thus produced and purified has use in vaccine preparations. The target epitope may be formulated into a subunit vaccine preparation, or may be engineered into viral vectors and formulated into vaccine preparations. Alternatively, the DNA encoding the target epitope may be administered directly as a vaccine formulation. The "naked" plasmid DNA once administered to a subject invades cells, is expressed on the surface of the invaded cell and elicits a cellular immune response, so that T lymphocytes will attack cells displaying the selected epitope. The selected epitope also has utility in diagnostics, e.g., to detect or measure in a sample of body fluid from a subject the presence of tumors and thus to diagnose cancer and tumors and/or to monitor the cellular immune response of the subject subsequent to vaccination.

The recombinant viruses of the invention can be used to treat tumor-bearing mammals, including humans, to generate an immune response against the tumor cells. The generation of an adequate and appropriate immune response leads to tumor regression in vivo. Such "vaccines" can be used either alone or in combination with other therapeutic regimens, including but not limited to chemotherapy, radiation therapy, surgery, bone marrow transplantation, etc. for the treatment of tumors. For example, surgical or radiation techniques could be used to debulk the tumor mass, after which, the vaccine formulations of the invention can be administered to ensure the regression and prevent the progression of remaining tumor masses or micrometastases in the body. Alternatively, administration of the "vaccine" can precede such surgical, radiation or chemotherapeutic treatment.

Alternatively, the recombinant viruses of the invention can be used to immunize or "vaccinate" tumor-free subjects to prevent tumor formation. With the advent of genetic testing, it is now possible to predict a subject's predisposition for cancers. Such subjects, therefore, may be immunized using a recombinant vaccinia virus expressing an appropriate tumor-associated antigen.

The immunopotency of the epitope vaccine formulations antigen can be determined by monitoring the immune response in test animals following immunization or by use of any immunoassay known in the art. Generation of a cell-mediated immune response may be taken as an indication of an immune response. Test animals may include mice, hamsters, dogs, cats, monkeys, rabbits, chimpanzees, etc., and eventually human subjects.

Suitable preparations of such vaccines include injectables, either as liquid solutions or suspensions; solid forms suitable for solution in, suspension in, liquid prior to injection, may also be prepared. The preparation may also be emulsified, or the polypeptides encapsulated in liposomes. The active immunogenic ingredients are often mixed with excipients which are pharmaceutically acceptable and compatible with the active ingredient. Suitable excipients are, for example, water, saline, dextrose, glycerol, ethanol, or the like and combinations thereof. In addition, if desired, the vaccine preparation may also include minor amounts of auxiliary substances such as wetting or emulsifying agents, pH buffering agents, and/or adjuvants which enhance the effectiveness of the vaccine.

Examples of adjuvants which may be effective, include, but are not limited to: aluminum hydroxide, N-acetyl-muramyl-L-threonyl-D-isoglutamine (thr-MDP), N-acetyl-nor-muramyl-L-alanyl-D-isoglutamine, N-acetylmuramyl-L-alanyl-D-isoglutaminyl-L-alanine-2-(1'-2'-dipalmitoyl-sn-glycero-3-hydroxyphosphoryloxy)-ethylamine, GM-CSF, QS-21 (investigational drug, Progenics Pharmaceuticals, Inc.), DETOX (investigational drug, Ribi Pharmaceuticals), and BCG.

The effectiveness of an adjuvant may be determined by measuring the induction of the cellular immune response directed against the target epitope.

The vaccines of the invention may be multivalent or univalent. Multivalent vaccines are made from recombinant viruses that direct the expression of more than one antigen.

The composition, if desired, can also contain minor amounts of wetting or emulsifying agents, or pH buffering agents. The composition can be a liquid solution, suspension, emulsion, tablet, pill, capsule, sustained release formulation, or powder. Oral formulation can include standard carriers such as pharmaceutical grades of mannitol, lactose, starch, magnesium stearate, sodium saccharine, cellulose, magnesium carbonate, etc.

Generally, the ingredients are supplied either separately or mixed together in unit dosage form, for example, as a dry lyophilized powder or water free concentrate in a hermetically sealed container such as an ampoule or sachette indicating the quantity of active agent. Where the composition is administered by injection, an ampoule of sterile diluent can be provided so that the ingredients may be mixed prior to administration.

In a specific embodiment, a lyophilized epitope of the invention is provided in a first container; a second container comprises diluent consisting of an aqueous solution of 50% glycerin, 0.25% phenol, and an antiseptic (e.g., 0.005% brilliant green).

Use of purified antigens as vaccine preparations can be carried out by standard methods. For example, the purified protein(s) should be adjusted to an appropriate concentration, formulated with any suitable vaccine adjuvant and packaged for use. Suitable adjuvants may include, but are not limited to: mineral gels, e.g., aluminum hydroxide; surface active substances such as lysolecithin, pluronic polyols; polyanions; peptides; oil emulsions; alum, and MDP. The immunogen may also be incorporated into liposomes, or conjugated to polysaccharides and/or other polymers for use in a vaccine formulation. In instances where the recombinant antigen is a hapten, i.e., a molecule that is antigenic in that it can react selectively with cognate antibodies, but not immunogenic in that it cannot elicit an immune response, the hapten may be covalently bound to a carrier or immunogenic molecule; for instance, a large protein such as serum albumin will confer immunogenicity to the hapten coupled to it. The hapten-carrier may be formulated for use as a vaccine.

Many methods may be used to introduce the vaccine formulations described above into a patient. These include, but are not limited to, oral, intradermal, intramuscular, intraperitoneal, intravenous, subcutaneous, intranasal, transdermal, epidural, pulmonary, gastric, intestinal, rectal, vaginal, or urethral routes. When the method of treatment uses a live recombinant vaccinia vaccine formulation of the invention, it may be preferable to introduce the formulation via the natural route of infection of the vaccinia virus, i.e., through a mucosal membrane or surface, such as an oral, nasal, gastric, intestinal, rectal, vaginal or urethral route. To induce a CTL response, the mucosal route of administration may be through an oral or nasal membrane. Alternatively, an intramuscular or intraperitoneal route of administration may be used. Preferably, a dose of $10^6-10^7$ PFU (plaque forming units) of cold adapted recombinant vaccinia virus is given to a human patient.

The precise dose of vaccine preparation to be employed in the formulation will also depend on the route of administration, and the nature of the patient, and should be decided according to the judgment of the practitioner and each patient's circumstances according to standard clinical techniques. An effective immunizing amount is that amount sufficient to produce an immune response to the antigen in the host to which the vaccine preparation is administered.

Where subsequent or booster doses are required, a modified vaccinia virus such as MVA can be selected as the parental virus used to generate the recombinant. Alternatively, another virus, e.g., adenovirus, canary pox virus, or a subunit preparation can be used to boost. Immunization and/or cancer immunotherapy may be accomplished using a combined immunization regimen, e.g., immunization with a recombinant vaccinia viral vaccine of the invention and a boost of a recombinant vaccinia viral vaccine. In such an embodiment, a strong secondary $CD8^+$ T cell response is induced after priming and boosting with different viruses expressing the same epitope (for such methods of immunization and boosting, see, e.g., Murata et al., *Cellular Immunol.* 173:96–107). For example, a patient is first primed with a vaccine formulation of the invention comprising a recombinant vaccinia virus expressing an epitope, e.g., a selected tumor-associated antigen or fragment thereof. The patient is then boosted, e.g., 21 days later, with a vaccine formulation comprising a recombinant virus other than vaccinia expressing the same epitope. Such priming followed by boosting induces a strong secondary $CD8^+$ T cell response. Such a priming and boosting immunization regimen is preferably used to treat a patient with a tumor, metastasis or neoplastic growth expressing the selected tumor-associated antigen.

In yet another embodiment, the recombinant vaccinia viruses can be used as a booster immunization subsequent to a primary immunization with inactivated tumor cells, a subunit vaccine containing the tumor-associated antigen or its epitope, or another recombinant viral vaccine, e.g., adenovirus, canary pox virus, or MVA.

In an alternate embodiment, recombinant vaccinia virus encoding a particular tumor-associated antigen, epitope or fragment thereof may be used in adoptive immunotherapeutic methods for the activation of T lymphocytes that are histocompatible with the patient and specific for the tumor-associated antigen (for methods of adoptive immunotherapy, see, e.g., Rosenberg, U.S. Pat. No. 4,690,915, issued Sep. 1, 1987; Zarling, et al., U.S. Pat. No. 5,081,029, issued Jan. 14, 1992). Such T lymphocytes may be isolated from the patient or a histocompatible donor. The T lymphocytes are activated in vitro by exposure to the recombinant vaccinia virus of the invention. Activated T lymphocytes are expanded and inoculated into the patient in order to transfer T cell immunity directed against the tumor-associated antigen epitope.

The invention also provides a pharmaceutical pack or kit comprising one or more containers comprising one or more of the ingredients of the vaccine formulations of the invention. Associated with such container(s) can be a notice in the form prescribed by a governmental agency regulating the manufacture, use or sale of pharmaceuticals or biological products, which notice reflects approval by the agency of manufacture, use or sale for human administration.

The invention will be better understood by reference to the specific embodiments detailed in the examples which follow.

EXAMPLE 1

Trimolecular Recombination Employing Modified Vaccinia Virus Vectors to Make Expression Libraries This example describes a tri-molecular recombination method employing modified vaccinia virus vectors and related transfer plasmids that generates close to 100% recombinant vaccinia virus and, for the first time, allows efficient construction of a representative DNA library in vaccinia virus.

Construction of the Vectors

The previously described vaccinia virus transfer plasmid pJ/K, a pUC 13 derived plasmid with a vaccinia virus thymidine kinase gene containing an in-frame Not I site (Merchlinsky, M. et al., Virology 190:522–526), was further modified to incorporate a strong vaccinia virus promoter followed by Not I and Apa I restriction sites. Two different vectors, p7.5/tk and pEL/tk, included, respectively, either the 7.5K vaccinia virus promoter or a strong synthetic early/late (E/L) promoter (FIG. 1). The Apa I site was preceded by a strong translational initiation sequence including the ATG codon. This modification was introduced within the vaccinia virus thymidine kinase (tk) gene so that it was flanked by regulatory and coding sequences of the viral tk gene. The modifications within the tk gene of these two new plasmid vectors were transferred by homologous recombination in the flanking tk sequences into the genome of the Vaccinia Virus WR strain derived vNotI⁻ vector to generate new viral vectors v7.5/tk and vEL/tk. Importantly, following Not I and Apa I restriction endonuclease digestion of these viral vectors, two large viral DNA fragments were isolated each including a separate non-homologous segment of the vaccinia tk gene and together comprising all the genes required for assembly of infectious viral particles. Further details regarding the construction and characterization of these vectors and their alternative use for direct ligation of DNA fragments in vaccinia virus are described in Example 9 infra.

Generation of an Increased Frequency of Vaccinia Virus Recombinants

Standard methods for generation of recombinants in vaccinia virus exploit homologous recombination between a recombinant vaccinia transfer plasmid and the viral genome. Table 1 shows the results of a model experiment in which the frequency of homologous recombination following transfection of a recombinant transfer plasmid into vaccinia virus infected cells was assayed under standard conditions. To facilitate functional assays, a minigene encoding the immunodominant 257–264 peptide epitope of ovalbumin in association with H-2K$^b$ was inserted at the Not I site in the transfer plasmid tk gene. As a result of homologous recombination, the disrupted tk gene is substituted for the wild type viral tk+ gene in any recombinant virus. This serves as a marker for recombination since tk– human 143B cells infected with tk– virus are, in contrast to cells infected with wild type tk+ virus, resistant to the toxic effect of BrdU. Recombinant virus can be scored by the viral pfu on 143B cells cultured in the presence of 125 mM BrdU.

The frequency of recombinants derived in this fashion is of the order of 0.1% (Table 1).

TABLE 1

Generation of Recombinant Vaccinia Virus by Standard Homologous Recombination

| Virus* | DNA | Titer without BrdU | Titer with BrdU | % Recombinant** |
|---|---|---|---|---|
| vaccinia | — | $4.6 \times 10^7$ | $3.0 \times 10^3$ | 0.006 |
| vaccinia | 30 ng pE/Lova | $3.7 \times 10^7$ | $3.2 \times 10^4$ | 0.086 |
| vaccinia | 300 ng pE/Lova | $2.7 \times 10^7$ | $1.5 \times 10^4$ | 0.056 |

*vaccinia virus strain vNotI
**% Recombinant = (Titer with BrdU/Titer without BrdU) × 100

This recombination frequency is too low to permit efficient construction of a cDNA library in a vaccinia vector. The following two procedures were used to generate an increased frequency of vaccinia virus recombinants.

(i) One factor limiting the frequency of viral recombinants generated by homologous recombination following transfection of a plasmid transfer vector into vaccinia virus infected cells is that viral infection is highly efficient whereas plasmid DNA transfection is relatively inefficient. As a result many infected cells do not take up recombinant plasmids and are, therefore, capable of producing only wild type virus. In order to reduce this dilution of recombinant efficiency, a mixture of naked viral DNA and recombinant plasmid DNA was transfected into Fowl Pox Virus (FPV) infected mammalian cells. As previously described by others (Scheiflinger, F., et al., 1992, Proc. Natl. Acad. Sci. USA 89:9977–9981), FPV does not replicate in mammalian cells but provides necessary helper functions required for packaging mature vaccinia virus particles in cells transfected with non-infectious naked vaccinia DNA. This modification of the homologous recombination technique alone increased the frequency of viral recombinants approximately 35 fold to 3.5% (Table 2).

TABLE 2

Generation of Recombinant Vaccinia Virus by Modified Homologous Recombination

| | | Titer | | |
|---|---|---|---|---|
| Virus | DNA | without BrdU | with BrdU | % Recombinant* |
| FPV | None | 0 | 0 | 0 |
| None | vaccinia WR | 0 | 0 | 0 |
| FPV | vaccinia WR | $8.9 \times 10^6$ | $2.0 \times 10^2$ | 0.002 |
| FPV | vaccinia WR + pE/Lova (1:1) | $5.3 \times 10^6$ | $1.2 \times 10^5$ | 2.264 |
| FPV | vaccinia WR + pE/Lova (1:10) | $8.4 \times 10^5$ | $3.0 \times 10^4$ | 3.571 |

Table 2: Confluent monolayers of BSCI cells ($5 \times 10^5$ cells/well) were infected with moi=1.0 of fowlpox virus strain HP1. Two hours later supernatant was removed, cells were washed 2× with Opti-Mem I media, and transfected using lipofectamine with 600 ng vaccinia strain WR genomic DNA either alone, or with 1:1 or 1:10 (vaccinia:plasmid) molar ratios of plasmid pE/Lova. This plasmid contains a fragment of the ovalbumin cDNA, which encodes the SIINFEKL (SEQ ID NO: 10) epitope, known to bind with high affinity to the mouse class I MHC molecule K$^b$. Expression of this minigene is controlled by a strong, synthetic Early/Late vaccinia promoter. This insert is flanked by vaccinia tk DNA. Three days later cells were harvested, and virus extracted by three cycles of freeze/thaw in dry ice isopropanol/37° C. water bath. Crude virus stocks were titered by plaque assay on human TK– 143B cells with and without BrdU.

* %Recombinant=(Titer with BrdU/Titer without BrdU)×100

(ii) A further significant increase in the frequency of viral recombinants was obtained by transfection of FPV infected cells with a mixture of recombinant plasmids and the two large approximately 80 kilobases and 100 kilobases fragments of vaccinia virus v7.5/tk DNA produced by digestion with Not I and Apa I restriction endonucleases. Because the Not I and Apa I sites have been introduced into the tk gene, each of these large vaccinia DNA arms includes a fragment of the tk gene. Since there is no homology between the two tk gene fragments, the only way the two vaccinia arms can be linked is by bridging through the homologous tk sequences that flank the inserts in the recombinant transfer plasmid. The results in Table 3 show that >99% of infectious vaccinia virus produced in triply transfected cells is recombinant for a DNA insert as determined by BrdU resistance of infected tk– cells.

TABLE 3

Generation of 100% Recombinant Vaccinia Virus using Tri-Molecular Recombination

| Virus | DNA | Titer without BrdU | Titer with BrdU | % Recombinant* |
|---|---|---|---|---|
| FPV | Uncut v7.5/tk | $2.5 \times 10^6$ | $6.0 \times 10^3$ | 0.24 |
| FPV | NotI/ApaI v7.5/tk arms | $2.0 \times 10^2$ | 0 | 0 |
| FPV | NotI/ApaI v7.5/tk arms | $6.8 \times 10^4$ + 1:1 pE/Lova | $7.4 \times 10^4$ | 100 |

Table 3: Genomic DNA from vaccinia strain V7.5/tk (1.2 micrograms) was digested with ApaI and NotI restriction endonucleases. The digested DNA was divided in half. One of the pools was mixed with a 1:1 (vaccinia:plasmid) molar ratio of pE/Lova. This plasmid contains a fragment of the ovalbumin cDNA, which encodes the SIINFEKL (SEQ ID NO:10) epitope, known to bind with high affinity to the mouse class I MHC molecule $K^b$. Expression of this mini-gene is controlled by a strong, synthetic Early/Late vaccinia promoter. This insert is flanked by vaccinia tk DNA. DNA was transfected using lipofectamine into confluent mono-layers ($5 \times 10^5$ cells/well) of BSC1 cells, which had been infected 2 hours previously with moi=1.0 FPV. One sample was transfected with 600 ng untreated genomic V7.5/tk DNA. Three days later cells were harvested, and the virus was extracted by three cycles of freeze/thaw in dry ice isopropanol/37° C. water bath. Crude viral stocks were plaqued on TK– 143 B cells with and without BrdU selection.

* %Recombinant=(Titer with BrdU/Titer without BrdU)×100

Construction of a Representative cDNA Library in Vaccinia Virus

A cDNA library is constructed in the vaccinia vector to demonstrate representative expression of known cellular mRNA sequences.

Additional modifications have been introduced into the p7.5/tk transfer plasmid and v7.5/tk viral vector to enhance the efficiency of recombinant expression in infected cells. These include introduction of translation initiation sites in three different reading frames and of both translational and transcriptional stop signals as well as additional restriction sites for DNA insertion.

First, the HindIII J fragment (vaccinia tk gene) of p7.5/tk was subcloned from this plasmid into the HindIII site of pBS phagemid (Stratagene) creating pBS.Vtk.

Second, a portion of the original multiple cloning site of pBS.Vtk was removed by digesting the plasmid with SmaI and PstI, treating with Mung Bean Nuclease, and ligating back to itself, generating pBS.Vtk.MCS–. This treatment removed the unique SmaI, BamHI, SalI, and PstI sites from pBS.Vtk.

Figure 2B:
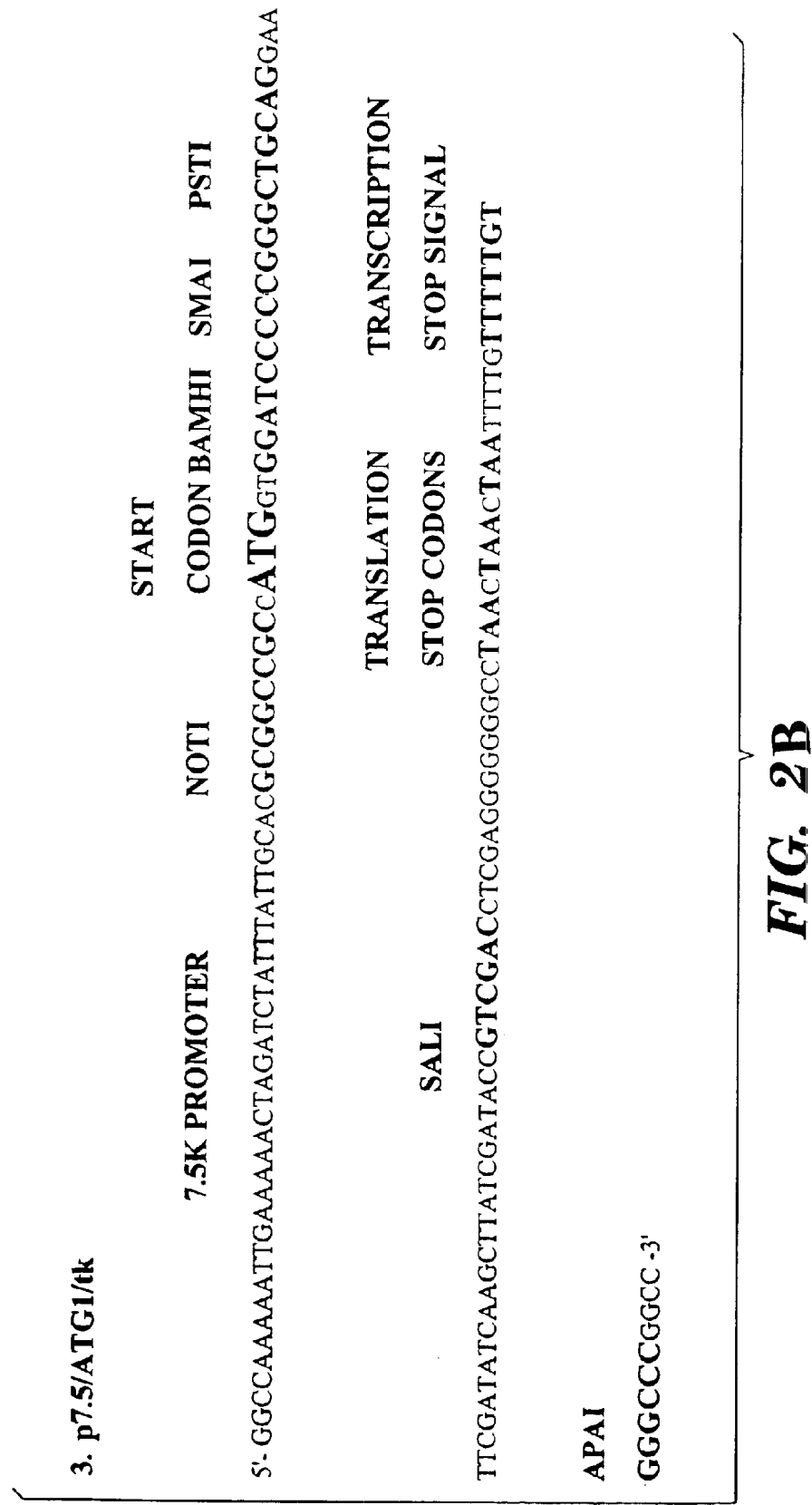
Figure 2C:
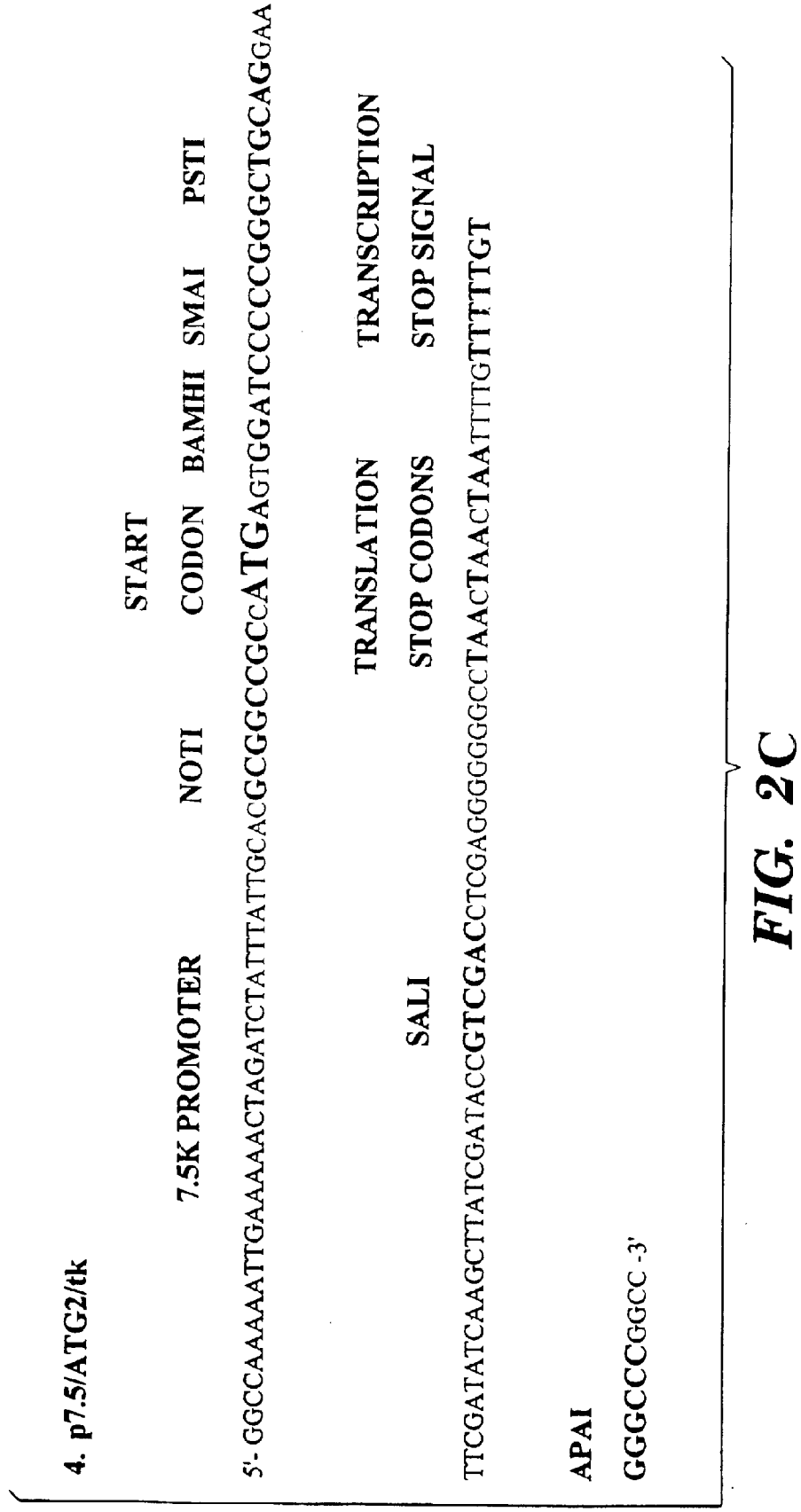

Third, the object at this point was to introduce a new multiple cloning site downstream of the 7.5 k promoter in pBS.Vtk.MCS–. The new multiple cloning site was generated by PCR using 4 different upstream primers, and a common downstream primer. Together, these 4 PCR products would contain either no ATG start codon, or an ATG start codon in each of the three possible reading frames. In addition, each PCR product contains at its 3 prime end, translation stop codons in all three reading frames, and a vaccinia virus transcription double stop signal. These 4 PCR products were ligated separately into the NotI/ApaI sites of pBS.Vtk.MCS–, generating the 4 vectors, p7.5/ATG0/tk, p7.5/ATG1/tk, p7.5/ATG2/tk, and p7.5/ATG3/tk whose sequence modifications relative to the p7.5/tk vector are shown in FIG. 2. Each vector includes unique BamHI, SmaI, PstI, and SalI sites for cloning DNA inserts that employ either their own endogenous translation initiation site (in vector p7.5/ATG0/tk) or make use of a vector translation initiation site in any one of the three possible reading frames (p7.5/ATG1/tk, p7.5/ATG2/tk, and p7.5/ATG3/tk).

In a model experiment cDNA was synthesized from poly-A+ mRNA of a murine tumor cell line (BCA39) and ligated into each of the four modified p7.5/tk transfer plasmids. Twenty micrograms of Not I and Apa I digested v/tk vaccinia virus DNA arms an equal was transfected together with an equimolar mixture of the four recombinant plasmid cDNA libraries into FPV helper virus infected BSC-1 cells for tri-molecular recombination. The virus harvested had a total titer of $6 \times 10^6$ pfu of which greater than 90% were BrdU resistant.

In order to characterize the size distribution of cDNA inserts in the recombinant vaccinia library, individual isolated plaques were picked using a sterile pasteur pipette and transferred to 1.5 ml tubes containing 100 µl Phosphate Buffered Saline (PBS). Virus was released from the cells by three cycles of freeze/thaw in dry ice/isopropanol and in a 37° C. water bath. Approximately one third of each virus plaque was used to infect one well of a 12 well plate containing tk– human 143B cells in 250 µl final volume. At the end of the two hour infection period each well was overlayed with 1 ml DMEM with 2.5% fetal bovine serum (DMEM-2.5) and with BUdR sufficient to bring the final concentration to 125 µg/ml. Cells were incubated in a $CO_2$ incubator at 37° C. for three days. On the third day the cells were harvested, pelleted by centrifugation, and resuspended in 500 µl PBS. Virus was released from the cells by three cycles of freeze/thaw as described above. Twenty percent of each virus stock was used to infect a confluent monolayer of BSC-1 cells in a 50 mm tissue culture dish in a final volume of 3 ml DMEM-2.5. At the end of the two hour infection period the cells were overlayed with 3 ml of DMEM-2.5. Cells were incubated in a $CO_2$ incubator at 37° C. for three days. On the third day the cells were harvested, pelleted by centrifugation, and resuspended in 300 µl PBS. Virus was released from the cells by three cycles of freeze/thaw as described above. One hundred microliters of crude virus stock was transferred to a 1.5 ml tube, an equal volume of melted 2% low melting point agarose was added, and the virus/agarose mixture was transferred into a pulsed field gel sample block. When the agar worms were solidified they were removed from the sample block and cut into three equal sections. All three sections were transferred to the same 1.5 ml tube, and 250 µl of 0.5M EDTA, 1% Sarkosyl, 0.5 mg/ml Proteinase K was added. The worms were incubated in this solution at 37° C. for 24 hours. The worms were washed several times in 500 µl 0.5× TBE buffer, and one section of each worm was transferred to a well of a 1% low melting point agarose gel. After the worms were added the wells were sealed by adding additional melted 1% low melting point agarose. This gel was then electorphoresed in a Bio-Rad pulsed field gel electrophoresis apparatus at 200 volts, 8 second pulse times, in 0.5× TBE for 16 hours. The gel was stained in ethidium bromide, and portions of agarose containing vaccinia genomic DNA were excised from the gel and transferred to a 1.5 ml tube. Vaccinia DNA was purified from the agarose using β-Agarase (Gibco) following the recommendations of the manufacturer. Purified vaccinia DNA was resuspended in 50 µl ddH$_2$O . One microliter of each DNA stock was used as the template for a Polymerase Chain Reaction (PCR) using vaccinia TK specific primers MM428 and MM430 (which flank the site of insertion) and Klentaq Polymerase (Clontech) following the recommendations of the manufacturer in a 20 µl final volume. Reaction conditions included an initial denaturation step at 95° C. for 5 minutes, followed by 30 cycles of: 94° C. 30 seconds, 55° C. 30 seconds, 68° C. 3 minutes. Two and a half microliters of each PCR reaction was resolved on a 1% agarose gel, and stained with ethidium bromide. Amplified fragments of diverse sizes were observed. When corrected for flanking vector sequences amplified in PCR the inserts range in size between 300 and 2500 bp.

The vaccinia virus cDNA library was further characterized in terms of the representation of clones homologous to the murine alpha tubulin sequence. Twenty separate pools with an average of either 300, 900 or 2,700 viral pfu from the library were amplified by infecting a monolayer of 143B tk– cells in the presence of BrdU. DNA was extracted from each infected culture after three days and assayed for the presence of an alpha tubulin sequence by PCR with tubulin specific primers. Poisson analysis of the frequency of positive pools indicates a frequency of one alpha tubulin recombinant for every 2000 to 3000 viral pfu. This is not significantly different from the expected frequency of alpha tubulin sequences in this murine tumor cell line and suggests representative expression of this randomly selected sequence in the vaccinia cDNA library.

Discussion

The above-described tri-molecular recombination strategy yields close to 100% viral recombinants. This is a highly significant improvement over current methods for generating viral recombinants by transfection of a plasmid transfer vector into vaccinia virus infected cells. This latter procedure yields viral recombinants at a frequency of the order of only 0.1%. The high yield of viral recombinants in tri-molecular recombination makes it possible, for the first time, to efficiently construct genomic or cDNA libraries in a vaccinia virus derived vector. In the first series of experiments a titer of $6 \times 10^6$ recombinant virus was obtained following transfection with a mix of 20 micrograms of Not I and Apa I digested vaccinia vector arms together with an equimolar concentration of tumor cell cDNA. This technological advance creates the possibility of new and efficient screening and selection strategies for isolation of specific genomic and cDNA clones.

The tri-molecular recombination method as herein disclosed may be used with other viruses such as mammalian viruses including vaccinia and herpes viruses. Typically, two viral arms which have no homology are produced. The only way that the viral arms can be linked is by bridging through homologous sequences that flank the insert in a transfer vector such as a plasmid. When the two viral arms and the transfer vector are present in the same cell the only infectious virus produced is recombinant for a DNA insert in the transfer vector.

Libraries constructed in vaccinia and other mammalian viruses by the trimolecular recombination method of the present invention may have similar advantages to those described here for vaccinia virus and its use in identifying target antigens in the CTL screening system of the invention. Similar advantages are expected for DNA libraries constructed in vaccinia or other mammalian viruses when carrying out more complex assays in eukaryotic cells. Such assays include but are not limited to screening for DNA encoding receptors and ligands of eukaryotic cells.

EXAMPLE 2

Induction of Cytotoxic T Cells Specific for Human Tumors in HLA and Human CD8 Transgenic Mice In this example, HLA and human CD8 transgenic mice were tolerized with a non-tumorigenic, immortalized normal human cell line that does not express costimulator activity for murine T cells and were subsequently immunized with B7 (costimulator) transfected tumor cells derived by in vitro mutagenesis or oncogene transformation from that same normal cell line. The HLA transgene permits selection of a high affinity, HLA-restricted T cell repertoire in the mouse thymus. In addition, a human CD8 transgene is required because murine CD8 does not interact efficiently with human class I MHC. Subsequent to immunization with B7 transfected tumor cells, splenic CD8+ T cells are isolated and stimulated again in vitro in the absence of costimulation with non-tumorigenic, immortalized human cells. Two pathways of tolerance induction for antigens shared by the tumorigenic and non-tumorigenic cell lines may be activated through these manipulations. As known to those skilled in the art, antigen exposure in very young mice favors tolerance induction by mechanisms that may include both clonal deletion and induction of T cell anergy. Further, restimulation of activated T cells through their antigen-specific receptors in the absence of costimulator activity induces apoptotic elimination of those T cells. This immunization regimen enriched for tumor-specific CTL that did not crossreact with the homologous normal cells.

A series of tumor cell lines were used that were all derived from a single immortalized, non-tumorigenic cell line. The non-tumorigenic cells were used to induce tolerance to the large number of normal human proteins that are also expressed in tumor cells. Availability of a panel of tumors independently derived from the same normal cells by diverse carcinogens or oncogene transformation makes it possible to filter out antigenic changes that are carcinogen specific or that may arise by random genetic drift during in vitro propagation of a tumor cell line.

Cytotoxic T cells specific for human bladder tumor cell lines were induced and isolated from (HLA-A2/$K^b$×human CD8)$F_1$ hybrid double transgenic mice that had been tolerized to the normal cell line from which the tumors derive. Neonatal mice were injected intraperitoneally with $5 \times 10^6$ non-tumorigenic SV-HUC. Seven weeks later they were immunized with $5 \times 10^6$ B7.1 transfected ppT11.B7 tumor cells. ppT11 is one of several independent tumor cell lines derived from SV-HUC by in vitro carcinogenesis (Christian, et al., *Cancer Res.* 47:6066–6073 (1987); Pratt, et al., *Cancer Res.* 52:688–695 (1992); Bookland, et al., *Cancer Res.* 52:1606–1614 (1992)). One week after immunization, spleen was removed and a single cell suspension prepared. CD8 positive T cell precursors were enriched on anti-Lyt-2 coated MACS (Magnetic cell sorting beads) as recommended by the manufacturer (Miltenyi Biotech, Sunnyvale, Calif.). $1.5 \times 10^6$ CD8 enriched T cells were then restimulated in vitro with $4 \times 10^5$ SV-HUC in 3 ml of RPMI 1640+10% fetal bovine serum. The rationale is that any SV-HUC specific T cells that escape neonatal tolerance induction and are activated in vivo by stimulation with crossreactive determinants of ppT11.B7, might now be induced to undergo apoptosis by restimulation in vitro with costimulator activity negative SV-HUC cells. After 24 hours, T cells are again stimulated with ppT11.B7 in the presence of 2000 Units/ml of recombinant murine IL-6. On day 7 the cycle of SV-HUC stimulation followed 24 hours later by restimulation with ppT11.B7 is repeated. This second round of stimulation with ppT11.B7 is carried out in the presence of 10 nanogram/ml recombinant murine IL-7 and 50 Units/ml recombinant murine IL-2. CTL activity is determined 5 days later by standard chromium release assay from labeled targets SV-HUC, ppT11.B7 and YAC-1, a cell line sensitive to non-specific killing by murine NK cells. The results in Table 4 show that CTL from ppT11.B7 immunized mice that were not previously tolerized to SV-HUC are equally reactive with SV-HUC and ppT11 target cells. In contrast, following neonatal tolerization with SV-HUC, cytolytic T cells at an effector:target ratio of 5:1 are significantly more reactive with ppT11.B7 tumor cells than with SV-HUC. Note that B7 costimulator activity is not required at the effector stage as similar results are obtained with B7 transfected or non-transfected target cells.

TABLE 4

Tumor-specific response in (HLA-A2/$K^b$ × human CD8)$F_1$ hybrid transgenic mice neonatally tolerized with SV-HUC parental cells and then immunized with B7 costimulator transfected ppT11.B7 human bladder tumor cells.

| Tolerogen: | None | | SV-HUC | |
|---|---|---|---|---|
| Immunogen: | ppT11.B7 | | ppT11.B7 | |
| | Effector:Target ratio | | | |
| Target | 5:1 | 10:1 | 2:1 | 5:1 |
| SV-HUC | 29 | 68 | 14 | 19 |
| ppT11.137 | 14 | 70 | 17 | 51 |
| YAC-1 | 6 | 6 | nd | 3 | nd = not done

The significance of this experimental protocol is that it offers a means of selecting murine, HLA-restricted cytolytic T cells specific for human epithelial tumor cells. As noted previously, it has proved exceedingly difficult to isolate such T cells directly from either patient PBL or tumor infiltrating lymphocytes of tumors other than melanoma and perhaps renal cell carcinoma. In addition, as emphasized below, this same strategy can be implemented in two stages. Differentially immunogenic molecules of the human tumor can first be identified employing tumor-specific CTL restricted to a variety of different animal MHC. These antigens can, as described in Example 12, subsequently be characterized in human subjects or transgenic mice for the ability to be processed and presented in association with different human HLA types. An advantage of this two stage approach is that numerous different MHC molecules are available in a variety of inbred strains and these can be employed to capture an equally broad range of tumor-specific immunogenic peptides in the initial screening.

EXAMPLE 3

High-Throughput Strategy for Selection of DNA Recombinants from a Library that Encodes the Target Epitopes of Specific Cytotoxic T Cells In this example, a model system was assayed to determine the level of enrichment that can be obtained through a procedure that selects for DNA recombinants that encode the target epitopes of tumor specific cytotoxic T cells.

Methods and Results

A specific vaccinia recombinant that encodes a well characterized ovalbumin peptide (SIINFEKL) (SEQ ID NO:10) was diluted with non-recombinant virus so that it constituted either 0.2%, 0.01%, or 0.001% of viral pfu. This ovalbumin peptide is known to be processed and presented to specific CTL in association with the murine class I MHC molecule H-$2K^b$. An adherent monolayer of MC57G cells that express H-$2K^b$ were infected with this viral mix at m.o.i.=1 (approximately $5×10^5$ cell/well). MC57G cells do not themselves express ovalbumin peptide, but do express H-$2K^b$, which allows them to associate with and present ovalbumin peptide to the T cells.

Following 12 hours of infection with the recombinant vaccinia virus expressing ovalbumin peptide, ovalbumin peptide-specific CTL, derived by repeated in vitro stimulation of ovalbumin primed splenic T cells with the immunodominant ovalbumin SIINFEKL (SEQ ED NO: 10) peptide, were added for 30 min.

During this time, some of the adherent cells infected with a recombinant particle that leads to expression of the ovalbumin peptide interacted with a specific cytotoxic T cell and underwent a lytic event. Cells that underwent a lytic event were released from the monolayer. After 30 min, the monolayer was gently washed, and the floating cells and the remaining adherent cells were separately harvested.

Virus extracted from each cell population was titred for the frequency of ovalbumin recombinant viral pfu. Virus extracted from floating cells was then used as input to another enrichment cycle with fresh adherent MC57G cells and ovalbumin peptide-specific CTL. It was observed that, following enrichment of VVova to greater than 10% of total virus, further enrichment of the recombinant virus was accelerated if the m.o.i. in succeeding cycles was reduced from 1 to 0.1. The results, presented in Table 5, demonstrate marked enrichment of VVova recombinant virus from an initial concentration of 0.2% to 49% or from 0.01% to 39% in 5 enrichment cycles and from 0.001% to 18% in 6 enrichment cycles. Note that with $5×10^5$ adherent MC57G cells per well and m.o.i=1, an initial concentration of 0.001% VVova recombinant virus is equivalent, on average, to seeding only 5 recombinant pfu among $5×10^5$ wild type vaccinia virus in a single culture well. A very substantial enrichment is achieved even under these conditions.

TABLE 5

Multiple Cycles of Enrichment for Vvova

| | | % VVova in Floating cells* | | |
|---|---|---|---|---|
| Enrichment cycle # | | Exp. 1 | Exp. 2 | Exp. 3 |
| moi = 1 | 0 | 0.2 | 0.01 | 0.001 |
| | 1 | 2.1 | 0.3 | nd |
| | 2 | 4.7 | 1.1 | nd |
| | 3 | 9.1 | 4.9 | nd |
| | 4 | 14.3 | 17.9 | 1.4 |
| | 5 | 24.6 | | 3.3 |
| | 6 | | | 18.6 |
| moi = 0.1 | 5 | 48.8 | 39.3 | |

*% Vvova = (Titer with BrdU/Titer without BrdU) × 100
nd = not determined

Discussion

The above-described selection method for isolating DNA clones that encode target epitopes of specific cytotoxic T cells from a viral library is far more efficient than existing methods for accomplishing this same goal. Prior to the present invention, the most widely employed method requires transfection of numerous small pools of recombinant plasmids into separate target populations in order to assay T cell stimulation by a minor component of some pool. Because this requires screening out many negative plasmid pools, it is a far more labor intensive procedure than the positive selection method described herein. For a given investment of resources, the method described here can detect positive DNA clones that occur at a much lower frequency than would otherwise be possible. The design principle of this strategy can be directly extended to screening and selection of DNA clones with specific antibodies as well as with CTL.

EXAMPLE 4

Identification of Potential Tumor-specific Antigens that Are Differentially Expressed in Tumors Identification of genes that are differentially expressed in human tumors, cancers, or infected cells could facilitate development of broadly effective human vaccines. Most methods for identification of differential gene expression are variations of either subtractive hybridization or the more recently described differential display technique.

Representational difference analysis (RDA) is a subtractive hybridization based method applied to "representations" of total cellular DNA (Lisitsyn, N. and N., M. Wigler, "Cloning the differences between two complex genomes," *Science* 259:946–951 (1993)). The differential display methods of Liang and Pardee (*Science* 257:967–971 (1992)) employ an arbitrary 10 nucleotide primer and anchored oligo-dT to PCR amplify an arbitrary subset of fragments from a more complex set of DNA molecules. As described below (Example 4), we have modified differential display to enhance the efficiency with which differentially expressed genes can be identified. In this example we illustrate how application of these methods to a related set of tumors independently derived from a single non-tumorigenic, immortalized cell line facilitates identification of tumor-specific gene products.

Experiments described by Sahasrabudhe, et al., (*J. Immunology* 151:6302–6310 (1993)), focused on a set of murine tumor cell lines, all of which were independently derived from a single cloned, non-tumorigenic BALB/c embryonic fibroblast cell line. These tumors were of particular interest because they are known to share an immunoprotective antigen. The goal of these experiments was to arrive at a molecular definition of that shared tumor antigen. The ready availability of tumor cells, as well as the normal cells from which they were derived, was exploited for efficient analysis of differential gene expression and tumor immunogenicity by the methods described below.

The availability of multiple tumors independently derived from the same normal cells by diverse carcinogens (or oncogene transformation) also makes it possible to filter out antigenic changes that are carcinogen specific or that may arise as a result of random genetic drift during in vitro propagation of tumor cells. (See Example 10, where a series of human tumor cell lines is described that satisfy the requirements of this analysis).

The relationship between the process of transformation and expression of shared tumor rejection antigens was investigated by characterizing the immunological relationships among a series of murine tumors (BCA 34, BCA 39, BCA 22, and BCB 13) independently derived from B/C-N7.1C.1, a contact inhibited, non-tumorigenic clone of a continuous fibroblast cell line derived from a BALB/c fetus (Collins, et al., *Nature* 299:167 (1992); Lin, et al., *JNCI* 74:1025 (1985)). Although the proximal cause of tumor transformation may have been a carcinogen induced mutation, this model afforded the opportunity to determine if the process of transformation is also associated with expression of a limited number of shared antigens.

As reported by Sahasrabudhe, et al. (*J. Immunology* 151:6302–6310 (1993)), immunological analysis demonstrates that three of four B/c.N derived tumors confer crossprotective immunity against each other. Concordant with the in vivo cross-protection data, cytolytic T cell clones from mice immunized with one of the immunologically related tumors specifically lyse all three immunologically related tumors but, importantly, do not react with the parental B/c.N cells or with the immunologically independent BCB 13 tumor. The observation of immunological cross-reactivity among a group of tumors independently derived from a cloned non-tumorigenic parental cell line strongly suggests that a non-random transformation associated process gives rise to recurrent expression of the same tumor antigen(s). Two methods for analyzing differential gene expression, representational difference analysis (RDA) and modified differential display, were employed to isolate cDNA that might encode the relevant tumor antigen(s).

Representational Difference Analysis (RDA)

Figure 3:
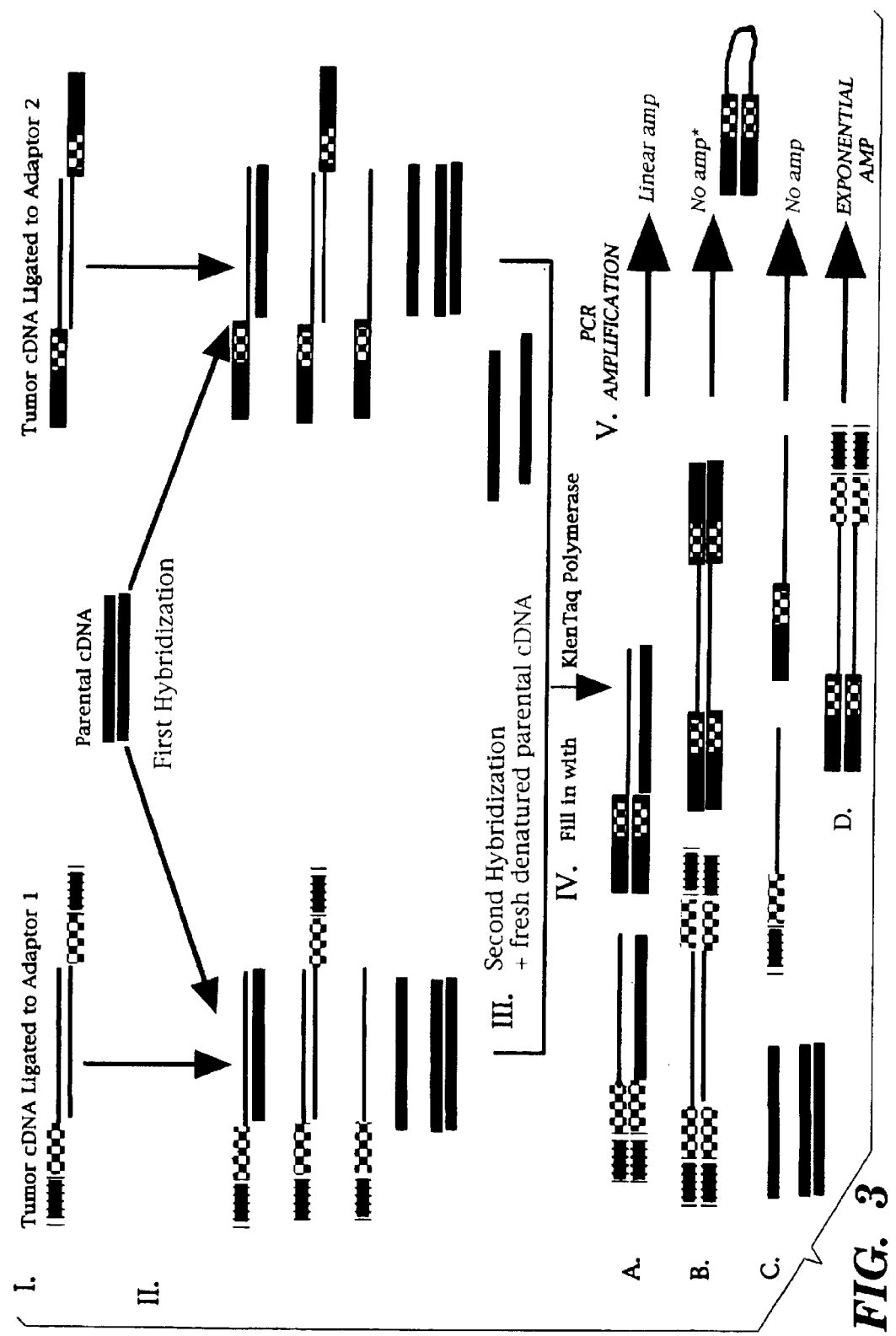
FIG. 3. Schematic of the Clontech PCR SELECT™ method of Representational Difference Analysis. Adapted from information provided by the manufacturer.

The PCR SELECT™ variation of RDA is marketed by Clontech (Palo Alto, Calif.). The following general protocol outlined in the text and in FIG. 3 is a summary of the manufacturer's recommendations. cDNA is synthesized from both a tracer (represented by BCA 39 tumor mRNA) and a driver (represented by parental B/c.N mRNA). "Representations" of both tracer and driver cDNA are created by digestion with RsaI which cuts the four-base recognition sequence GTAC to yield blunt end fragments. Adaptors, which eventually serve as primer sites for PCR, are ligated to the 5' ends of only the tracer cDNA fragments (FIG. 3). Two aliquots of tracer representation are separately ligated with two different adapters. A series of two hybridizations are carried out. In the first set of hybridizations, each adapter ligated tracer sample is denatured and hybridized with a ten fold excess of the denatured representation of driver cDNA for 8 hours. Under these conditions re-annealing of all molecules is incomplete and some of both the high and low copy molecules remain single stranded. Since re-annealing rates are faster for more abundant species, this leads to normalization of the distribution through relative enrichment of low copy number single stranded molecules. The two hybridization reactions with each of the different adapter ligated tracer cDNA representations are then combined without fractionation or further denaturation but with addition of more freshly denatured driver in a second hybridization reaction that is allowed to proceed further to completion, approximately 20 hours.

An aliquot of the products from the second hybridization is used as a template for a high stringency PCR reaction, using the known sequences at the 5' ends of the ligated adapters as primers. The key here is that only tumor tracer sequences that 1) remain single stranded through the first hybridization and 2) hybridize to a complementary tracer sequence ligated to the alternate adapter in the second hybridization can be exponentially amplified during PCR. This excludes both tracer and driver species that either remain single stranded or that have hybridized to excess driver (since they have a complementary primer at only one or neither end of the molecule), as well as tracer sequences that hybridize to a molecule with the same adapter (because the adapters are longer than the primers and hybridize to their own complement with higher affinity when it is present on the opposite end of a denatured single stranded molecule—a reaction termed "Suppression PCR" by Clontech). Finally, a second high stringency PCR is performed using nested primers built into the adapters so as to further reduce background and enrich for differentially expressed sequences. The products of the second PCR are electrophoresed and visualized on an agarose gel. Individual bands are excised and subcloned for further analysis.

Representational Difference Analysis of Genes that Encode Potential Tumor Immunogens This example describes how the PCR SELECTS cDNA subtraction method (Clontech Laboratories) was successfully employed to identify a strong candidate for the shared tumor antigen in a set of immunologically related murine tumors.

Figure 4:
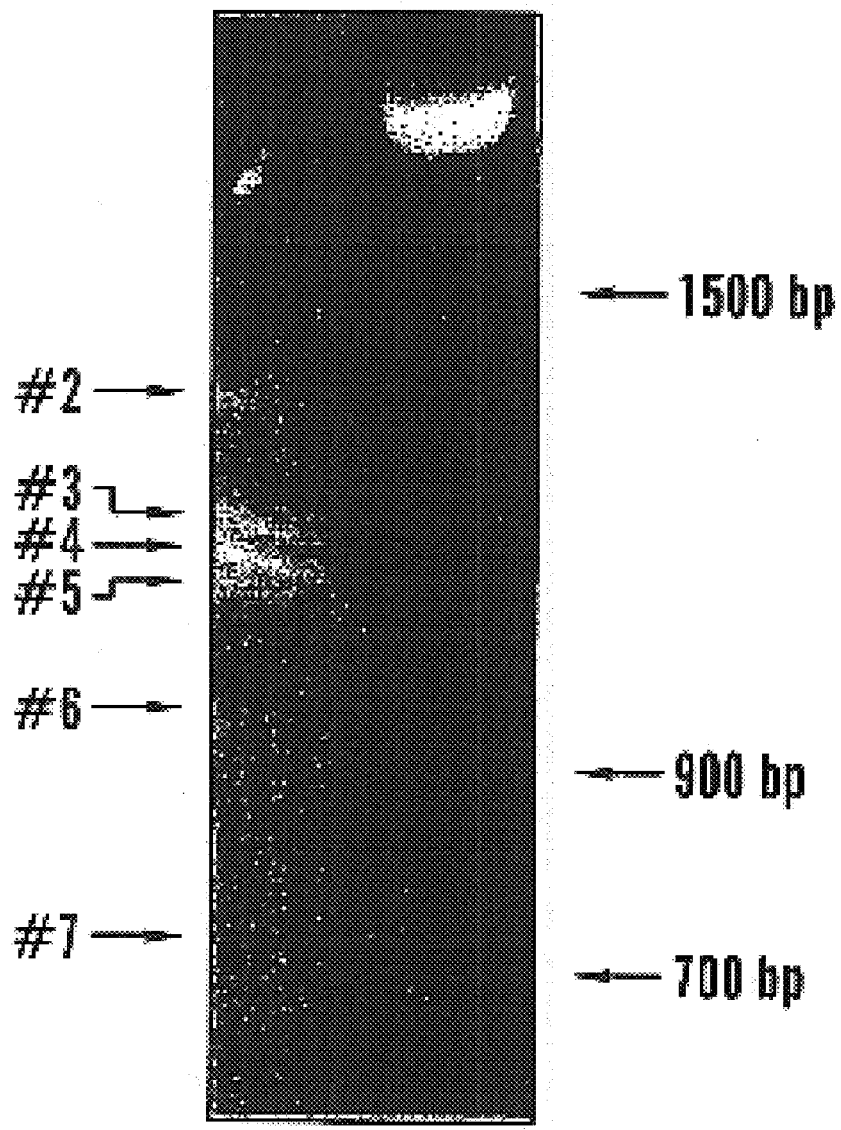
FIG. 4. BCA 39 tumor DNA fragments amplified by PCR following RDA subtraction of B/c.N parental sequences. Nested primers incorporated into the RDA adapters ligated to BCA 39 tumor cell cDNA were employed for sequential PCR amplification of the DNA fragments recovered from RDA. Bands are resolved on a 2% Metaphor agarose gel. One additional low molecular weight band ran off the illustrated gel and was recovered from a shorter electrophoretic run.
Figure 5:
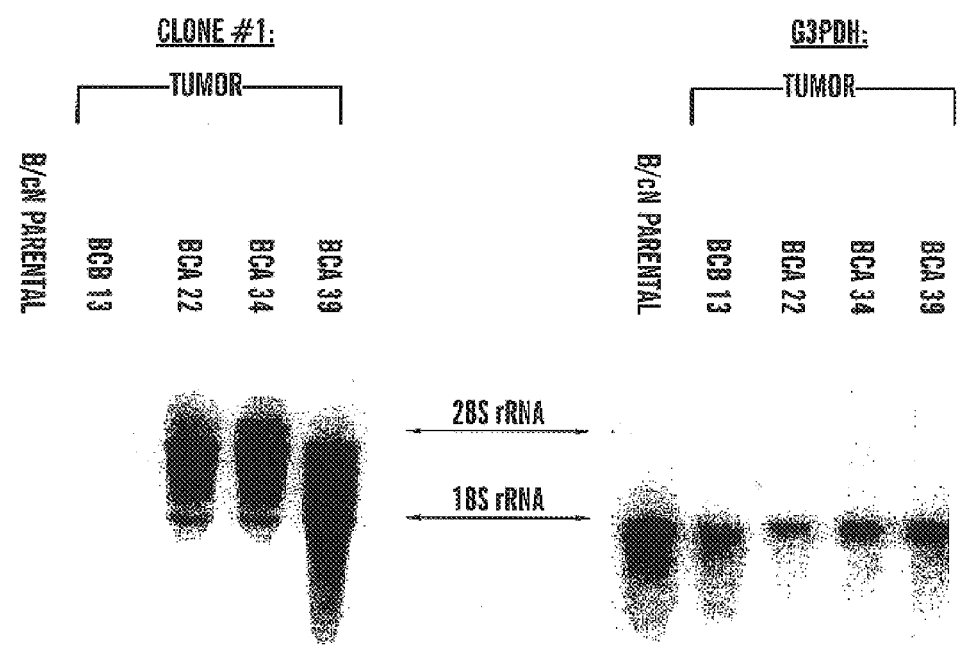
FIG. 5. Hybridization of an RDA fragment of (A) an IAP pol gene or (B) a fragment of the ubiquitously expressed murine G3PDH cDNA to Northern blots of BCA 39 tumor RNA. 15 micrograms of total RNA was transferred from 1% alkaline agarose gel to Genescreen nylon membrane by capillary blot in 10X SSC. The Northern blot was first hybridized to the $^{32}$P labeled RDA clone 1 DNA ($10^5$ cpm/ml Stark's hybridization buffer), then stripped and hybridized with a 350 bp fragment of G3PDH cDNA.

As shown in FIG. 4, subtraction of a fragmented representation of normal cell cDNA from a similar representation of BCA 39 tumor cDNA resulted in identification of a series of seven clearly distinguishable subtraction products ranging in size from approximately 300 to 2200 base pairs. To confirm that these DNA fragments were indeed differentially expressed, each band was cloned into Bluescript plasmid (Stratagene) and the DNA inserts of at least 5 colonies from each band were analyzed by Northern blot hybridization to RNA of the five different cell lines: the parental cells, the three immunologically crossreactive and the one non-crossreactive tumor cell line. Representative results for clone 3f derived from RDA band 1 are shown in FIG. 5A.

The probe hybridized to at least three. transcripts in the BCA 22, 34 and 39 tumor mRNA. Expression of these transcripts is unique to these three immunologically cross-reactive tumors. Minimal hybridization is detected with RNA of the parental B/c.N cells or of the non-crossreactive BCB 13 tumor. Similar results were obtained in four Northern blots with independent RNA preparations. The integrity and relative loading of RNA samples was determined by hybridization to a fragment of the mouse G3PDH gene (FIG. 5B).

The sequence of clone 3f was determined and found to be strongly homologous to a portion of the sequence of a murine intracisternal type A particle (IAP element) (Aota, et al., *Gene* 56:1–12 (1987)). IAPs are endogenous retrovirus-like particles that localize to the cisternae of the endoplasmic reticulum. They are non-infectious because they do not encode functional packaging proteins; the potential env region of the sequence contains many conserved stop codons (Kuff and Lueders, *Adv. Cancer Res.* 51:183–276 (1988)). Most IAPs do encode a 73 kDa major gag protein, and a pol polypeptide with some reverse transcriptase properties (Wilson and Kuff, *Proc. Natl. Acad. Sci. USA* 69:1531–1536 (1972)). Expression of IAP transcripts has been described in various mouse primary tumors (including plasmacytomas, papillomas, carcinomas, mammary tumors, sarcomas, hepatomas) and established mouse tumors and cell lines (including Friend erythroleukemias, myelomonocytic leukemia, T lymphomas, myelomas). Although expression in normal thymus may be elevated, only very low levels of expression are detected in most normal mouse somatic tissues (Kuff and Lueders, *Adv. Cancer Res.* 51:183–276 (1988)).

Characterization of Differentially Expressed Gene Sequence from RDA

Semi-quantitative PCR is a more sensitive test for differential expression than Northern Blot analysis. Clone 3f sequence specific primers were used to amplify full length oligo-d7 primed cDNA from both the BCA 39 tumor and the parental cell line. Amplification with mouse tubulin primers was used to normalize the amount of template between the two cell lines. Equal aliquots of each template were amplified through a variable number of PCR cycles. In each case an estimate of the relative template concentration was derived by fitting a line to the portion of the amplification curve in which product increases exponentially with cycle number. The assumption is that in this region yield is a linear function of (initial template concentration)*($a^n$) where a=average amplification per cycle in that PCR region, usually between 1.5 and 1.8, and n=cycle number. It was determined that expression of the 3f fragment is at least 7 times greater in the BCA39 tumor cDNA relative to the parental B/c.N.

Differential expression in tumor RNA was confirmed for the inserts of 12 additional clones derived from the six other RDA bands. Northern analysis showed the identical hybridization pattern characteristic of IAP transcripts as observed for clone 3f. The sequence of each clone was determined and found to be homologous to other regions of the IAP genome.

Figure 6:
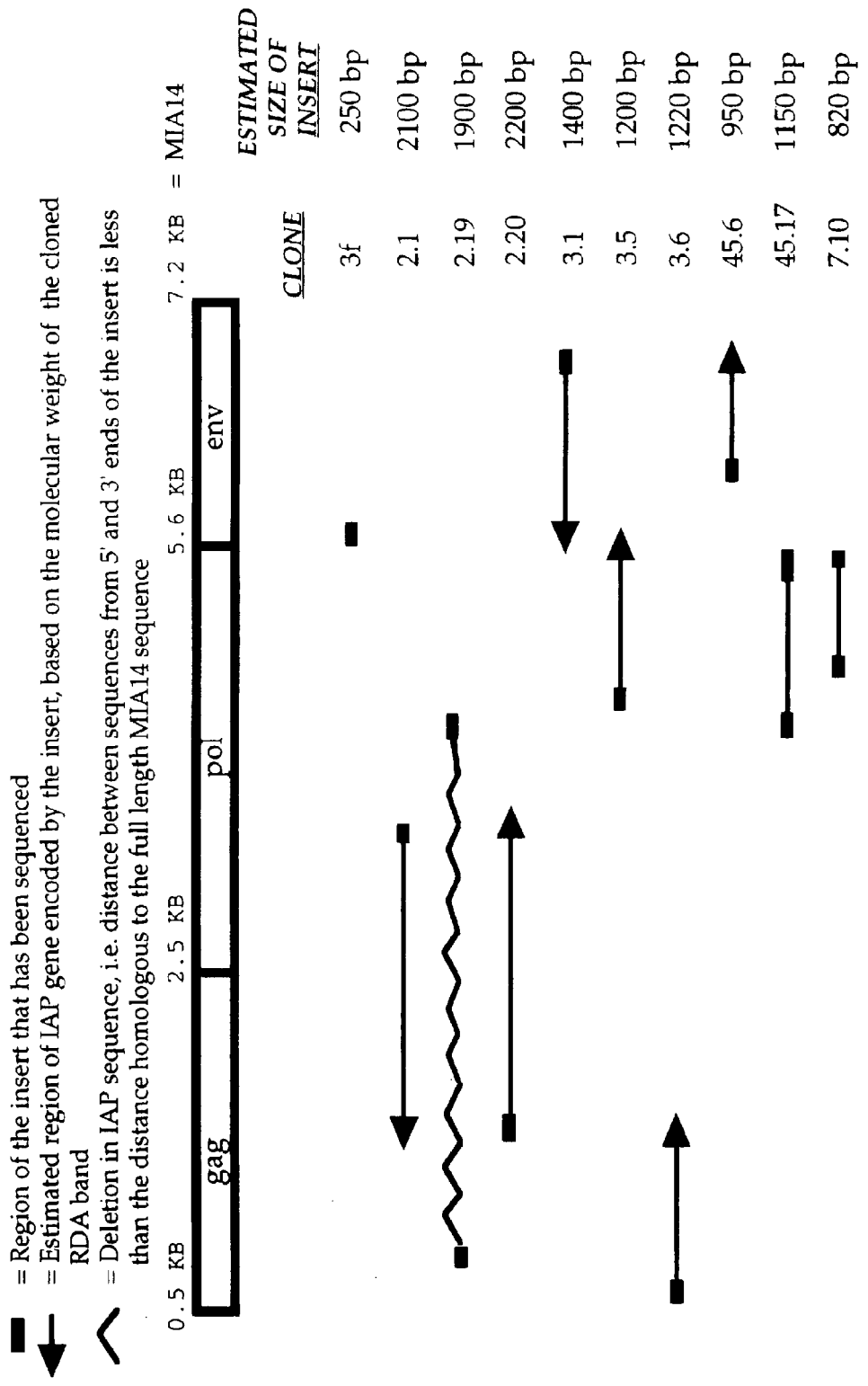
FIG. 6. RDA clones encoding fragments of IAP gene elements compared with the full length IAP clone MIA14. One or both terminal regions (filled rectangular box) of each RDA clone were sequenced to identify homology to subregions of an IAP element. The extent of overlap was estimated from either the fragment size or, where the sequence at both termini of a fragment was determined, the known IAP MIA14 sequence spanning the two termini of that fragment. In one case, clone 2.19, the two measures were not consistent suggesting a deletion in this IAP fragment in BCA 39 tumor cells.

A map of the relative position of 10 unique RDA clones is shown in FIG. 6. It can be seen that cumulatively these inserts cover most of the IAP genome.

It is particularly striking that expression of these IAP sequences is shared among the three immunologically cross-reactive tumors (BCA 39, BCA 34, and BCA 22) but is absent or very low in both the B/c.N parental cells and the immunologically unrelated BCB 13 tumor. An IAP epitope is, therefore, a strong candidate for this shared tumor antigen. Experiments are in progress to transfect the different RDA clones into antigen negative B/c.N cells which will then be tested for sensitization to lysis by tumor-specific CTL. Transcriptional activation of endogenous retroviral elements including IAP may represent a new class of shared tumor rejection antigens. It has been reported (de Bergeyck, et al., 1994, Eur. J. Immunol. 24:2203–2212) that the tumor antigen LEC-A on the murine LEC spontaneous leukemia is also encoded by the gag gene of an IAP element. Recently, a tumor rejection antigen of a murine colon tumor, CT26, was found to be encoded by another type of endogenous retrovirus, a type C particle (Huang, et al., *Proc. Natl. Acad. Sci. USA* 93:9730–9735 (1996)). Retroviral-like elements are also present in the human genome: expression of the pol gene has been detected in human breast (Moyret, et al., *Anticancer Res.* 8:1279–1283 (1988)) and colorectal carcinomas (Moshier, et al., *Biochem. Biophys. Res. Commun.* 139:1071–1077 (1986)), and antibody to the gag gene product has been reported in the sera of patients with human seminoma (Sauter, et al., *J. Virol.* 69:414–421 (1995)) and renal cell carcinoma (Wahlstrom, et al., *Lab. Invest.* 53:464–469 (1985)).

Modified Differential Display of Genes Encoding Potential Tumor Immunogens

In the following example, the differential display methods of Liang and Pardee (1992, Science 257:967–971) were modified to improve resolution of DNA fragments and reduce the frequency of false positives.

The differential display method as originally described by Liang and Pardee (*Science* 257:967–971 (1992)) employs an arbitrary 10 nucleotide primer and anchored oligo-dT to PCR amplify an arbitrary subset of fragments from a more complex set of DNA molecules. In principle, differences among the fragments generated from normal and tumor cell lines should reflect differences in gene expression in the two cell types. In practice, this method sometimes works well but often gives rise to numerous false positives. That is, bands which appear to be differentially displayed are, upon further characterization, found not to be differentially expressed. This is presumably due to variable PCR amplification of individual species in complex populations and a relatively high background that can obscure less prominent bands. Since considerable effort is required to establish differential expression, these endemic false positives are costly in terms of efficiency and productivity. A single arbitrary primer may also be used for differential display, as described by Welch et al. (3,4). Use of single primers does, however, require synthesis of a much larger set of independent primers to achieve the same coverage of a complex cDNA population.

Hence, there exists a need for improved differential display methods that improve resolution of DNA fragments and that reduce the frequency of false positives.

In order to improve the resolution of fragments and reduce the frequency of false positives, a second arbitrary primer was substituted for the anchored oligo-dT employed in PCR amplification. This results in fewer DNA products in each PCR reaction so that individual DNA fragments can be more reliably resolved on sequencing gels.

Because each subset of fragments generated in this modified differential display protocol is a smaller representation of total cDNA, more primer pairs are required for adequate sampling. Employing the negative binomial distribution, it can be predicted that if 12 independent primers are utilized in all 66 possible primer pair combinations there is a greater than 85% probability that for an average size eukaryotic cDNA at least one primer pair will amplify a representative PCR fragment of size ≧70 bp.

Table 6 lists the sequences of the 12 arbitrary decamers from which primer pairs are selected for modified differential display. The specific primers were chosen on the basis of their sequence diversity, 3'hybridization affinity, and minimal pair-wise hybridization.

TABLE 6

Arbitrary Primers For Modified Differential Display

| | | |
|---|---|---|
| TAC AAC GAG G | MR_1 | (SEQ ID NO: 11) |
| GTC AGA GCA T | MR_2 | (SEQ ID NO: 12) |
| GGA CCA AGT C | MR_5 | (SEQ ID NO: 13) |
| TCA GAC TTC A | MR_7 | (SEQ ID NO: 14) |
| TAC CTA TGG C | MR_8 | (SEQ ID NO: 15) |
| TGT CAC ATA C | MR_15 | (SEQ ID NO: 16) |
| TCG GTC ACA G | MR_9 | (SEQ ID NO: 17) |
| ATC TGG TAG A | MR_10 | (SEQ ID NO: 18) |
| CTT ATC CAC G | MR_11 | (SEQ ID NO: 19) |
| CAT GTC TCA A | MR_12 | (SEQ ID NO: 20) |
| GAT CAA GTC T | MR_14 | (SEQ ID NO: 21) |
| CTG ATC CAT G | Ldd1 | (SEQ ID NO: 22) |

A separate cDNA synthesis reaction with 0.1 μg polyA-RNA and Superscript II Reverse Transcriptase (Gibco/BRL) is carried out with each primer. Five percent of the cDNA product made with each member of a primer pair is mixed together with that primer pair for amplification in 30 PCR cycles using Klen Taq Polymerase Mix (Clontech). The PCR primers are used for cDNA synthesis to avoid the 3' bias imposed by oligo-dT primed cDNA synthesis. The relative orientation of the two primers in cDNA is randomized by carrying out a separate synthesis with each primer. These cDNA can be mixed in the same combinations as the primers chosen for PCR amplification. PCR amplified cDNA fragments are resolved on 6% acrylamide gels and dried for autoradiography. Those bands which are differentially displayed in at least 2 tumor samples and not in the parental cells are cut out and rehydrated. An aliquot (1/5) of the DNA recovered is reamplified using the same primer set and the same PCR conditions but without addition of isotope. This second PCR product is resolved on 1% agarose and individual bands are recovered by incubation with β agarase I (Gibco/BRL). Each DNA fragment recovered is cloned by blunt end ligation into the pcDNA3.1/Zeo (+) phagemid vector (Invitrogen). Since it is possible that a single band may include more than one molecular species, at least 4 different transformants with an insert of appropriate size are picked for further characterization. Northern analysis, RNase protection assays and semi-quantitative PCR are employed to confirm differential expression.

In murine tumor cell lines, it was observed that many more differentially expressed gene fragments appear to be identified by differential display than by RDA. In addition, RDA fragments give positive results on Northern blots exposed for only a few hours. In contrast, fragments identified by differential display often do not give a signal on Northern blots even after several days. Differential expression was, in this case, confirmed by Rnase protection and semi-quantitative PCR with sequence specific primers. These observations are consistent with the theoretical expectation that, because of the difficulty of driving hybridization of low abundance cDNA to completion, such sequences will be more readily identified by PCR based differential display than by hybridization based RDA. There may, in addition, be another reason for the greater sensitivity of modified differential display. It has been reported (Meyuhas and Perry, Cell 16:139–148 (1979)) that mRNA species of low abundance are on average twice the size of smaller, more stable and more abundant mRNA species. It is, therefore, more likely that both members of a pair of arbitrary primers will hybridize to and detect differentially expressed cDNA from the longer (average 4.9 kb) very diverse 80% of mRNA species that are represented by very few copies per cell than from the shorter (average 2 kb) 20% of mRNA species that are more abundantly expressed.

Figure 7:
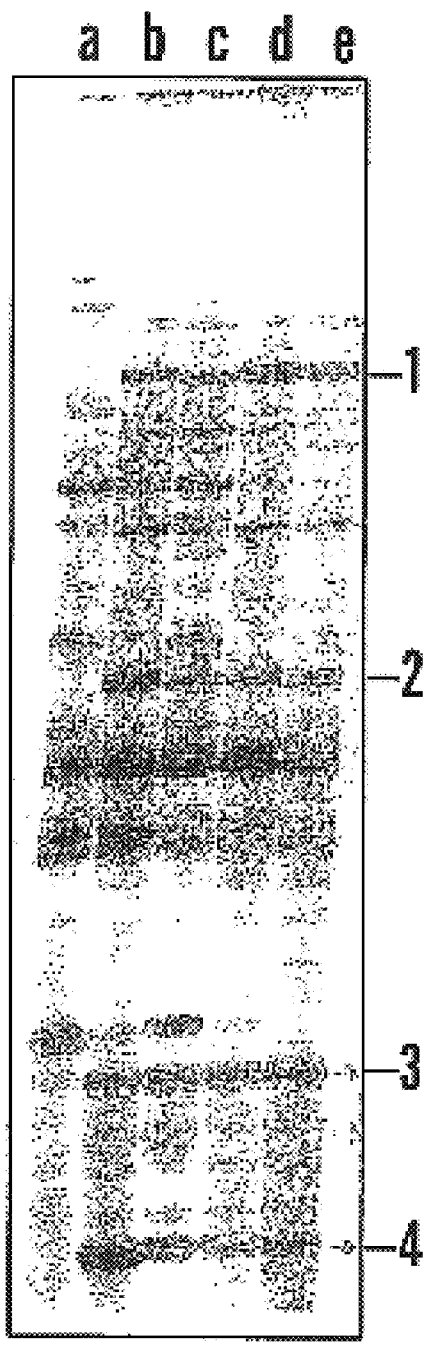
FIG. 7. Modified Differential Display of cDNA of parental cell B/c.N and tumors BCA 39, BCA 34, BCA 22, and BCB 13. Fragments of parental and tumor cell cDNA were amplified with one pair of arbitrary decamers, MR_1 (TAC AAC GAG G) (SEQ ID NO: 11) and MR_5 (GGA CCA AGT C)(SEQ ID NO: 13). For each cell line, first strand cDNA synthesis was separately primed with MR-1 or MR_5. The two cDNA preparations were then pooled for PCR amplification with both MR_1 and MR_5. A number of bands can be identified that are associated with all four tumors but not with the immortalized, non-tumorigenic parental cell line.

In preliminary experiments, an average of three differentially displayed bands were identified for each pair of primers. With a total of 66 primer pairs generated from all possible combinations of 12 independent primers, approximately 200 gene fragments could be identified. In some cases multiple fragments may derive from the same gene. FIG. 7 shows the pattern of differential display fragments observed with one pair of arbitrary decamers, MR_1 (TAC AAC GAG G) (SEQ ID NO:11) and MR_5 (GGA CCA AGT C) (SEQ ID NO:13). A number of bands can be identified that are associated with all four tumors but not with the parental cells. This distribution is unrelated to the immunogenicity of the tumor cells, since only three of the four tumors are immunologically crossreactive. In contrast to the differentially expressed bands identified by RDA, which gave positive results on the Northern blots exposed for only a few hours, fragments identified by differential display did not give a signal on Northern blots even after several days. Differential expression of the differential display fragments can, however, be confirmed by RNase protection assays or by semi-quantitative PCR with sequence specific primers. An example is shown in FIGS. 8A and 8B the results of an RNase protection assay with clone 90 from differential display band 9. This sequence, which has no significant homology to entries in the GenBank database, is expressed in all four tumor lines but not in the parental B/c.N.

As discussed above, we attribute this striking difference in the results of RDA and differential display to the greater sensitivity of the PCR based modified differential display as compared to the hybridization based RDA method. Based on the pattern of expression in the different tumor and normal cell lines, it appears that the shared tumor antigen detected following direct immunization of mice with syngeneic tumor cells may be encoded by a more abundantly expressed IAP gene. The methods described in this example can be used to determine whether the products of the less abundantly expressed genes identified by modified differential display represent potential cryptic tumor antigens.

Selection of Full Length cDNA Encoding Potential Tumor Immunogens

Figure 9:
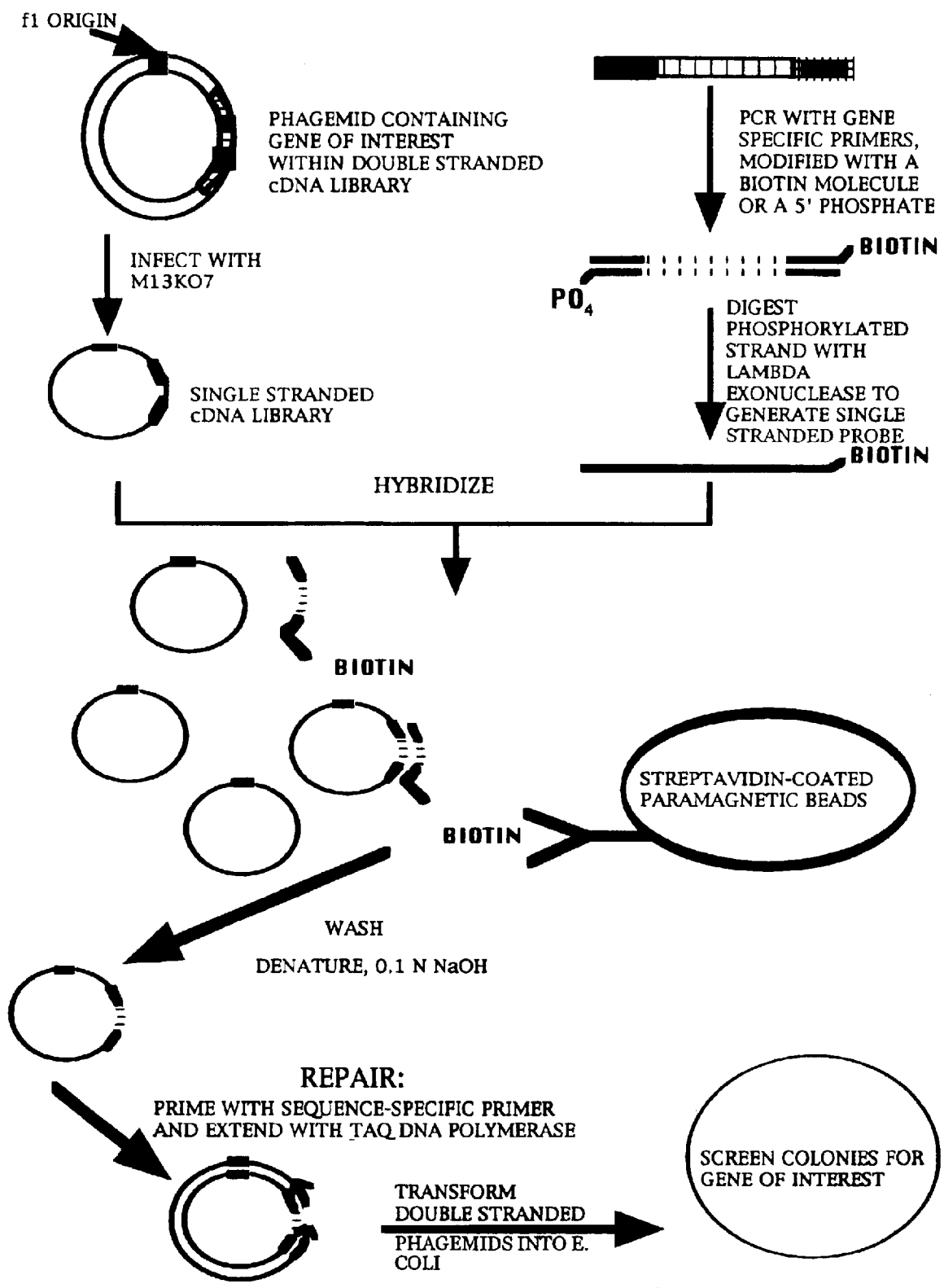
FIG. 9. Gene isolation in solution. Schematic of a method for selection of longer length cDNA from single strand circles rescued from a phagemid library. DNA fragments identified through RDA or Modified Differential Display are employed to select more full length cDNA.

This section presents methods for facilitating selection of corresponding full length cDNAs from fragments of differentially expressed genes identified by representational difference analysis or by modified differential display (FIG. 9). A single stranded biotinylated probe is synthesized from isolated cDNA fragments and is used to select the longer cDNA that contain a complementary sequence by solution hybridization to single stranded circles rescued from a phagemid tumor cDNA library. This method is especially well-suited to the use of DNA fragments isolated by the modified differential display method employing two arbitrary primers. The same arbitrary primers employed for PCR amplification of a given fragment in differential display can be modified to generate a single stranded hybridization probe from that fragment. This avoids the need to sequence, select and synthesize a new pair of fragment specific primers for each new fragment of interest.

i) The two oligonucleotides of a pair of PCR primers employed in differential display are modified: (biotin-dT)-dT-(biotin-dT) is incorporated at the 5' end of one primer and a phosphate is incorporated at the 5' end of the second primer. These modified primers are incorporated by PCR into the two strands of a differential display fragment that was selected following the original PCR amplification with the same unmodified arbitrary primers. From this double stranded PCR product, the strand labelled with a 5' phosphate is digested with λ exonuclease to generate a single stranded biotin-labeled probe.

ii) Single stranded (ss) DNA circles are rescued from a phagemid cDNA library using the M13K07 packaging defective phage as helper virus. This library is constructed in the pcDNA3.1/Zeo(+) phagemid (Invitrogen, Carlsbad, Calif.) with insertion of (ApaI)oligo-dT primed cDNA between the Apa I and Eco RV restriction sites. A key manipulation to achieve the efficient ligation necessary for construction of a high titer cDNA library is to insure that cDNA inserts are 5' phosphorylated by treating with T4 polynucleotide kinase prior to ligation. The biotin-labeled single stranded probe generated from the differential display fragment is hybridized in solution to the ssDNA circles of the phagemid library. The biotin-labeled hybridization complexes can then be separated from unrelated ssDNA on streptavidin magnetic beads and the ss circles eluted for further analysis (FIG. 9).

As a test of this enrichment method, a model plasmid mix was prepared that included 1% of a specific arbitrarily selected recombinant clone, 3fIAP. A biotinylated ss-probe was prepared from the 3f RDA fragment and used to select single stranded phagemid circles from the 1% plasmid mix. Following elution from streptavidin beads, the single stranded circles were hybridized to a sequence specific oligonucleotide in order to prime synthesis of the second plasmid strand prior to bacterial transformation. Plasmid DNA was prepared from 63 transformed colonies. 63 of 63 of these plasmid preparations expressed the target 3F IAP insert. This method therefore appears to be very efficient.

The same method appears to work with similar efficiency in the more stringent case of a differential display fragment (B4) representing a previously unidentified sequence that is expressed in all four murine tumors at a concentration approximately 10 fold greater than in the non-tumorigenic parental cells. 5 out of 5 transformants randomly picked following selection of single strand circles with the 200 bp B4 DNA fragment had longer inserts that were positive by PCR with sequence specific primers. This method therefore appears to be very efficient.

EXAMPLE 5

Independent Human Tumor Cell Lines Derived from a Non-tumorigenic, Immortalized Cell Line The following example describes a set of human tumors independently derived by different carcinogens or oncogene transformation from the same cloned, non-tumorigenic parental cell line. As in the previous examples of the use of RDA and modified differential display for identification of gene products differentially expressed in murine tumors, the availability of related normal and tumor cell lines has considerable advantages for the molecular and immunological analysis of potential cancer vaccines. This not only provides a readily available source of normal control cells and RNA, but also makes it possible to focus on molecular features that are carcinogen independent and, since they are shared by multiple independent tumors, are unlikely to be the products of random genetic drift during in vitro propagation.

A set of human uroepithelial tumors have been derived in the laboratory of Dr. Catherine Reznikoff (University of Wisconsin, Madison) from an SV40 immortalized human uroepithelial cell line, SV-HUC, that is itself contact inhibited, anchorage dependent and non-tumorigenic in nude mice (Christian, et al., Cancer Res. 47:6066–6073 (1987)). A series of independent tumor cell lines were derived by either ras transformation (Pratt, et al., Cancer Res. 52:688–695 (1992)) or in vitro mutagenesis of SV-HUC with different carcinogens including some that are bladder-specific (Bookland, et al., Cancer Res. 52:1606–1614 (1992)). Transformed cells were initially selected on the basis of altered in vitro growth requirements and each was shown to be tumorigenic in nude mice. A subset of these tumors is selected that retain the phenotype of transitional cell carcinoma. Table 7 lists the parental cells and the carcinogens employed to derive these 5 tumor lines in vitro. A systematic program is undertaken to 1) identify full length cDNA differentially expressed in these tumors and 2) to test the immunogenicity in HLA and human CD8 transgenic mice of these cDNA products cloned into a vaccinia virus expression vector.

TABLE 7

Human Uroepithelial Cell Lines
Acquired from Dr. Catherine A. Reznikoff,
University of Wisconsin Clinical Cancer Center

| Parental Line | Immortalization |
| --- | --- |
| SV-HUC | SV40 immortalized normal bladder epithelial cells |
| Tumor Line | Carcinogen or Oncogene transformation |
| MC pT7 | 3-methylcholanthrene |
| MC ppT11-A3 | 3-methylcholanthrene followed by 4-aminobiphenyl |
| MC ppT11-HA2 | 3-methylcholanthrene followed by N-hydroxy-4-acetylaminobiphenyl |
| HA-T2 | N-hydroxy-4-aminobiphenyl |
| SV-HUC/ras-T | EJ/ras |

Experiments apply both representational difference analysis and modified differential display to identify gene fragments differentially expressed in the MC ppT11-A3 tumor (ppT11A3) relative to the parental SV-HUC. All differentially expressed fragments are tested by Northern analysis and RNase protection assay for parallel expression in mRNA of the other tumor cell lines. Only those DNA clones expressed in at least 3 of the 5 SV-HUC derived tumor cell lines are selected for further characterization.

Similar analysis of tumor-specific gene products can be carried out with tumors derived from SV40 large T or HPV E6 or E7 immortalized cell lines representative of other human tissues. Published examples include: prostatic epithelium (Parda et al., The Prostate 23:91–98 (1993)), mammary epithelium (Band et al., Cancer Res. 50:7351–7357 (1990)), and bronchial epithelium (Gerwin et al., Proc. Natl. Acad. Sci. USA 89:2759–2763 (1992); Klein-Szanto et al., Proc. Natl. Acad. Sci. USA 89:6693–6697 (1992)).

EXAMPLE 6

Gene Expression in Fresh Patient Bladder Tumors

The above-described methods for identification of differentially expressed genes require that both tumor and normal control cell mRNA be readily available. The preceding section focuses on tumors derived in vitro from immortalized cell lines, from which mRNA may be readily obtained in large quantities.

In spite of the advantages of working with in vitro-derived tumors from which mRNA may be readily obtained, it is necessary to address the possibility that some transformation-associated gene expression might be missed or, conversely, that some differential gene expression detected might not be transformation related. Although the normal control is contact inhibited, anchorage dependent and non-tumorigenic, it is likely that it has undergone some pre-neoplastic event that is the basis for continuous growth in vitro. Perhaps a greater concern is that extraneous gene expression associated with in vitro proliferation might be identified. Two strategies to exclude such events are employed. First, genes are analyzed that are expressed in at least 3 of the 5 bladder tumor lines but that are not expressed in the in vitro adapted parental cells. This will a) filter out any systematic gene expression selected by in vitro growth, since this should be shared by the normal parental cells; and b) identify any alterations in gene expression that are carcinogen specific or that may arise as a result of random genetic drift during in vitro propagation, since it is not expected that these would be shared by multiple independent tumors derived by diverse carcinogens (or oncogene transformation). Second, and most important, only those differentially expressed genes that can also be shown to be expressed in multiple samples of fresh patient tumor material are selected for further characterization.

Patient tumor material together with normal bladder epithelium is cryopreserved following surgery. In comparison to some other carcinomas, normal tissue control is readily available from bladder cancer patients. Total RNA is extracted from frozen samples by the acid guanidinium isothiocyanate method (Lee and Costlow, *Methods in Enzymology* 152:633–648 (1987)). Following Dnase I treatment, polyA mRNA is fractionated on oligo dT beads and gene expression is analyzed by Northern blot, RNase protection assay, and semi-quantitative RT/PCR. For each differentially expressed gene fragment identified in the in vitro tumor lines, expression of the gene is characterized in a panel of 20 patient tumors and normal tissue controls. This sample size permits the estimation of the proportion of patients expressing the gene with a standard error no greater than 0.11% (SE=sqrt[p*(1−p)/n] where p=true proportion and n=sample size. SE is maximal for p=0.5, at that proportion, 10/20 patients, SE=±0.11; for any other value of p, SE is smaller.) Expression of some of these genes may be correlated in the different tumor samples. This is useful because it creates the possibility of multiple T cell epitopes that could associate with different human MHC molecules.

The expression pattern is also determined, in other normal adult and fetal tissues, of any gene that is differentially expressed in bladder tumors relative to normal bladder epithelium. Total RNA or first strand cDNA prepared from over 30 different human normal adult or fetal tissues (Discovery Line™ RNA and Gene Pool™ cDNA, Invitrogen, Carlsbad, Calif.) is used. Expression in fetal but not normal adult tissue is particularly interesting and does not preclude consideration as an immunotherapeutic reagent. Expression of intermediate abundance species are determined by Northern analysis. Low abundance species are quantitated by RNase protection assay and semi-quantitative PCR. Those sequences that are recurrently expressed in tumors derived from multiple patients and which have the lowest relative expression in normal tissue are selected for further characterization as potential tumor-specific antigens.

EXAMPLE 7

The Use of Differentially Expressed Gene Products to Generate CTLs Crossreactive with Authentic Tumors To identify differentially expressed gene products that might be candidates for tumor immunotherapy, it is necessary to have a means of delivering the product for immunization in an environment in which T cell responses to peptides associated with human HLA can be induced. T cells induced by immunogenic products could then be tested for crossreactivity on HLA compatible tumors that express the corresponding mRNA. This example describes the use of HLA and human CD8 transgenic mice for induction of T cell responses to peptides associated with human HLA. If all these conditions are met: 1) the gene is differentially expressed in multiple human tumors but not normal tissue counterparts; 2) gene products are immunogenic in association with HLA; and 3) the specific T cells induced are crossreactive on human tumor cells, then this would constitute key preliminary data preparative to initiation of clinical vaccine trials.

To determine whether the products of differentially expressed genes are immunogenic, groups of three (HLA-A2.1×huCD8)$F_1$ transgenic mice are immunized intravenously with 5×10$^6$ pfu of each specific recombinant vaccinia virus (Bennink and Yewdell, *Current Topics in Microbiol. and Immunol.* 163:153–178 (1990)). After at least two weeks, mice are sacrificed and CD8+ splenic T cells are enriched on anti-CD8 coated magnetic beads. CD8+ cytolytic precursors are restimulated in vitro with parental SV-HUC cells that are transfected with the recombinant differentially expressed gene previously isolated in the pcDNA3.1/Zeo(+) plasmid expression vector (Example 4). Substitution of the plasmid recombinant in place of the vaccinia vector for restimulation in vitro is necessary to avoid a large vaccinia vector specific response. After five days in vitro culture, cytolytic activity is determined by $^{51}$Cr release from SV-HUC target cells transfected with either the specific recombinant plasmid or a control ovalbumin gene recombinant.

This same cytolytic assay can be readily applied to determine whether the relevant CTL epitope is also presented by HLA compatible tumor cells that express the corresponding mRNA. If T cells are induced in (HLA-A2.1× huCD8)$F_1$ transgenic mice, HLA compatible targets include tumor cells that either express native HLA-A2.1 or that have been transfected with HLA-A2.1. The immunogenicity of differentially expressed gene products is established and it is determined whether there is a crossreaction with human tumor cells. This finding, together with the demonstration that the same mRNA is expressed in multiple samples of fresh patient tumors but not normal tissues (Example 6), is required prior to initiation of a clinical vaccine trial.

An important consideration for vaccine development is the extensive polymorphism of human class I HLA. As discussed above, an appealing strategy is to target four major HLA subtypes, A2, A3, B7 and B44, that provide broad coverage across ethnic populations. Many peptides bind to multiple members of a single subtype. If several CTL epitopes are identified for each subtype, then this can greatly facilitate formulation of a broadly effective vaccine.

EXAMPLE 8

Induction of Protective Immunity

It is desirable, especially in the case of cryptic tumor antigens encoded by low abundance mRNA, to determine whether a T cell response to differentially expressed gene products confers protective tumor immunity. Since a number of differentially expressed genes have been identified in the murine tumor model described above, such experiments are carried out in mice.

It has previously been reported for this murine tumor model (Sahasrabudhe, et al., *J. Immunology* 151: 6302–6310 (1993)) that three of four independently derived tumors are immunologically crossreactive. Many of the differentially displayed bands identified in these tumors are, in contrast, present in all four tumors. It is, therefore, unlikely that the genes from which these fragments derive are immunologically dominant in animals inoculated with these tumors.

If it is shown that direct immunization with a recombinant differentially expressed gene does, nevertheless, confer protective immunity, then this provides compelling evidence for the efficacy of vaccination with a cryptic tumor antigen.

Groups of 5 mice of the BALB/c strain syngeneic to the murine tumors are immunized with each vaccinia virus recombinant for a full length cDNA differentially expressed in all four murine tumor lines but not the parental B/c.N cells (FIG. 7). Each group of mice is assayed for induction of protective immunity by challenge with a tumorigenic inoculum of $1 \times 10^6$ BCA 39 tumor cells (Sahasrabudhe, et al., *J. Immunology* 151:6302–6310 (1993)). To determine whether protective immunity correlates with relative quantitative expression, independent gene products are tested that represent different levels of differential expression as determined by semi-quantitative PCR.

EXAMPLE 9

Construction and Characterization of Vaccinia Expression Vectors for Use in Vaccines This example describes the construction and characterization of a new set of direct ligation vectors designed to be universally applicable for the generation of chimeric vaccinia genomes. The aim was to modify the genome of vNotI/tk so as to acquire direct ligation vectors which are more universally useful. First, the insertion site was changed by placing the sites for two unique restriction enzymes at the beginning of the thymidine kinase gene. This allows one to fix the orientation of the insert DNA and eliminates the production of contaminating wild type genomes after religation of viral arms. Second, in order to generate a direct ligation vector which would express high levels of protein, the thymidine kinase gene was preceded by a strong constitutive vaccinia virus promoter.

These new ligation vectors contain a pair of unique restriction sites, NotI and ApaI, to eliminate religation of poxvirus arms and fix the orientation of the insert DNA behind strongly expressing constitutive vaccinia promoters. The insertion cassette has been placed at the beginning of the thymidine kinase gene in vaccinia to utilize drug selection in the isolation of recombinants.

Materials and Methods

Plasmid Construction

Pairs of oligonucleotides were constructed which, when annealed, contained the 7.5 k gene promoter (MM436:GGCCAAAAATTGAAAAACTAGATCTATTTA-TTGCACGCGGCCGCCATGGGCCC (SEQ ID NO:23) and MM437: GGCCGGGCCCATGGCGGCCGCGTG-CAATAAATAGATCTAGTTTTTCAATTTTT (SEQ ID NO:24)), or the synthetic EL promoter (MM438:GGCCAAAAATTGAAATTTTATTTTTTTTTTT-TGGAATATAAAGCGGCCGCCAT GGGCCC (SEQ ID NO:25) and MM439: GGCCGGGCCCATGG-CGGCCGCTTTATATTCCAAAAAAAAAAAATAAAAT-TTCAATTTTT (SEQ ID NO:26)) and restriction sites for NotI and ApaI. The double-stranded oligonucleotides were annealed by ramping from 94° C. to 20° C. over two hours and ligated into the NotI site present in pJNotI/tk, a plasmid containing the HindIII J fragment from vNotI/tk, resulting in plasmids p7.5/tk and pEL/tk.

A Polymerase Chain Reaction (PCR) was performed on pBI221, a plasmid containing the *E.coli* gusA gene encoding for β-glucuronidase (β-glu), using primers MM440 (GGGAAAGGGGCGGCCGCCATGTTACGTCCTGTAG-AAACC) (SEQ ID NO.27) and MM441 (GGGAAAGGGGGGCCCTCATTGTTTGCCTCCCTGC-TG)(SEQ ID NO:28), or MM440 and MM442 (GGGAAAGGGGCGGCCGCCTCATTGTTTGCCTCCC-TGCTG) (SEQ ID NO:29), and the resulting fragment was cloned into pCRII (TA cloning kit, Invitrogen). The plasmids were excised with NotI (MM440/MM442 product) and cloned into pJNot/tk digested with NotI yielding pJNot/tk–GUS, or excised with NotI and ApaI (MM440/MM441 product), and inserted into pEL/tk and p7.5/tk previously digested with ApaI and NotI yielding p7.5/tk–GUS and pEL/tk–GUS.

Pairs of oligonucleotides were constructed which, when annealed, contained the 7.5 k gene promoter and the nucleotide sequence encoding for a cytotoxic T-cell epitope for ovalbumin (11) (SIINFEKL; SEQ ID NO:10) (75ova: GGCCAAAAATTGAAAAACTAGATCTATTTATTGC-ACCATGAGTATAATCAACTTTGAAAAACTGTAGTGA (SEQ ID NO:30) and 75ovary: GGCCTCACTACAGTTTTTCAAAGTTGATTAATACTC-ATGGTGCA- ATAAATAGATCTAGTTTTTCAATTTTT (SEQ ID NO:31)) or the EL promoter and the peptide SIINFEKL (SEQ ID NO:10) (ELova: GGCCAAAAATTGAAATTTTATTTTTTTTTTTGGAAT-ATAAACC- ATGAGTATAATCAACT TTGAAAAACTG-TAGTGA (SEQ ID NO:32) and ELovarv: GGCCTCACTACAGTTTTTCAAAGTTGATTATACTCA-TGGTTTATATTCCAAAAAAAAAAAATAAAATTTCAA-TTTTT(SEQ ID NO:33)). The double-stranded oligonucleotides were annealed by ramping from 94° C. to 20 ° C. over two hours and ligated into the NotI site present in pJNotI/tk, a plasmid containing the HindIII J fragment from vNotI/tk resulting in plasmids p7.5/tk–ova and pEL/tk–ova.

Generation of Recombinant Viruses

Cells and viruses were maintained and manipulated as described by Earl, et al. (in *Current Protocols in Molecular Biology*, Ausubel, et al., eds., Greene Publishing Associates/Wiley Interscience, New York (1991)). Recombinant viruses were made using homologous recombination by infecting CV-1 cells at a multiplicity of infection (moi) of 0.05 and two hours later transfecting DNA into the infected cells using lipofectamine (Life Technologies Incorporated) as suggested by the manufacturer. After 72 hours the cells were harvested and isolated plaques were selected by passage in Hutk cells in the presence of bromodeoxyuridine (Earl, et al., in *Current Protocols in Molecular Biology*, Ausubel, et al., eds., Greene Publishing Associates/Wiley Interscience, New York (1991)) or HAT supplemented media (Weir, et al., 1982, Proc. Nat. Acad. Sci. USA, 79:1210–1214).

Vaccinia virus was generated from viral DNA by rescue with fowlpox virus (Scheiflinger, et al., *Proc. Natl. Acad. Sci. USA* 89:9977–9981 (1992)). Vaccinia virus was isolated from infected HeLa cells by banding and sedimentation in sucrose (Earl, et al., in *Current Protocols in Molecular Biology*, Ausubel, et al., eds., Greene Publishing Associates/Wiley Interscience, New York (1991)). The purified virions were treated with Proteinase K (Boehringer Mannheim) and gently extracted with buffer saturated phenol, phenol:chloroform (50:50), and chloroform before precipitation with 2.5 volumes of ethanol in 0.3M sodium acetate and resuspended in TE (10 mM TrisHCl, pH8.0. 1 mM EDTA (Earl, et al., in *Current Protocols in Molecular Biology*, Ausubel, et al., eds., Greene Publishing Associates/Wiley Interscience, New York (1991)). Confluent wells of BSC-1 cells from a 12 well dish were infected with fowlpox virus and after a two hour incubation at 37° C. were transfected with 0.6 μg full length vaccinia DNA using Lipofectamine (Life Technologies Incorporated) as suggested by the manufacturer. After 24, 48, and 72 hours the cells were harvested, lysed by three freeze-thaw cycles and screened by plaque assay on BSC-1 cells (Earl, et al., in *Current Protocols in Molecular Biology*, Ausubel, et al., eds., Greene Publishing Associates/Wiley Interscience, New York (1991)).

Generation of Recombinant Viruses by Direct Ligation

The 1.1 kB Eco RI/Eco RV restriction endonuclease fragment containing ovalbumin from pHbeta-Ova-neo (Pulaski, et al., 1996, Proc. Natl. Acad. Sci. USA, 93:3669–3674) was inserted into the EcoRI and EcoRV sites of pBluescript KS+ (Stratagene), generating pBS.ova. The DNA product from a Polymerase Chain Reaction (PCR) on pBS.ova using primers VVOLZ5 (GCAGGTGCGG-CCGCCGTGGATCCCCGGGCTGCAGG) (SEQ ID NO:34) and VVTLZ3 (GTACCGGGCCCACAAAAA-CAAAATTAGTTAGTTAGGCCCCCCCTCGA) (SEQ ID NO:35) was digested with ApaI and NotI (Life Technologies, Inc.), gel purified from low melting point agarose (Bio-Rad) using beta Agarase (Life Technologies, Inc.) following the recommendations of the manufacturer, and cloned into pBluescript KS+ that had been digested with NotI and ApaI, generating pBS.VVova. A DNA fragment encoding ovalbumin was excised from pBS.VVova by digestion of this plasmid with ApaI and NotI and purified after electrophoresis through a low melting point agarose gel using beta Agarase. One microgram of purified vEL/tk DNA was digested with ApaI and NotI and centrifuged through a Centricon 100 concentrator (Amicon) to remove the small intervening fragment. The vEL/tk DNA arms and the DNA fragment encoding ovalbumin were ligated overnight at room temperature, at a 4:1 (insert: virus) molar ratio, in 30 microliters with 5 units T4 DNA Ligase. The ligation product was transfected using lipofectamine (Life Technologies, Inc.) into a well of confluent BSC-1 cells from a 12 well plate two hours after infection with fowlpox virus at 1 pfu/cell. Three days later the cells were harvested and isolated plaques were selected by passage in Hutk– cells in the presence of bromodeoxyuridine (Earl, et al., in *Current Protocols in Molecular Biology*, Ausubel, et al., eds., Greene Publishing Associates/Wiley Interscience, New York (1991)).

Analysis of Viral DNA Genomes

BSC-1 cells were infected at high multiplicity of infection (moi) by vaccinia WR, vEL/tk, v7.5/tk, or vNotI/tk. After 24 hours the cells were harvested and resuspended in Cell Suspension Buffer (Bio-Rad Genomic DNA Plug Kit) at 1×10$^7$ cells/ml. An equal volume of 2% CleanCut agarose (Bio-Rad) preincubated at 50° C. was added and the cell suspension was formed into 100 μl plugs. After hardening at 4° C. the plugs were treated as previously described to digest protein (Merchlinsky, et al., *J. Virol.* 63:1595–1603 (1989)). The plugs were equilibrated in the appropriate restriction enzyme buffer and 1 mM PMSF for 16 hours at room temperature, incubated with restriction enzyme buffer, 100 ng/ml Bovine Serum Albumin and 50 units NotI or ApaI for two hours at 37° C. (NotI) or room temperature (ApaI) prior to electrophoresis.

One well of a 6 well dish of BSC-1 was infected with v7.5/tk or vEL/tk at high multiplicity of infection (moi) and after 48 hours the cells were harvested, pelleted by low speed centrifugation, rinsed with Phosphate-Buffered Saline (PBS), and the DNA was isolated using DNAzol (Gibco). The final DNA product was resuspended in 50 microliters of TE (10 mM TrisHCl, pH 8.0, 1 mM EDTA) and 2.5 microliters were digested with HindIII, HindIII and ApaI, or HindIII and NotI, electrophoresed through a 1.0% agarose gel, and transferred to Nytran (Schleicher and Schuell) using a Turboblotter (Schleicher and Schuell). The samples were probed with p7.5/tk (FIG. 11A) or pEL/tk (FIG. 11B) labeled with $^{32}$P using Random Primer DNA Labeling Kit (Bio-Rad) in QuickHyb (Stratagene) and visualized on Kodak XAR film.

One well of a 6 well dish of BSC-1 cells was infected with v7.5/tk or vEL/tk, vNotI/tk, vpNotI, vNotI/lacZ/tk, or wild type vaccinia WR at high multiplicity of infection (moi) and after 48 hours the cells were harvested, pelleted by low speed centrifugation, rinsed with Phosphate-Buffered Saline (PBS), and the DNA was isolated using DNAzol (Gibco). The final DNA product was resuspended in 50 microliters of TE (10 mM TrisHCl, pH8.0. 1 mM EDTA) and used in a PCR (30 cycles, 1 minute 94° C., 2 minutes 55° C., 3 minutes 72° C., MJ Research PTC-100) with primers MM407 (GGTCCCTATTGTTACAGATGGAAGGGT) (SEQ ID NO:36) and MM408 (CCTTCGTTT-GCCATACGCTCACAG) (SEQ ID NO:37). The nucleotide sequence was determined by $^{35}$S sequencing using Sequenase Version 2.0 DNA Sequencing Kit (Amersham), and visualized after electrophoresis through 8% denaturing polyacrylamide gels by exposure to Bio-Max film (Kodak).

Determination of β-glucuronidase Activity

A well of BSC-1 cells from a 12 well plate was infected at an moi of 1 with vNotI/tk–GUS, v7.5/tk–GUS and vEL/tk–GUS, the cells were harvested 20 hours post infection, resuspended in 0.5 ml PBS, and disrupted by three cycles of freeze-thawing. The extract was clarified by a short microfuge spin (one minute, 14,000 rpm) and the supernatant was analyzed for β-glu units as described by Miller, *Experiments in Molecular Genetics*, Cold Spring Harbor Laboratory, Cold Spring Harbor, N.Y. (1972), as adapted for 96-well plates. The $A_{405}$ values were determined on a microplate reader (Dynatech MR3000) and the β-glu activity was determined by comparison to β-glu (Clontech) standards analyzed in the same assay.

Analysis of Cytoxic T Cell Response

Confluent monolayers of MC57G cells in wells of a 6 well plate were infected at an moi of 1 with vEL/tk, v7.5/tk–ova, vEL/tk–ova, vEL/tk–ovaFL clone 1, and vEL/tk–ovaFL clone 2 (vEL/tk–ovaFL are virus clones of full length ovalbumin generated by direct ligation). At 16 hours post infection cells were harvested, labeled with 100 microcuries $^{51}$Chromium (Dupont) for 1 hour at 37° C., and 10$^4$ cells were added to wells of a 96 well round bottom plate in quadruplicate. A sample of uninfected MC57G cells incubated with 1 micromolar purified ova 257–264 peptide was also incubated with $^{51}$Cr as a positive control and untreated MC57G cells were used as a negative control. T cells specific for ova 257–264 were added to target cells at ratios of 2:1 and 10:1. Cells were incubated at 37° C. for 4 hours, supernatants were harvested, and $^{51}$Cr release determined. Spontaneous release was derived by incubating target cells with media alone and maximal release was determined by incubating target cells with 5% Tritonx100. Percentage of specific lysis was calculated using the formula: % specific lysis=((experimental release-spontaneous release)/(maximal release-spontaneous release))×100. In each case the mean of quadruplicate wells was used in the above formula.

Results

Construction of Direct Ligation Vectors

The vaccinia WR genome is approximately 190 kilobases in length and rich in A and T residues. The complete sequence of the vaccinia WR genome was provided by P. Earl of the Bernard Moss laboratory (Laboratory of Viral Diseases, NIAID, NIH, Bethesda, Md.). A restriction enzyme search of the complete sequence of the vaccinia WR genome using MacVector (IBI) revealed a lack of restriction sites for ApaI, AscI, Bsp120I, FseI, RsrII, SfiI, SrfI and SgfI. The ready availability of highly active and pure preparations of the enzyme as well as the generation of a staggered end upon digestion led us to choose to use ApaI as the second site in conjunction with the NotI site already present in vNot/tk.

Vaccinia virus based expression vectors are most useful when the foreign protein is expressed constitutively. The expression of foreign proteins during the early stage of viral replication is essential for cytotoxic T cell response (Bennick, et al. *Topics Microbiol. Immunol.* 163:153–184 (1990)) and high levels of total protein expression have been observed using promoters active during the late stage of viral replication. We decided to incorporate the promoters corresponding to the constitutively expressed 7.5 k gene (Mackett, et al., *J. Virology*, 49:857–864 (1984)) and a constitutively expressed synthetic promoter EL noted for high level expression.

A useful feature of vNotI/tk that must be retained in any new vector is the ability to discriminate for recombinant viral genomes using selection against an active thymidine kinase gene. The introduction of the ApaI site within the coding sequence for the tk gene necessitates an increase in the total number of amino acids in order to accommodate the restriction enzyme site. A comparison of the amino acid sequence for thymidine kinase genes from a variety of animal and viral species showed the region of greatest heterogeneity was at the N terminus of the protein, suggesting that this region of the protein could tolerate a modest increase in the number of amino acids.

The recombination-independent cloning vectors were constructed by making plasmid intermediates containing the modified thymidine kinase (tk) gene and replacing the tk sequence in the vNotI/tk genome by homologous recombination. Two sets of oligonucleotide pairs were constructed which, when annealed, contained the promoter for the 7.5 k gene or the synthetic EL sequence and restriction sites for NotI and ApaI. The modified thymidine kinase genes were constructed by annealing the double-stranded oligonucleotides and ligating the product into the NotI site present at the beginning of the thymidine kinase gene in pJNotI/tk, a plasmid containing the HindIII J fragment from vNotI/tk. The oligonucleotide pairs annealed to and eliminated the NotI site in pJNotI/tk generating a new NotI site closely followed by an ApaI site after the promoter and flanking the nucleotides coding for the initial methionine in the thymidine kinase gene resulting in plasmids p7.5/tk (SEQ ID NO:1) and pEL/tk (SEQ ID NO:3) (FIG. 1). The acquisition of the ApaI site was verified by restriction enzyme analysis of plasmid DNA and the nucleotide sequence of the thymidine kinase gene promoter was determined and found to be as depicted in FIG. 1.

The recombinant viruses derived from p7.5/tk and pEL/tk were isolated using a strategy relying on positive drug selection in the presence of HAT (hypoxanthine, aminopterin, thymidine) (Weir, et al., *Proc. Nat. Acad. Sci. USA* 79:1210–1214 (1982)). The viruses vpNotI, a virus that contains a copy of pBR322 inserted at the NotI site of vNotI/tk (Merchlinsky, et al., *Virology* 190:522–526 (1992)), and vNotI/lacZ/tk, a virus with a copy of the lacZ gene interrupting the thymidine kinase in vNotI– (Merchlinsky, et al., *Virology.* 190:522–526 (1992)) are thymidine kinase negative (tk–) viruses that are identical to vNotI/tk except for the inserted DNA at the beginning of the tk gene. The plasmids p7.5/tk and pEL/tk were recombined with vpNotI and vNotI/lacZ/tk helper viruses in CV-1 cells and the infected monolayers were harvested and passaged in the presence of HAT media on Hutk⁻ cells. Individual plaques were passaged and isolated an additional three rounds on Hutk⁻ cells before expansion and analysis.

Analysis of the Structure of the Viral Genomes

Figure 10:
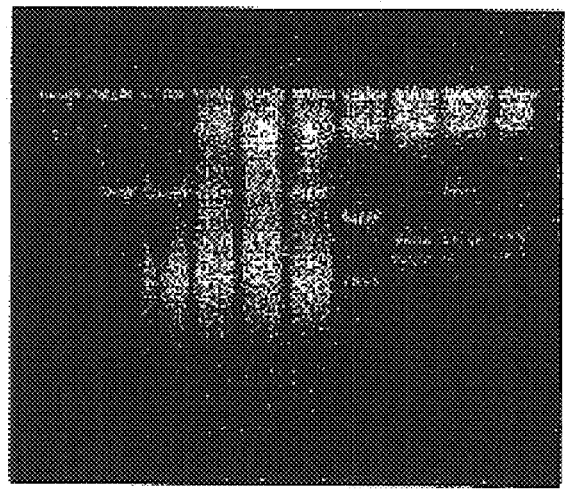
FIG. 10. Restriction Enzyme Analysis of Virus Genomes Using CHEF Gel. BSC-1 cells were infected at high multiplicity of infection (moi) by vaccinia WR, vEL/tk, v7.5/tk, or vNotI/tk. After 24 hours the cells were harvested and formed into agarose plugs. The plugs were equilibrated in the appropriate restriction enzyme buffer and 1 mM PMSF for 16 hours at room temperature, incubated with restriction enzyme buffer, 100 ng/ml Bovine Serum Albumin and 50 units NotI or ApaI for two hours at 37° C. (NotI) or room temperature (ApaI) and electrophoresed in a 1.0% agarose gel on a Bio-Rad CHEFII apparatus for 15 hours at 6 V/cm with a switching time of 15 seconds. The leftmost sample contains lambda DNA, the second sample contains undigested vaccinia DNA, and the remainder of the samples contain the DNA samples described above each well digested with ApaI or NotI where vEL refers to vEL/tk and v7.5 refers to v7.5/tk. The lower portion of the figure is a schematic map showing the location of the NotI and ApaI sites in each virus.
Figure 10:
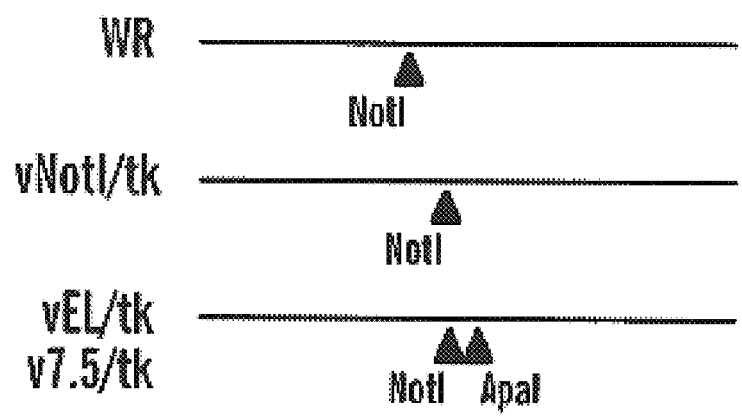

The growth of v7.5/tk and vEL/tk virus in HAT supplemented media implies these viruses, in contrast to vpNot and vNot/lacZ/tk, contain an active thymidine kinase (tk) gene. However, an active tk gene could arise from multiple crossovers which delete the 7.5 k or EL promoter sequences, generating a virus with the normal tk promoter. The v7.5/tk and vEL/tk genomes should contain a unique site for both NotI and ApaI within the HindIII J fragment. The genomic structure of the isolated virus stocks was analyzed by restriction enzyme digestion of DNA in agarose plugs derived from virus infected cells using NotI or ApaI and electrophoresis of the products through 1% agarose (FIG. 10). Uncut vaccinia WR (lane 2) migrates at a size of 190 kilobase pairs as compared to multimers of bacteriophage lambda (lane 1). After digestion with NotI vaccinia WR is cleaved into two fragments approximately 150 and 40 kilobase pairs in length (7th lane from left) whereas the vNot/tk, vEL/tk, and v7.5/tk were cleaved into fragments of about 110 and 80 kilobase pairs. When the same samples were digested with ApaI, only one fragment the size of the uncut genome was observed for both vaccinia WR and vNot/tk while vEL/tk and v7.5/tk gave the same sized fragments observed after digestion with NotI. Therefore, both v7.5/tk and vEL/tk contain a unique site for both ApaI and NotI, the sites are at the same locus as the NotI site in vNot/tk, and the sites are in a more central location in the genome than the HindIII F fragment which contains the NotI site in vaccinia WR. The background of cellular DNA fragments was more pronounced in the ApaI digestion, which has a six base pair recognition site, than for the NotI digest.

Figure 11A:
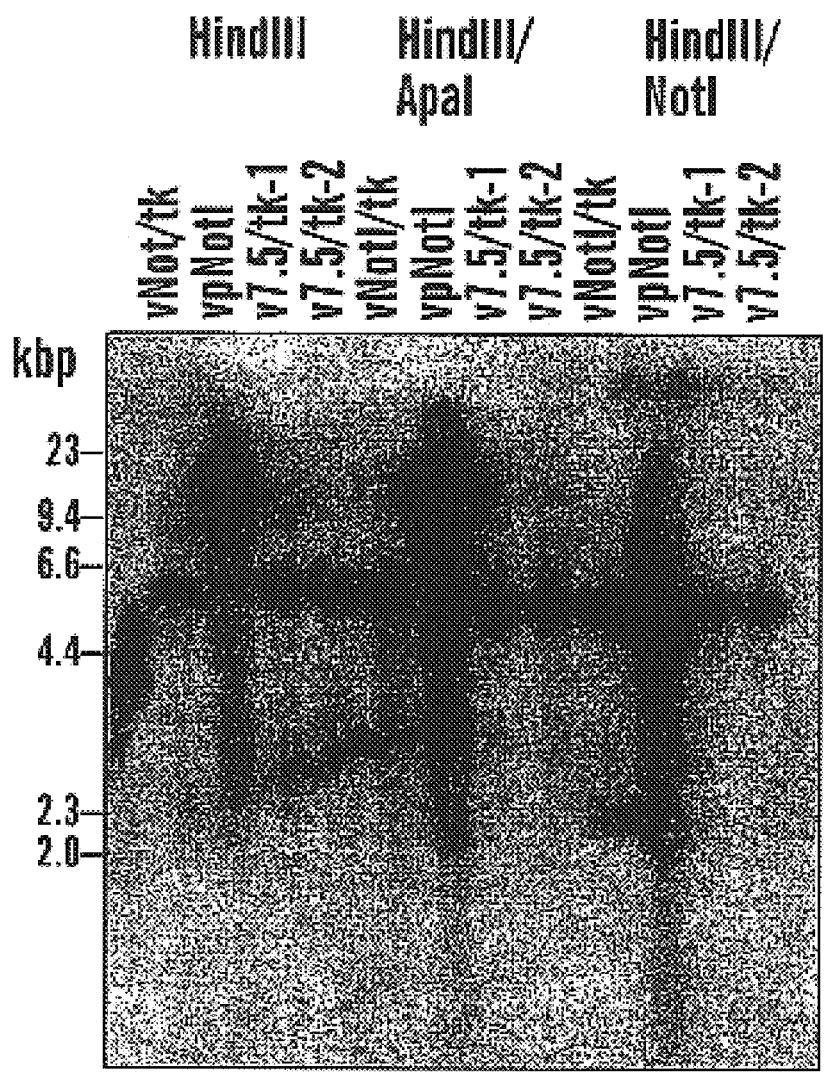
FIGS. 11A and 11B. Southern Blot Analysis of Viral Genomes p7.5/tk FIG. 11A) and pEL/tk (FIG. 11B). The viruses v7.5/tk and vEL/tk were used to infect a well of a 6 well dish of BSC-1 cells at high multiplicity of infection (moi) and after 48 hours the cells were harvested and the DNA was isolated using DNAzol (Gibco). The final DNA product was resuspended in 50 microliters of TE 8.0 and 2.5 microliters were digested with HindIII, HindIII and ApaI, or HindIII and Not I, electrophoresed through a 1.0% agarose gel, and transferred to Nytran (Schleicher and Schuell) using a Turboblotter (Schleicher and Schuell). The samples were probed with p7.k/tk (FIG. 11A) or pEL/tk (FIG. 11B) labeled with $^{32}P$ using Random Primer DNA Labeling Kit (Bio-Rad) in QuickHyb (Stratagene). The lower portion of the figure denotes a map of the HindIII J fragment with the positions of the HindIII, NotI, and ApaI sites illustrated. The leftmost 0.5 kilobase fragment has electrophoresed off the bottom of the gel.
Figure 11A:
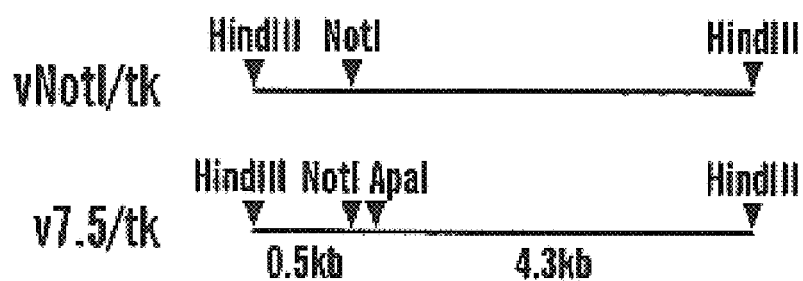
Figure 11B:
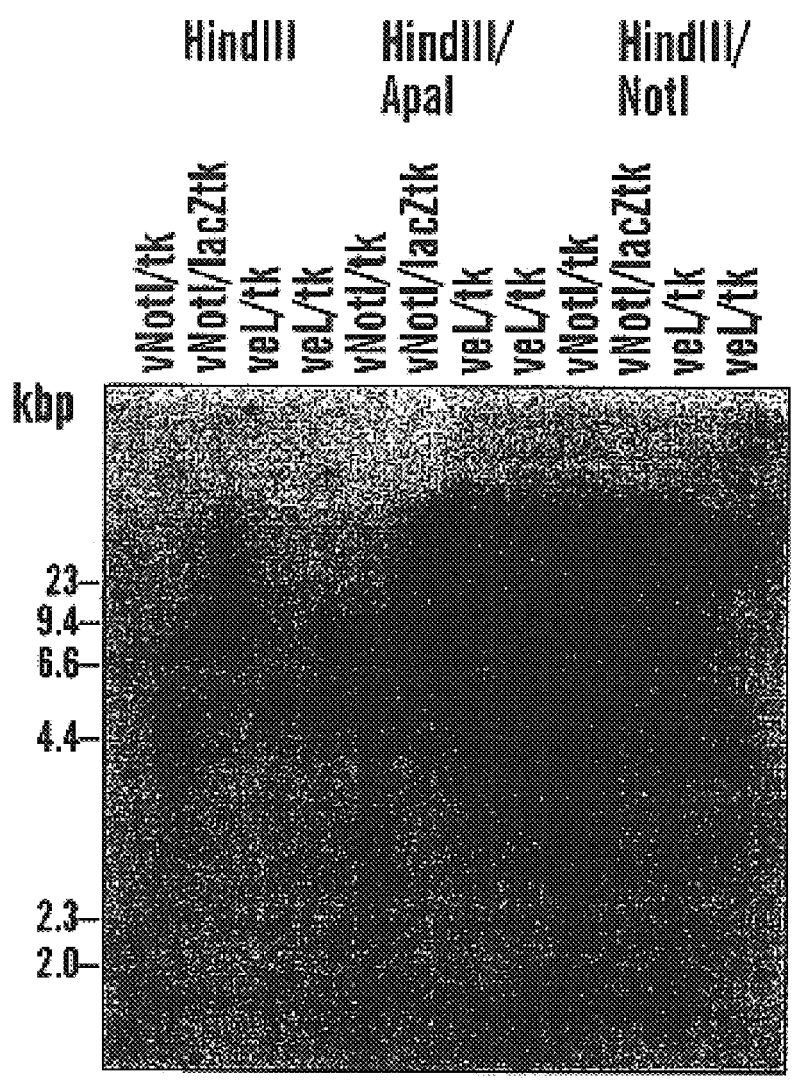
Figure 11B:
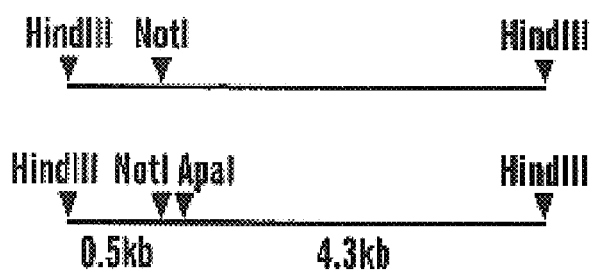

The genomes for vEL/tk and v7.5/tk were analyzed by Southern blotting to confirm the location of the ApaI and NotI sites in the HindIII J fragment as shown in FIGS. 11A and 11B. The filters were hybridized to $^{32}$P labeled HindIII J fragment derived from the p7.5/tk or pEL/tk. The genomes for v7.5/tk and vEL/tk have an ApaI site that does not appear in vNotI/tk (compare lanes 7 and 8 to lane 5 in each blot) whereas digestion with NotI and HindIII yield a set of fragments of equivalent size. The 0.5 kilobase HindIII/NotI or HindIII/ApaI fragment from the left hand side of HindIII J produced from NotI or ApaI digestion has electrophoresed off the bottom of the agarose gel.

Figure 12:
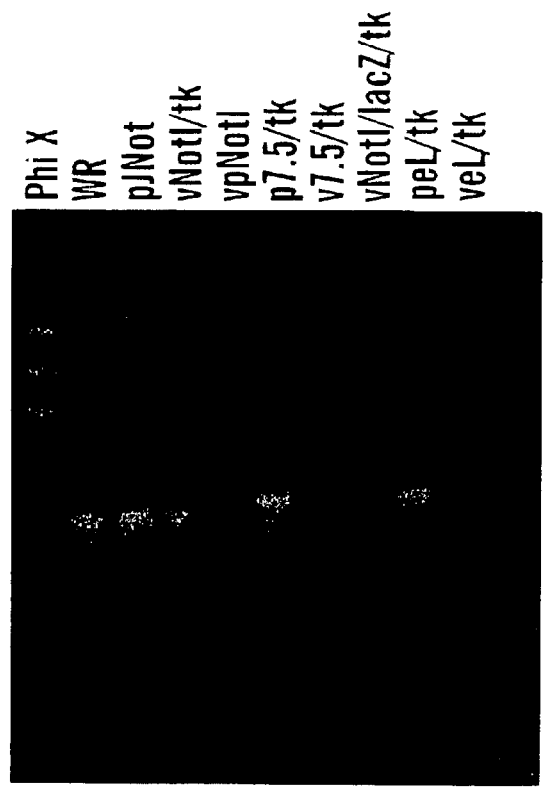
FIG. 12. Analysis of v7.5/tk and vEL/tk by PCR. One well of a 6 well dish of BSC-1 cells was infected with v7.5/tk, vEL/tk, vNotI/tk, vpNotI, vNotI/lacZ/tk, or wild type vaccinia WR at high multiplicity of infection (moi) and after 48 hours the cells were harvested, and the DNA was isolated using DNAzol (Gibco). The final DNA product was resuspended in 50 microliters of TE (10 mM TrisHCl, pH8.0. 1 mM EDTA) and used in a PCR with primers MM407 and MM408. The primers are separated by 518 nucleotides in vaccinia WR and yield a fragment containing the N terminus of the thymidine kinase gene. The products were electrophoresed through a 2% agarose gel. The leftmost sample contains phiX 174 HaeIII digestion products; all others contain the PCR product using primers MM407 and MM408 with the DNA sample indicated above the well FIG. 13. Promoter strength of recombinant viruses. The units of β-glu activity were determined as described by Miller (10) as adapted for 96-well plates. The $A_{405}$ values were determined on a microplate reader (Dynatech MR3000) and the β-glu activity was determined by comparison to β-glu (Clontech) standards analyzed in the same assay.

The definitive characterization of the promoter sequence utilized products of Polymerase Chain Reaction (PCR). A pair of primers flanking the beginning of the tk gene were used to generate a DNA fragment from the viruses vNotI/tk, v7.5/tk, or vEL/tk and their cognate plasmids as shown in FIG. 12. The PCR products for v7.5/tk and vEL/tk are the same size as those observed for the plasmids used to generate the viruses (p7.5/tk and pEL/tk) and larger than those seen for vaccinia WR and vNotI/tk. The PCR fragments were cloned into the plasmid pCRII, the nucleotide sequence was determined and shown to match the sequence displayed in FIG. 1.

Quantitation of Promoter Activity

The v7.5/tk and vEL/tk vectors have been designed to constitutively express elevated levels of insert protein in comparison to vNotI/tk. The level of RNA synthesis was measured by infecting confluent BSC-1 cells in the presence and absence of cytosine arabinoside (AraC) at an moi of 5, harvesting the cells, isolating the RNA using Trizol (Life Technologies) and analyzing the level of thymidine kinase RNA synthesis by primer extension (Weir, et al., *Nucleic Acids Research* 16:10267–10282 (1990)). Incubation with AraC blocks viral DNA replication, allowing one to identify the class of viral promoter.

The early class of viral promoters are active prior to DNA replication and will be unaffected by AraC in the infection. Late promoters are only expressed after the onset of DNA replication and their activity is abrogated in the presence of AraC. Perusal of the products on a denaturing polyacrylamide gel demonstrated that significantly more (estimated to be at least ten fold) tk RNA primer extension products were synthesized in vEL/tk infections as compared to vNot/tk. In cells infected with vNot/tk a single RNA start site insensitive to AraC incubation was observed whereas in vEL/tk infections two distinct start sites, one resistant to AraC and corresponding to the appropriate early start site (Davison, et al., *J. Mol. Biol.* 210:749–769 (1989)), and one species sensitive to AraC and corresponding to the appropriate late start of RNA (Davison, et al. *J. Mol. Biol* 210:771–784 (1989)) were observed (data not shown). The pattern of RNA species derived from infection with v7.5/tk was similar to that observed for vEL/tk with the absolute levels of RNA expression intermediate to that observed for vEL/tk and vNot/tk.

In order to verify the levels of expression for genes inserted into the viral vectors the *E.coli* gusA gene encoding for β-glucuronidase (β-glu) was cloned into vNotI/tk, v7.5/tk and vEL/tk viral vectors and the relative promoter strength was measured. The DNA fragment encoding for the β-glu gene was inserted into plasmids containing each promoter generating pJNot/tk–GUS, p7.5/tk–GUS and pEL/tk–GUS. The correct orientation of the insert β-glu gene in pJNot/tk was verified by restriction enzyme analysis. The plasmids were recombined with vNotI/tk and the recombinant viruses identified by staining with X-glu (Carroll, et al., 1995, BioTechniques 19:352–355), passaged for three rounds through Hutk⁻ cells, and expanded to generate the viral stocks vNotI/tk–GUS, v7.5/tk–GUS and vEL/tk–GUS. The structures of the recombinant viruses were verified by Southern blot analysis.

Figure 13:
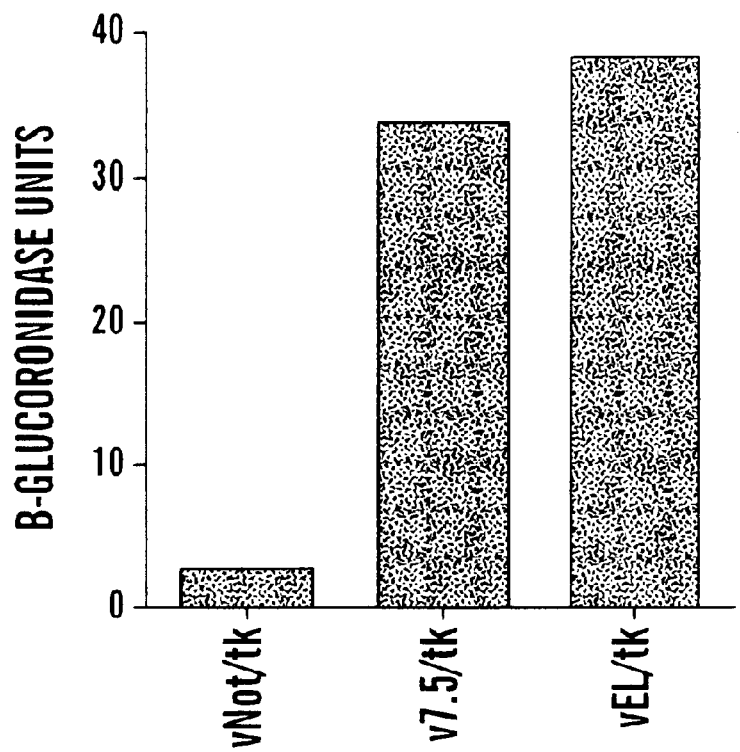

The level of expression of β-glu by vNotI/tk–GUS, v7.5/tk–GUS and vEL/tk–GUS was measured from infected confluent monolayers of BSC-1 cells in the presence or absence of AraC (FIG. 13). The level of β-glu expression for the v7.5/tk–GUS and vEL/tk was much higher than that observed for vNotI/tk–GUS and highest (approximately twenty fold higher) in the vEL/tk–GUS. Expression of β-glu was observed for all three viruses in the presence of cytosine arabinoside, indicating that each promoter is a member of the early class of viral promoters. The level of β-glu in vNotI/tk–GUS was unchanged in the presence or absence of AraC indicating that this promoter is only active early during infection, whereas the β-glu levels in v7.5/tk–GUS and vEL/tk–GUS were lower in the presence of AraC, indicating these promoters are active both early and late times during infection.

Biochemical Characterization of Virus Vectors

Figure 14:
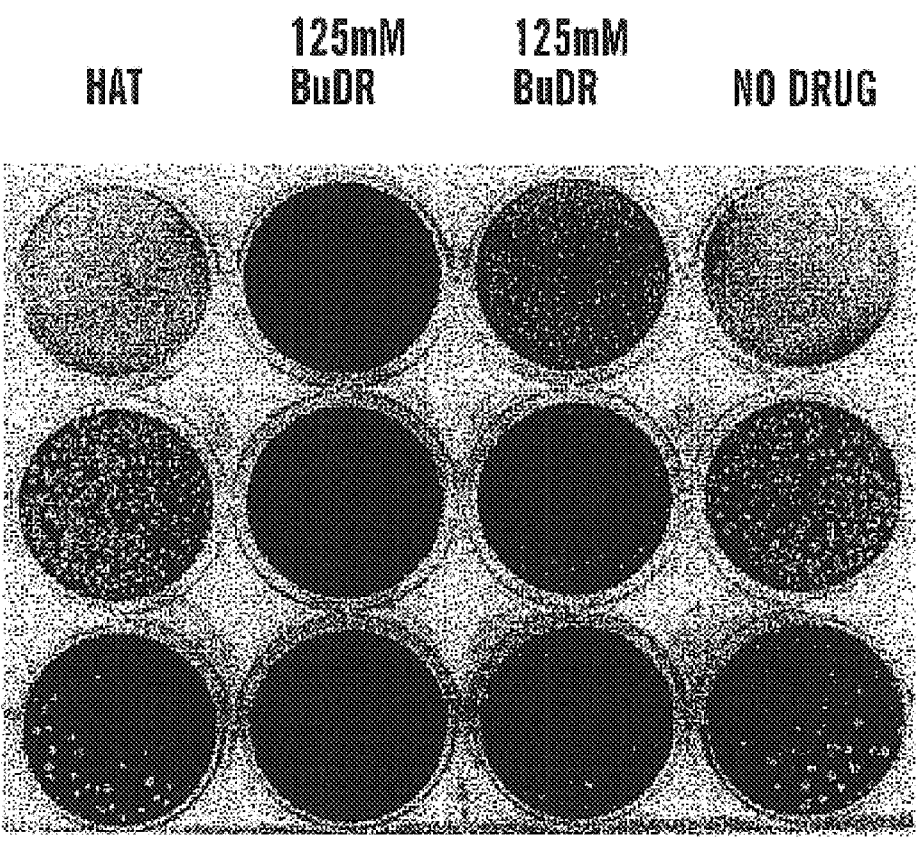
FIG. 14. Plaque assay on vEL/tk. Ten-fold dilutions of vEL/tk were incubated with Hutk⁻ cells (top to bottom) for one hour at 37° C. in 1 ml of E-MEM (Gibco) with 10% Fetal Bovine Serum for one hour, the media was replaced with 3 ml of E-MEM with 5% methyl cellulose (Sigma M-0387), 5% Fetal Bovine Serum and HAT supplement (Gibco), 25 or 125 mM bromodeoxyuridine, or no drug, incubated for 48 hours at 37° C., and stained with 0.5% Crystal Violet (Sigma C 0775), 20% ethanol, 7.5% formaldehyde.

The v7.5/tk and vEL/tk vectors were initially isolated by growth in the presence of HAT supplemented media and are designed to contain an active tk gene to allow selection for viruses with inserts via passage in Hutk- cells in the presence of bromodeoxyuridine (Earl, et al., in *Current Protocols in Molecular Biology*, Ausubel, et al., eds., Greene Publishing Associates/Wiley Interscience, New York (1991)). Both vectors were tested by plaque assay in Hutk⁻ cells using drug selection and the results for vEL/tk are shown in FIG. 14. Incubation without drug or with HAT supplement at a concentration sufficient to interfere with plaque formation for vpNot or vNot/lacZ/tk, (data not shown), gave an equivalent number of like-sized plaques. Surprisingly, an equal number of plaques, albeit much smaller in size, were observed for vEL/tk with incubation in 25 mM bromodeoxyuridine, a concentration sufficient to interfere with the ability of vaccinia WR to plaque on Hutk⁻ cells (data not shown). Addition of 125 mM bromodeoxyuridine was sufficient to inhibit plaque formation for vEL/tk (FIG. 14) and v7.5/tk (data not shown). The higher concentration of bromodeoxyuridine did not interfere with the growth of tk⁻ viruses such as vNotI/lacZ/tk (data not shown) or affect the viability of the Hutk⁻ cell line.

Construction of Recombinant Virus by Direct Ligation

Direct ligation vectors will only be useful for the generation of complex expression libraries if the production of infectious virus from the naked DNA is facile and efficient. Previously, helper virus activity was supplied in cells transfected with DNA ligation products by coinfection with conditionally lethal temperature sensitive virus (Merchlinsky, et al., *Virology.* 190:522–526 (1992)) or fowlpox (Scheiflinger, et al., *Proc. Natl. Acad. Sci. USA* 89:9977–9981 (1992)). Since high levels of replicating wild type virus interfere with the ability to package viral DNA and vaccinia virus can recombine with the input DNA, only conditionally defective vaccinia virus can be used as helper (Merchlinsky, et al., *Virology* 190:522–526 (1992)). Fowlpox should be a superior helper virus as it is used at 37° C., will not revert to a highly replicating strain, and, since it does not recombine with vaccinia DNA or productively infect primate cell lines, can be used at higher moi than vaccinia. In order to determine if fowlpox can serve as an efficient helper virus a series of wells from a 12 well plate containing BSC-1 cells were infected with varying mois of fowlpox and transfected with full length vaccinia WR DNA, the cells were harvested after 24, 48, or 72 hours and the virus titer was determined as shown in Table 8. Transfection of DNA sans fowlpox or fowlpox infection alone resulted in no plaques. The level of rescued vaccinia increased with later harvest and was proportional to the moi of the fowlpox infection.

TABLE 8

| FPV moi | Day harvested | Titer (pfu × 10⁻³) |
|---|---|---|
| 0.2 | 1 | 0 |
|  | 2 | 0.12 |
|  | 3 | 300 |
| 0.5 | 1 | 0 |
|  | 2 | 0.23 |
|  | 3 | 500 |
| 1.0 | 1 | 0 |
|  | 2 | 1.1 |
|  | 3 | 700 |

Table 8. Packaging of vaccinia DNA by fowlpox virus. Vaccinia DNA was transfected into BSC-1 cells infected with fowlpox virus using lipofectamine as described in Example 9 (Materials and Methods). The cells were harvested at 1, 2, or 3 days post transfection, lysed by freeze-thaw cycles and assayed for infectious virus by plaque assay on BSC-1 cells.

A 1.1 kilobase pair fragment of the ovalbumin cDNA (Pulaski, et al., Proc. Natl. Acad. Sci. USA 93:3669–3674 (1996)) was used as a model insert to study the generation of functional recombinant virus by direct ligation. The ovalbumin insert was modified as described in the Materials and Methods to include a NotI site at its 5' end, translation stop codons, a vaccinia transcription stop signal and an ApaI site at its 3' end. This insert was digested with NotI and ApaI and ligated with purified vEL/tk DNA arms that had been digested with NotI and ApaI. The ligation mix was transfected into fowlpox infected BSC-1 cells, cells were harvested, and after three days the cell extract was passaged on Hutk$^-$ cells in the presence or absence of 125 mM bromodeoxyuridine. The titer obtained without drug selection was $2.7 \times 10^3$ pfu and with drug selection $2.8 \times 10^3$ pfu. Individual plaques were picked from Hutk$^-$ cells in the presence and absence of bromodeoxyuridine and tested for the presence of the ovalbumin insert by dot blot hybridization with an ovalbumin cDNA probe. All 15 plaques picked in the presence of bromodeoxyuridine, and all 10 plaques picked in its absence contained the ovalbumin insert. These viruses were named vEL/tk-ovaFL. Two individual clones were expanded further and tested for the ability to sensitize host cells to lysis by ova 257–264 specific cytotoxic T lymphocytes (CTL). The results of this experiment are shown in Table 9. As controls, vaccinia recombinant for an ova 257–264 minigene, v7.5/tk-ova and vEL/tk-ova, were generated by homologous recombination. These ova peptide recombinant viruses were tested in concert with the vEL/tk-ovaFL clones for the ability to sensitize host cells to lysis by ova specific CTL. As shown in Table 9, infection with either full length or minigene ovalbumin vaccinia recombinants was as efficient as pulsing with 1 μM purified OVA 257–264 peptide for sensitization of target cells to lysis by OVA-specific CTL.

TABLE 9

| MC57G cells: | Effector:Target Ratio | |
|---|---|---|
| | 2:1 | 10:1 |
| | (Percent Specific Lysis) | |
| Untreated | −1.3 | −1.3 |
| ova 257–264 peptide, 1 μM | 54 | 83 |
| vEL/tk | −0.5 | 0 |
| v7.5/tk-ova Homologous Recombination | 50 | 78 |
| vEL/tk-ova Homologous Recombination | 47 | 71 |
| vEL/tk-ovaFL Direct Ligation Clone 1 | 48 | 70 |
| vEL/tk-ovaFL Direct Ligation Clone 2 | 46 | 74 |

Table 9. CML assay on recombinant vaccinia virus infected cells. Virally infected MC57G cells were generated as described in Example 9 (Materials and Methods). One sample of MC57G cells was treated with ova257–264 peptide (1 μM), another sample of cells was left untreated. Cells were incubated with two different ratios of ova specific cytotoxic T lymphocytes for 4 hours at 37° C. and percent specific lysis was determined as described in Example 9 (Materials and Methods).

Discussion

Large DNA viruses are particularly useful expression vectors for the study of cellular processes as they can express many different proteins in their native form in a variety of cell lines. In addition, gene products expressed in recombinant vaccinia virus have been shown to be efficiently processed and presented in association with MHC class I for stimulation of cytotoxic T cells. The gene of interest is normally cloned in a plasmid under the control of a promoter flanked by sequences homologous to a non-essential region in the virus and the cassette is introduced into the genome via homologous recombination. A panoply of vectors for expression, selection and detection have been devised to accommodate a variety of cloning and expression strategies. However, homologous recombination is an ineffective means of making a recombinant virus in situations requiring the generation of complex libraries or when the insert DNA is large. An alternative strategy for the construction of recombinant genomes relying on direct ligation of viral DNA "arms" to an insert and the subsequent rescue of infectious virus has been explored for the genomes of poxvirus (Merchlinsky, et al., Virology 190:522–526 (1992); Pfleiderer, et al., J. General Virology 76:2957–2962 (1995); Scheiflinger, et al., Proc. Natl. Acad. Sci. USA 89:9977–9981 (1992)), herpesvirus (Rixon, et al., J. General Virology 71:2931–2939 (1990)) and baculovirus (Ernst, et al., Nucleic Acids Research 22:2855–2856 (1994)).

Poxviruses are ubiquitous vectors for studies in eukaryotic cells as they are easily constructed and engineered to express foreign proteins at high levels. The wide host range of the virus allows one to faithfully express proteins in a variety of cell types. Direct cloning strategies have been devised to extend the scope of applications for poxvirus viral chimeras in which the recombinant genomes are constructed in vitro by direct ligation of DNA fragments to vaccinia "arms" and transfection of the DNA mixture into cells infected with a helper virus (Merchlinsky, et al., Virology 190:522–526 (1992); Scheiflinger, et al., Proc. Natl. Acad. Sci. USA 89:9977–9981 (1992)). This approach has been used for high level expression of foreign proteins (Pfleiderer, et al., J. Gen. Virology 76:2957–2962 (1995)) and to efficiently clone fragments as large as 26 kilobases in length (Merchlinsky, et al., Virology 190:522–526 (1992)).

Vaccinia virus DNA is not infectious as the virus cannot utilize cellular transcriptional machinery and relies on its own proteins for the synthesis of viral RNA. Previously, temperature sensitive conditional lethal (Merchlinsky, et al., Virology 190:522–526 (1992)) or non-homologous poxvirus fowlpox (Scheiflinger, et al., Proc. Natl. Acad. Sci. USA 89:9977–9981 (1992)) have been utilized as helper virus for packaging. An ideal helper virus will efficiently generate infectious virus but not replicate in the host cell or recombine with the vaccinia DNA products. Fowlpox virus has the properties of an ideal helper virus as it is used at 37° C., will not revert to a highly replicating strain, and, since it does not recombine with vaccinia DNA or productively infect primate cell lines, can be used at relatively high moi.

The utility of the vaccinia based direct ligation vector vNotI/tk, has been described by Merchlinsky, et al., Virology 190:522–526 (1992). This genome lacks the NotI site normally present in the HindIII F fragment and contains a unique NotI site at the beginning of the thymidine kinase gene in frame with the coding sequence. This allows the insertion of DNA fragments into the NotI site and the identification of recombinant genomes by drug selection. The vNotI/tk vector can be used to efficiently clone large DNA fragments but does not fix the orientation of the DNA insert or lead to high expression of the foreign protein. This example describes the construction and characterization of a pair of vaccinia DNA vector genomes v7.5/tk and vEL/tk suitable for direct ligation. The v7.5/tk and vEL/tk vectors were designed to contain unique restriction sites for NotI and ApaI at the beginning of the thymidine kinase gene allowing the oriented cloning of DNA and eliminating the intact genomes arising from relegation of vaccinia vector arms.

The vNotI/tk vector will only express foreign proteins at the level of the thymidine kinase gene, a weakly expressed gene only made early during viral infection. To induce high levels of protein expression the sequences encoding for the viral 7.5 k promoter and a synthetic EL promoter devised by Chakrabarti and Moss were used to replace the endogenous thymidine kinase promoter. The levels of expression induced by either promoter was much higher than that observed in vNotI/tk and the promoters were active at all times post infection. These continuous expression vectors are applicable in cases dependent on early expression, such as T-cell epitope presentation, as well as for bulk expression of proteins.

Use of the thymidine kinase gene as the insertion site for foreign DNA allows implementation of selection protocols for distinguishing recombinants from helper or wild type genomes. The level of tk expression in v7.5/tk and vEL/tk should be much higher than in vaccinia WR or vNot/tk. However, the ApaI site at the beginning of the tk gene in v7.5/tk and vEL/tk was formed from vNot/tk by adding extra nucleotides at the NotI site. The additional nucleotides increase the amino acid sequence at the N terminus of the wild type tk gene from Met-Asn-Gly to Met-Gly-Pro-Ala-Ala-Asn-Gly (SEQ ID NO:38) in v7.5/tk and vEL/tk. Modifications in the expression level and N terminal amino acid sequence of the thymidine kinase gene may increase (more protein) or decrease (different sequence) the sensitivity of the virus to bromodeoxyuridine. Plaques, albeit smaller, were observed with v7.5/tk and vEL/tk infection at a concentration of bromodeoxyuridine sufficient to completely suppress plaque formation for wild type vaccinia WR. Plaque formation was suppressed at five-fold higher concentrations of bromodeoxyuridine, a level of drug that does not interfere with the viability of the cells or impede the ability of tk⁻ virus to form plaques. The explanation for the altered sensitivity to bromodeoxyuridine awaits further characterization of the protein as the altered thymidine kinase gene may have a different reaction rate for formation of the triphosphate form of the bromodeoxyuridine or a reduced ability to bind bromodeoxyuridine.

The development of direct ligation vectors has increased the possible applications for poxvirus expression vectors. The v7.5/tk and vEL/tk vectors were designed to incorporate the advantages of oriented cloning, high levels of expression of foreign protein, and the selection for recombinant viruses, into direct ligation vectors. They were shown to express high levels of proteins at all times during infection. The utility of these vectors was demonstrated by constructing recombinants containing a CTL epitope for ovalbumin (constructed by homologous recombination with a plasmid) or the ovalbumin coding sequence (constructed by direct ligation protocol) and showing how both recombinants were able to elicit a strong CTL response The application of these vectors to protocols for construction of complex expression libraries requires efficient production of recombinants and strong selection to eliminate or minimize wild type and contaminants. The use of two restriction sites allows one to design cloning strategies for the oriented cloning of DNA fragments such as products of PCR (Pfleiderer, et al., *J. General Virology* 76:2957–2962 (1995)) and increases the frequency of the desired recombinant as wild type genomes can no longer be generated by ligation of vaccinia arms. When v7.5/tk or vEL/tk DNA previously digested with NotI and ApaI was transfected into cells infected with fowlpox the virus titer was one hundred fold lower than for intact uncut DNA. Also, all plaques isolated in the presence and absence of bromodeoxyuridine (15 with bromodeoxyuridine and 10 without) during the isolation of the vEL/tk–ovaFL contained the ovalbumin insert. The efficiency of infectious virus formation is also increased with the use of fowlpox, helper virus at relatively high moi. Also, transfection of large DNA fragments varies with the type and preparation of lipid (Miles Carroll, personal communication) and we are presently assaying different lipid mixtures and cell types as well as investigating other parameters to find optimum conditions for the direct ligation protocol. The v7.5/tk and vEL/tk vectors provide a set of universally applicable direct ligation cloning vectors for poxviruses.

The present invention is not to be limited in scope by the specific embodiments described which are intended as single illustrations of individual aspects of the invention, and any constructs, viruses or enzymes which are functionally equivalent are within the scope of this invention. Indeed, various modifications of the invention in addition to those shown and described herein will become apparent to those skilled in the art from the foregoing description and accompanying drawings. Such modifications are intended to fall within the scope of the appended claims.

All publications and patent applications mentioned in this specification are herein incorporated by reference to the same extent as if each individual publication or patent application was specifically and individually indicated to be incorporated by reference.

What is claimed is:

1. A method for selecting a nucleic acid molecule encoding a target epitope of cytotoxic T-lymphocytes, comprising:
   (a) contacting host cells with cytotoxic T-lymphocytes specific for said target epitope under conditions wherein a host cell expressing said target epitope undergoes a lytic event upon contact with said cytotoxic T-lymphocytes; wherein said host cells comprise a library of heterologous nucleic acid molecules, at least one of said heterologous nucleic acid molecules encoding said target epitope, wherein said library is constructed in a vector which expresses said target epitope in said host cells, wherein said host cells express a defined MHC molecule, and wherein said cytotoxic T-lymphocytes are restricted for said MHC molecule; and
   (b) recovering vector from floating host cells which are undergoing a lytic event;
   wherein said target epitope is selected from the group consisting of: a target epitope which is differentially expressed in infected cells and a target epitope which is specific for an-autoimmune disease.

2. The method of claim 1, wherein said target epitope is differentially expressed in infected cells.

3. The method of claim 2, wherein said infected cells are infected with a pathogen selected from the group consisting of: a virus, a fungus, and a mycobacterium.

4. The method of claim 3, wherein said pathogen is a virus.

5. The method of claim 3, wherein said infected cells are infected with a fungus.

6. The method of claim 3, wherein said infected cells are infected with a mycobacterium.

7. The method of claim 1, further comprising purifying said vector.

8. The method of claim 1, further comprising:
   (c) purifying said vector;
   (d) transferring said vector to a population of host cells, wherein said vector expresses said target epitope in said host cells, and wherein said host cells express a defined MHC molecule;
   (e) contacting said host cells with cytotoxic T-lymphocytes specific for said target epitope and restricted for said MHC molecule, under conditions wherein a host cell expressing said target epitope will undergo a lytic event upon contact with said cytotoxic T-lymphocytes; and
   (f) recovering vector from floating host cells which are undergoing a lytic event.

9. The method of claim 1, wherein said vector is a virus.

10. The method of claim 9, wherein said vector is a virus capable of producing infectious viral particles in eukaryotic cells.

11. The method of claim 10, wherein the naturally-occurring genome of said viral vector is linear, double stranded DNA.

12. The method of claim 10, wherein said viral vector is capable of producing infectious viral particles in mammalian cells.

13. The method of claim 12, wherein the naturally-occurring genome of said viral vector is linear, double-stranded DNA.

14. The method of claim 10, wherein said viral vector is a poxvirus vector.

15. The method of claim 14, wherein said poxvirus vector is a vaccinia virus vector.

16. The method of claim 9, wherein said host cells are permissive for the production of infectious viral particles of said viral vector.

17. The method of claim 14, wherein said viral vector further comprises a transcriptional control signal in operable association with said heterologous nucleic acid molecules, and wherein said transcriptional control signal functions in a poxvirus.

18. The method of claim 17, wherein said transcriptional control signal comprises a promoter.

19. The method of claim 18, wherein said promoter is constitutive.

20. The method of claim 18, wherein said promoter is selected from the group consisting of: a vaccinia virus p7.5 promoter and a synthetic early/late promoter.

21. The method of claim 17, wherein said transcriptional control signal comprises a transcriptional termination signal.

22. The method of claim 17, wherein said vector further comprises a translational control signal associated with said transcriptional control signal.

23. The method of claim 22, wherein said translational control signal comprises a translation initiation codon operably linked to said heterologous nucleic acid molecules.

24. The method of claim 23, wherein said translation initiation codon occurs in one of three reading frames.

25. The method of claim 11, wherein said library is constructed by a method comprising:
   (a) cleaving an isolated linear DNA virus genome to produce a first viral fragment and a second viral fragment, wherein said first fragment is nonhomologous with said second fragment;
   (b) providing a population of transfer plasmids comprising said heterologous nucleic acid molecules flanked by a 5' flanking region and a 3' flanking region, wherein said 5' flanking region is homologous to said first viral fragment and said 3' flanking region is homologous to said second viral fragment; and wherein said transfer plasmids are capable of homologous recombination with said first and second viral fragments such that a viable virus genome is formed;

(c) introducing said transfer plasmids and said first and second viral fragments into a host cell under conditions wherein a transfer plasmid and said viral fragments undergo in vivo homologous recombination, thereby producing a viable modified virus genome comprising a heterologous nucleic acid molecule; and (d) recovering said modified virus genome.

26. The method of claim 25, wherein said virus genome comprises a first recognition site for a first restriction endonuclease and a second recognition site for a second restriction endonuclease; and wherein said first and second viral fragments are produced by digesting said viral genome with said first restriction endonuclease and said second restriction endonuclease, and isolating said first and second viral fragments.

27. The method of claim 26, wherein said first and second recognition sites are physically arranged in said genome such that the region extending between said first and second viral fragments is not essential for virus infectivity.

28. The method of claim 25, wherein said modified virus genome is packaged in an infectious viral particle.

29. The method of claim 13, wherein said library is constructed by a method comprising:

(a) cleaving an isolated linear DNA virus genome to produce a first viral fragment and a second viral fragment, wherein said first fragment is nonhomologous with said second fragment;

(b) providing a population of transfer plasmids comprising said heterologous nucleic acid molecules flanked by a 5' flanking region and a 3' flanking region, wherein said 5' flanking region is homologous to said first viral fragment and said 3' flanking region is homologous to said second viral fragment; and wherein said transfer plasmids are capable of homologous recombination with said first and second viral fragments such that a viable virus genome is formed;

(c) introducing said transfer plasmids and said first and second viral fragments into a host cell under conditions wherein a transfer plasmid and said viral fragments undergo in vivo homologous recombination, thereby producing a viable modified virus genome comprising a heterologous nucleic acid molecule; and (d) recovering said modified virus genome.

30. The method of claim 29, wherein said virus genome comprises a first recognition site for a first restriction endonuclease and a second recognition site for a second restriction endonuclease; and wherein said first and second viral fragments are produced by digesting said viral genome with said first restriction endonuclease and said second restriction endonuclease, and isolating said first and second viral fragments.

31. The method of claim 30, wherein said first and second recognition sites are physically arranged in said genome such that the region extending between said first and second viral fragments is not essential for virus infectivity.

32. The method of claim 29, wherein said isolated virus genome is a poxvirus genome.

33. The method of claim 32, wherein said poxvirus genome is a vaccinia virus genome.

34. The method of claim 32, wherein said transfer plasmids and said first and second viral fragments are introduced into a host cell comprising a helper virus, wherein said host cell is non-permissive for the production of infectious virus particles of said helper virus.

35. The method of claim 34, wherein said helper virus is an avipoxvirus.

36. The method of claim 35, wherein said avipoxvirus is a fowlpox virus.

37. The method of claim 30, wherein said first and second restriction enzyme recognition sites are situated in a thymidine kinase gene.

38. The method of claim 32, wherein said first and second restriction enzyme recognition sites are situated in a vaccinia virus HindIII J fragment.

39. The method of claim 38, wherein said first and second restriction enzyme recognition sites are situated in a vaccinia virus thymidine kinase gene.

40. The method of claim 38, wherein said first restriction enzyme is NotI, and wherein said first restriction enzyme recognition site is GCGGCCGC.

41. The method of claim 38, wherein said second restriction enzyme site is ApaI, and wherein said second restriction enzyme recognition site is GGGCCC.

42. The method of claim 33, wherein said isolated virus genome is a v7.5/tk virus genome.

43. The method of claim 33, wherein said isolated virus genome is a vEL/tk virus genome.

44. The method of claim 32, wherein the 5' and 3' flanking regions of said transfer plasmids are capable of homologous recombination with a vaccinia virus thymidine kinase gene.

45. The method of claim 44, wherein the 5' and 3' flanking regions of said transfer plasmids are capable of homologous recombination with a vaccinia virus HindIII J fragment.

46. The method of claim 44, wherein said transfer plasmids comprise heterologous nucleic acid molecules ligated into a plasmid selected from the group consisting of:

(a) p7.5/ATG0/tk which comprises SEQ ID NO:6, (b) p7.5/ATG1/tk which comprises SEQ ID NO:7, (c) p7.5/ATG2/tk which comprises SEQ ID NO:8, and (d) p7.5/ATG3/tk, which comprises SEQ ID NO:9.

47. The method of claim 1, wherein said host cells are part of a monolayer, and wherein the floating host cells which are undergoing a lytic event are released from said monolayer.

48. The method of claim 1, wherein said MHC molecule is a class I MHC molecule.

49. The method of claim 8, wherein said host cells are part of a monolayer, and wherein the floating host cells which are undergoing a lytic event are released from said monolayer.

50. The method of claim 8, wherein said MHC molecule is a class I MHC molecule.

51. The method of claim 47, wherein (b) comprises recovering said host cells which are undergoing a lytic event as floating cells.

52. The method of claim 49, wherein (b) comprises recovering said host cells which are undergoing a lytic event as floating cells.

53. The method of claim 8, wherein (b) comprises recovering said host cells which are undergoing a lytic event as floating cells.

54. The method of claim 8, wherein (f) comprises recovering said host cells which are undergoing a lytic event as floating cells.

* * * * *

SEQUENCE LISTING

```
<160> NUMBER OF SEQ ID NOS: 38

<210> SEQ ID NO 1
<211> LENGTH: 69
<212> TYPE: DNA
<213> ORGANISM: Artificial Sequence
<220> FEATURE:
<223> OTHER INFORMATION: Synthetic Construct
<220> FEATURE:
<221> NAME/KEY: CDS
<222> LOCATION: (46)..(69)
```

```
<400> SEQUENCE: 1
ggccaaaaat tgaaaaacta gatctatttta ttgcacgcgg ccgcc atg ggc ccg gcc        57
                                                Met Gly Pro Ala
                                                  1 gcc aac ggc gga                                                            69
Ala Asn Gly Gly
 5

<210> SEQ ID NO 2
<211> LENGTH: 8
<212> TYPE: PRT
<213> ORGANISM: Artificial Sequence
<220> FEATURE:
<223> OTHER INFORMATION: Synthetic Construct

<400> SEQUENCE: 2

Met Gly Pro Ala Ala Asn Gly Gly
 1               5

<210> SEQ ID NO 3
<211> LENGTH: 75
<212> TYPE: DNA
<213> ORGANISM: Artificial Sequence
<220> FEATURE:
<223> OTHER INFORMATION: Synthetic Construct
<220> FEATURE:
<221> NAME/KEY: CDS
<222> LOCATION: (52)..(75)

<400> SEQUENCE: 3
ggccaaaaat tgaaatttta ttttttttt ttggaatata aagcggccgc c atg ggc          57
                                                        Met Gly
                                                          1 ccg gcc gcc aac ggc gga                                                    75
Pro Ala Ala Asn Gly Gly
         5

<210> SEQ ID NO 4
<211> LENGTH: 8
<212> TYPE: PRT
<213> ORGANISM: Artificial Sequence
<220> FEATURE:
<223> OTHER INFORMATION: Synthetic Construct

<400> SEQUENCE: 4

Met Gly Pro Ala Ala Asn Gly Gly
 1               5

<210> SEQ ID NO 5
<211> LENGTH: 57
<212> TYPE: DNA
<213> ORGANISM: Artificial Sequence
<220> FEATURE:
<223> OTHER INFORMATION: Synthetic Construct

<400> SEQUENCE: 5
ggccaaaaat tgaaaaacta gatctatttta ttgcacgcgg ccgccatggg cccggcc          57

<210> SEQ ID NO 6
<211> LENGTH: 145
<212> TYPE: DNA
<213> ORGANISM: Artificial Sequence
<220> FEATURE:
<223> OTHER INFORMATION: Synthetic Construct

<400> SEQUENCE: 6
```

```
ggccaaaaat tgaaaaacta gatctattta ttgcacgcgg ccgccgtgga tcccccgggc      60
tgcaggaatt cgatatcaag cttatcgata ccgtcgacct cgagggggg cctaactaac     120 taattttgtt tttgtgggcc cggcc                                          145
```

```
<210> SEQ ID NO 7
<211> LENGTH: 148
<212> TYPE: DNA
<213> ORGANISM: Artificial Sequence
<220> FEATURE:
<223> OTHER INFORMATION: Synthetic Construct

<400> SEQUENCE: 7
```

```
ggccaaaaat tgaaaaacta gatctattta ttgcacgcgg ccgccatggt ggatccccccg     60 ggctgcagga attcgatatc aagcttatcg ataccgtcga cctcgagggg gggcctaact    120
aactaatttt gttttttgtgg gcccggcc                                       148
```

```
<210> SEQ ID NO 8
<211> LENGTH: 149
<212> TYPE: DNA
<213> ORGANISM: Artificial Sequence
<220> FEATURE:
<223> OTHER INFORMATION: Synthetic Construct

<400> SEQUENCE: 8
```

```
ggccaaaaat tgaaaaacta gatctattta ttgcacgcgg ccgccatgag tggatccccc      60
gggctgcagg aattcgatat caagcttatc gataccgtcg acctcgaggg ggggcctaac    120
taactaattt tgttttttgtg ggcccggcc                                      149
```

```
<210> SEQ ID NO 9
<211> LENGTH: 150
<212> TYPE: DNA
<213> ORGANISM: Artificial Sequence
<220> FEATURE:
<223> OTHER INFORMATION: Synthetic Construct

<400> SEQUENCE: 9
```

```
ggccaaaaat tgaaaaacta gatctattta ttgcacgcgg ccgccatgac gtggatcccc      60
cgggctgcag gaattcgata tcaagcttat cgataccgtc gacctcgagg ggggcctaa     120 ctaactaatt ttgtttttgt gggcccggcc                                     150
```

```
<210> SEQ ID NO 10
<211> LENGTH: 8
<212> TYPE: PRT
<213> ORGANISM: Artificial Sequence
<220> FEATURE:
<223> OTHER INFORMATION: Synthetic Construct

<400> SEQUENCE: 10

Ser Ile Ile Asn Phe Glu Lys Leu
 1               5
```

```
<210> SEQ ID NO 11
<211> LENGTH: 10
<212> TYPE: DNA
<213> ORGANISM: Artificial Sequence
<220> FEATURE:
<223> OTHER INFORMATION: Synthetic Construct

<400> SEQUENCE: 11
```

```
tacaacgagg                                                            10
```

```
<210> SEQ ID NO 12
<211> LENGTH: 10
<212> TYPE: DNA
<213> ORGANISM: Artificial Sequence
<220> FEATURE:
<223> OTHER INFORMATION: Synthetic Construct

<400> SEQUENCE: 12
gtcagagcat                                                            10

<210> SEQ ID NO 13
<211> LENGTH: 10
<212> TYPE: DNA
<213> ORGANISM: Artificial Sequence
<220> FEATURE:
<223> OTHER INFORMATION: Synthetic Construct

<400> SEQUENCE: 13
ggaccaagtc                                                            10

<210> SEQ ID NO 14
<211> LENGTH: 10
<212> TYPE: DNA
<213> ORGANISM: Artificial Sequence
<220> FEATURE:
<223> OTHER INFORMATION: Synthetic Construct

<400> SEQUENCE: 14
tcagacttca                                                            10

<210> SEQ ID NO 15
<211> LENGTH: 10
<212> TYPE: DNA
<213> ORGANISM: Artificial Sequence
<220> FEATURE:
<223> OTHER INFORMATION: Synthetic Construct

<400> SEQUENCE: 15
tacctatggc                                                            10

<210> SEQ ID NO 16
<211> LENGTH: 10
<212> TYPE: DNA
<213> ORGANISM: Artificial Sequence
<220> FEATURE:
<223> OTHER INFORMATION: Synthetic Construct

<400> SEQUENCE: 16
tgtcacatac                                                            10

<210> SEQ ID NO 17
<211> LENGTH: 10
<212> TYPE: DNA
<213> ORGANISM: Artificial Sequence
<220> FEATURE:
<223> OTHER INFORMATION: Synthetic Construct

<400> SEQUENCE: 17
tcggtcacag                                                            10

<210> SEQ ID NO 18
<211> LENGTH: 10
<212> TYPE: DNA
<213> ORGANISM: Artificial Sequence
<220> FEATURE:
<223> OTHER INFORMATION: Synthetic Construct
```

```
<400> SEQUENCE: 18
atctggtaga                                                              10

<210> SEQ ID NO 19
<211> LENGTH: 10
<212> TYPE: DNA
<213> ORGANISM: Artificial Sequence
<220> FEATURE:
<223> OTHER INFORMATION: Synthetic Construct

<400> SEQUENCE: 19
cttatccacg                                                              10

<210> SEQ ID NO 20
<211> LENGTH: 10
<212> TYPE: DNA
<213> ORGANISM: Artificial Sequence
<220> FEATURE:
<223> OTHER INFORMATION: Synthetic Construct

<400> SEQUENCE: 20
catgtctcaa                                                              10

<210> SEQ ID NO 21
<211> LENGTH: 10
<212> TYPE: DNA
<213> ORGANISM: Artificial Sequence
<220> FEATURE:
<223> OTHER INFORMATION: Synthetic Construct

<400> SEQUENCE: 21
gatcaagtct                                                              10

<210> SEQ ID NO 22
<211> LENGTH: 10
<212> TYPE: DNA
<213> ORGANISM: Artificial Sequence
<220> FEATURE:
<223> OTHER INFORMATION: Synthetic Construct

<400> SEQUENCE: 22
ctgatccatg                                                              10

<210> SEQ ID NO 23
<211> LENGTH: 53
<212> TYPE: DNA
<213> ORGANISM: Artificial Sequence
<220> FEATURE:
<223> OTHER INFORMATION: Synthetic Construct

<400> SEQUENCE: 23
ggccaaaaat tgaaaaacta gatctattta ttgcacgcgg ccgccatggg ccc             53

<210> SEQ ID NO 24
<211> LENGTH: 53
<212> TYPE: DNA
<213> ORGANISM: Artificial Sequence
<220> FEATURE:
<223> OTHER INFORMATION: Synthetic Construct

<400> SEQUENCE: 24
ggccgggccc atggcggccg cgtgcaataa atagatctag tttttcaatt ttt             53

<210> SEQ ID NO 25
```

```
<211> LENGTH: 59
<212> TYPE: DNA
<213> ORGANISM: Artificial Sequence
<220> FEATURE:
<223> OTHER INFORMATION: Synthetic Construct

<400> SEQUENCE: 25
ggccaaaaat tgaaatttta tttttttttt ttggaatata aagcggccgc catgggccc      59

<210> SEQ ID NO 26
<211> LENGTH: 59
<212> TYPE: DNA
<213> ORGANISM: Artificial Sequence
<220> FEATURE:
<223> OTHER INFORMATION: Synthetic Construct

<400> SEQUENCE: 26
ggccgggccc atggcggccg ctttatattc caaaaaaaaa aaataaaatt tcaattttt      59

<210> SEQ ID NO 27
<211> LENGTH: 39
<212> TYPE: DNA
<213> ORGANISM: Artificial Sequence
<220> FEATURE:
<223> OTHER INFORMATION: Synthetic Construct

<400> SEQUENCE: 27
gggaaagggg cggccgccat gttacgtcct gtagaaacc                            39

<210> SEQ ID NO 28
<211> LENGTH: 36
<212> TYPE: DNA
<213> ORGANISM: Artificial Sequence
<220> FEATURE:
<223> OTHER INFORMATION: Synthetic Construct

<400> SEQUENCE: 28
gggaaagggg ggccctcatt gtttgcctcc ctgctg                               36

<210> SEQ ID NO 29
<211> LENGTH: 39
<212> TYPE: DNA
<213> ORGANISM: Artificial Sequence
<220> FEATURE:
<223> OTHER INFORMATION: Synthetic Construct

<400> SEQUENCE: 29
gggaaagggg cggccgcctc attgtttgcc tccctgctg                            39

<210> SEQ ID NO 30
<211> LENGTH: 70
<212> TYPE: DNA
<213> ORGANISM: Artificial Sequence
<220> FEATURE:
<223> OTHER INFORMATION: Synthetic Construct

<400> SEQUENCE: 30
ggccaaaaat tgaaaaacta gatctatttta ttgcaccatg agtataatca actttgaaaa    60
actgtagtga                                                            70

<210> SEQ ID NO 31
<211> LENGTH: 71
<212> TYPE: DNA
<213> ORGANISM: Artificial Sequence
<220> FEATURE:
<223> OTHER INFORMATION: Synthetic Construct
```

```
<400> SEQUENCE: 31
ggcctcacta cagttttca aagttgatta atactcatgg tgcaataaat agatctagtt    60
tttcaatttt t                                                       71

<210> SEQ ID NO 32
<211> LENGTH: 77
<212> TYPE: DNA
<213> ORGANISM: Artificial Sequence
<220> FEATURE:
<223> OTHER INFORMATION: Synthetic Construct

<400> SEQUENCE: 32
ggccaaaaat tgaaatttta ttttttttt ttggaatata aaccatgagt ataatcaact    60
ttgaaaaact gtagtga                                                 77

<210> SEQ ID NO 33
<211> LENGTH: 77
<212> TYPE: DNA
<213> ORGANISM: Artificial Sequence
<220> FEATURE:
<223> OTHER INFORMATION: Synthetic Construct

<400> SEQUENCE: 33
ggcctcacta cagttttca aagttgatta tactcatggt ttatattcca aaaaaaaaa    60 ataaaatttc aattttt                                                 77

<210> SEQ ID NO 34
<211> LENGTH: 36
<212> TYPE: DNA
<213> ORGANISM: Artificial Sequence
<220> FEATURE:
<223> OTHER INFORMATION: Synthetic Construct

<400> SEQUENCE: 34
gcaggtgcgg ccgccgtgga tcccccgggc tgcagg                            36

<210> SEQ ID NO 35
<211> LENGTH: 47
<212> TYPE: DNA
<213> ORGANISM: Artificial Sequence
<220> FEATURE:
<223> OTHER INFORMATION: Synthetic Construct

<400> SEQUENCE: 35
gtaccgggcc cacaaaaaca aaattagtta gttaggcccc ccctcga                47

<210> SEQ ID NO 36
<211> LENGTH: 27
<212> TYPE: DNA
<213> ORGANISM: Artificial Sequence
<220> FEATURE:
<223> OTHER INFORMATION: Synthetic Construct

<400> SEQUENCE: 36
ggtccctatt gttacagatg gaagggt                                      27

<210> SEQ ID NO 37
<211> LENGTH: 24
<212> TYPE: DNA
<213> ORGANISM: Artificial Sequence
<220> FEATURE:
<223> OTHER INFORMATION: Synthetic Construct
```

```
<400> SEQUENCE: 37
ccttcgtttg ccatacgctc acag                                            24

<210> SEQ ID NO 38
<211> LENGTH: 7
<212> TYPE: PRT
<213> ORGANISM: Artificial Sequence
<220> FEATURE:
<223> OTHER INFORMATION: Synthetic Construct

<400> SEQUENCE: 38

Met Gly Pro Ala Ala Asn Gly
1               5
```